United States Patent
Sugawara et al.

(10) Patent No.: US 10,409,146 B2
(45) Date of Patent: Sep. 10, 2019

(54) IMAGE PROJECTION SYSTEM, IMAGE PROJECTION DEVICE, IMAGE PROJECTION METHOD, IMAGE PROJECTION PROGRAM, AND SERVER DEVICE

(71) Applicant: QD Laser, Inc., Kanagawa (JP)

(72) Inventors: Mitsuru Sugawara, Kanagawa (JP); Makoto Suzuki, Kanagawa (JP); Kinya Hasegawa, Kanagawa (JP)

(73) Assignee: QD Laser, Inc., Kanagawa (JP)

( * ) Notice: Subject to any disclaimer, the term of this patent is extended or adjusted under 35 U.S.C. 154(b) by 0 days.

(21) Appl. No.: 16/306,966

(22) PCT Filed: Jun. 8, 2017

(86) PCT No.: PCT/JP2017/021380
§ 371 (c)(1),
(2) Date: Dec. 4, 2018

(87) PCT Pub. No.: WO2017/213241
PCT Pub. Date: Dec. 14, 2017

(65) Prior Publication Data
US 2019/0137857 A1    May 9, 2019

(30) Foreign Application Priority Data

Jun. 9, 2016  (JP) .................................. 2016-115046
Jun. 5, 2017  (JP) .................................. 2017-111151

(51) Int. Cl.
G03B 21/20    (2006.01)
G02B 27/02    (2006.01)
(Continued)

(52) U.S. Cl.
CPC .......... G03B 21/2033 (2013.01); A61B 3/024 (2013.01); A61B 3/032 (2013.01);
(Continued)

(58) Field of Classification Search
CPC ............... H04N 9/3129; H04N 9/3188; G03B 21/2033; G16H 50/00; A61B 3/032;
(Continued)

(56) References Cited

U.S. PATENT DOCUMENTS 8,042,947 B1 * 10/2011 Eberl ..................... A61B 3/113
351/246
8,814,691 B2 * 8/2014 Haddick .............. G02B 27/017
463/42
(Continued)

FOREIGN PATENT DOCUMENTS

JP    2010-066599    3/2010
JP    2011-215194    10/2011
(Continued)

OTHER PUBLICATIONS

Yasuyuki Murai et al., "Development of the fitting method of HMD (eyesight aid) to support visibility of low vision", The 14th Forum on Information Technology Koen Ronbunshu, Aug. 24, 2015, separate vol. 3, pp. 545 to 546, with partial English translation.
(Continued)

*Primary Examiner* — Jefferey F Harold
*Assistant Examiner* — Mustafizur Rahman
(74) *Attorney, Agent, or Firm* — IPUSA, PLLC

(57) ABSTRACT

A terminal device (300) includes a projection target holding unit that holds projection information to be projected by an image projection device (200), a storage unit that stores position information indicating a position on the retina of a user (P) at which the projection information is to be projected, a position information acquisition unit that acquires the position information from the storage unit, an image data generation unit that generates image data (D) of an image (202G) that projects the projection information at the position indicated by the position information, and an image
(Continued)

output processing unit that outputs the image data (D) to the image projection device (200). The image projection device (200) includes a light source unit that emits a light beam, an image input unit that inputs the image data (D) from the terminal device (300), a control unit that generates an image light beam based on the input image data (D) and controls emission of the image light beam from the light source unit, a scanning mirror that scans the image light beam, and a projection unit that projects the image light beam on the retina of the eyeball of the user (P) as the image (202G) represented by the image data (D).

12 Claims, 48 Drawing Sheets

(51) Int. Cl.
  *G09G 5/38*  (2006.01)
  *G16H 50/00*  (2018.01)
  *A61B 3/024*  (2006.01)
  *A61B 3/032*  (2006.01)
  *H04N 9/31*  (2006.01)
  *G02B 27/01*  (2006.01)
  *G02B 26/12*  (2006.01)
  *G09G 3/02*  (2006.01)

(52) U.S. Cl.
  CPC ........... *G02B 26/12* (2013.01); *G02B 27/017* (2013.01); *G02B 27/02* (2013.01); *G09G 3/025* (2013.01); *G09G 5/38* (2013.01); *G16H 50/00* (2018.01); *H04N 9/3129* (2013.01); *H04N 9/3188* (2013.01); *G09G 2380/08* (2013.01)

(58) Field of Classification Search
  CPC ...... G02B 27/017; G02B 27/02; G09G 3/025; G09G 5/38
  See application file for complete search history.

(56) References Cited

U.S. PATENT DOCUMENTS

| | | | | |
|---|---|---|---|---|
| 9,759,917 | B2* | 9/2017 | Osterhout | G02B 27/0093 |
| 2002/0101568 | A1* | 8/2002 | Eberl | G02B 27/017 351/211 |
| 2004/0061831 | A1* | 4/2004 | Aughey | A61B 3/113 351/209 |
| 2010/0060552 | A1 | 3/2010 | Watanabe et al. | |
| 2011/0128209 | A1* | 6/2011 | Ono | G02B 27/017 345/8 |
| 2011/0158478 | A1* | 6/2011 | Yamada | G02B 6/0006 382/103 |
| 2012/0235886 | A1* | 9/2012 | Border | G02B 27/0093 345/8 |
| 2012/0242560 | A1* | 9/2012 | Nakada | G09G 3/3406 345/8 |
| 2012/0242678 | A1* | 9/2012 | Border | G02B 27/0093 345/589 |
| 2014/0172432 | A1 | 6/2014 | Sendai | |

FOREIGN PATENT DOCUMENTS

| | | |
|---|---|---|
| JP | 2012-108379 | 6/2012 |
| JP | 2014-120963 | 6/2014 |

OTHER PUBLICATIONS

International Search Report for PCT/JP2017/021380 dated Sep. 5, 2017.
Naoyuki Osaka and Koichi Oda, "Effective visual field size necessary for vertical reading during Japanese text processing", Bulletin of the Psychonomic Society, 1991, 29(4), 345-347.

* cited by examiner

| USER ID | VISUAL FIELD | VISUAL ACUITY |
|---------|--------------|---------------|
| 001 | (x1, y1)~(x10, y10), (x15, y15)~(x18, y18) ⋮ | 0.8, 0.7 ⋮ |

| 1 | 2 | 3 | 4 | 5 | 6 | 7 | 8 | 9 | 10 |
|---|---|---|---|---|---|---|---|---|---|
| 11 | 12 | 13 | 14 | 15 | 16 | 17 | 18 | 19 | 20 |
| 21 | 22 | 23 | 24 | 25 | 26 | 27 | 28 | 29 | 30 |
| 31 | 32 | 33 | 34 | 35 | 36 | 37 | 38 | 39 | 40 |
| 41 | 42 | 43 | 44 | 45 | 46 | 47 | 48 | 49 | 50 |
| 51 | 52 | 53 | 54 | 55 | 56 | 57 | 58 | 59 | 60 |
| 61 | 62 | 63 | 64 | 65 | 66 | 67 | 68 | 69 | 70 |
| 71 | 72 | 73 | 74 | 75 | 76 | 77 | 78 | 79 | 80 |
| 81 | 82 | 83 | 84 | 85 | 86 | 87 | 88 | 89 | 90 |
| 91 | 92 | 93 | 94 | 95 | 96 | 97 | 98 | 99 | 100 |

FIG.19

| 1 | 2 | 3 | 4 | 5 | 6 |
|---|---|---|---|---|---|
| 7 | 8 | 9 | 10 | 11 | 12 |
| 13 | 14 | 15 | 16 | 17 | 18 |
| 19 | 20 | 21 | 22 | 23 | 24 |
| 25 | 26 | 27 | 28 | 29 | 30 |
| 31 | 32 | 33 | 34 | 35 | 36 |
| 37 | 38 | 39 | 40 | 41 | 42 |
| 43 | 44 | 45 | 46 | 47 | 48 |

FIG.20

TEST SUBJECT ID = 001　331-P

| TEST DATE | INPUT TIME | UNREADABLE NUMBERS | READABLE NUMBERS |
|---|---|---|---|
| 2016/4/10 | 10:00 | 1, 2, 9-11, 20, 21, 30, 90, 100 | 3-8, 12-19, 22-29, 31-89, 91-99 |
| 2016/4/13 | 18:00 | 1, 2, 9-11, 20, 21, 30, 99, 100 | 3-8, 12-19, 22-29, 31-98 |

TEST SUBJECT ID = 002 — 331-Q

| TEST DATE | INPUT TIME | UNREADABLE NUMBERS | READABLE NUMBERS |
|---|---|---|---|
| 2016/4/10 | 10:00 | 1-4, 11-14, 21-24, 31-34, 41-44, 51-54, 60-100 | 5-10, 15-20, 25-30, 35-40, 45-50, 55-59 |
| 2016/4/13 | 18:00 | 1-4, 11-13, 21-23, 31-33, 41-43, 51-54, 61-100 | 5-10, 14-20, 24-30, 34-40, 44-50, 55-60 |

| TEST SUBJECT ID = 002 | | |
|---|---|---|
| TEST DATE | INPUT TIME | INDISCERNIBLE LANDOLT RINGS | DISCERNIBLE LANDOLT RINGS |
| 2016/4/10 | 10:00 | 1-4, 12-15, 23-26, 34-37, 45-49, 53-66 | 5-11, 16-22, 27-33, 38-44, 50-52 |

| TEST SUBJECT ID = 002 | | | |
|---|---|---|---|
| TEST DATE | INPUT TIME | INDISCERNIBLE AREAS | DISCERNIBLE AREAS |
| 2016/4/10 | 10:00 | (x1, y1)~(x2, y2), (x5, y5)~(x7, y7), (x10, y10)~(x15, y15) | (x3, y3)~(x4, y4), (x8, y8)~(x9, y9) |

| PROJECTION INFORMATION | PROJECTION POSITION |
|---|---|
| INCOMING CALL NOTIFICATION | (x11, y11), (x21, y21) |
| NEW MAIL NOTIFICATION | (x12, y12), (x22, y22) |
| TODAY'S NEWS | (x13, y13), (x23, y23) |

IMAGE PROJECTION SYSTEM, IMAGE PROJECTION DEVICE, IMAGE PROJECTION METHOD, IMAGE PROJECTION PROGRAM, AND SERVER DEVICE

TECHNICAL FIELD

The present invention relates to an image projection system, an image projection device, an image projection method, an image projection program, and a server device.

BACKGROUND ART

Image projection devices employing techniques that involve projecting an image light beam based on image data onto the retina of a person to enable the person to visually perceive an image represented by the image data irrespective of the function of the person's crystalline lens are known.

PRIOR ART DOCUMENTS

Patent Documents

Patent Document 1: Japanese Unexamined Patent Publication No. 2011-215194

SUMMARY OF THE INVENTION

Problem to be Solved by the Invention

In conventional image projection devices, the entire range of an image or picture represented by input image data is projected onto the retina of a person as is. As such, conventional image projection devices are unable to show the entire range of a projected image or picture to a person with a visual field abnormality such as visual field contraction, for example. Thus, when a person with a visual field abnormality wears a conventional image projection device, for example, the person may not be able to visually perceive a portion of a projected image or picture of particular interest to the person.

The disclosed technique has been conceived in view of the above problems of the related art and provides an image projection system, an image projection device, an image projection method, an image projection program, and a server device that can project an image within a visual field of a user.

Means for Solving the Problem

According to one embodiment of the present invention, an image projection system including an image projection device and a terminal device communicating with the image projection device is provided. The terminal device includes a projection target holding unit configured to hold projection information to be projected by the image projection device, a storage unit configured to store position information indicating a position on a retina of a user at which the projection information is to be projected, a position information acquisition unit configured to acquire the position information from the storage unit, an image data generation unit configured to generate image data of an image that projects the projection information at the position indicated by the position information, and an image output processing unit configured to output the image data to the image projection device. The image projection device includes a light source unit configured to emit a light beam, an image input unit configured to input the image data from the terminal device, a control unit configured to generate an image light beam based on the input image data and control emission of the image light beam from the light source unit, a scanning mirror configured to scan the image light beam, and a projection unit configured to project the image light beam onto the retina of the eyeball of the user as the image represented by the image data.

Advantageous Effect of the Invention

According to an aspect of the present invention, an image can be projected within a visual field.

BRIEF DESCRIPTION OF THE DRAWINGS

FIG. 19 is a diagram illustrating a first example of a visual field test image according to the second embodiment;

FIG. 20 is a diagram illustrating a second example of the visual field test image according to the second embodiment;

FIG. 33 is a first diagram illustrating an example of a visual field information table according to the second embodiment;

FIG. 36 is a second diagram illustrating an example of the visual field information table according to the second embodiment;

FIG. 39 is a first diagram illustrating an example of the visual acuity information table according to the second embodiment;

FIG. 40 is a second diagram illustrating an example of the visual acuity information table according to the second embodiment;

EMBODIMENTS FOR IMPLEMENTING THE INVENTION

First Embodiment

Figure 1:
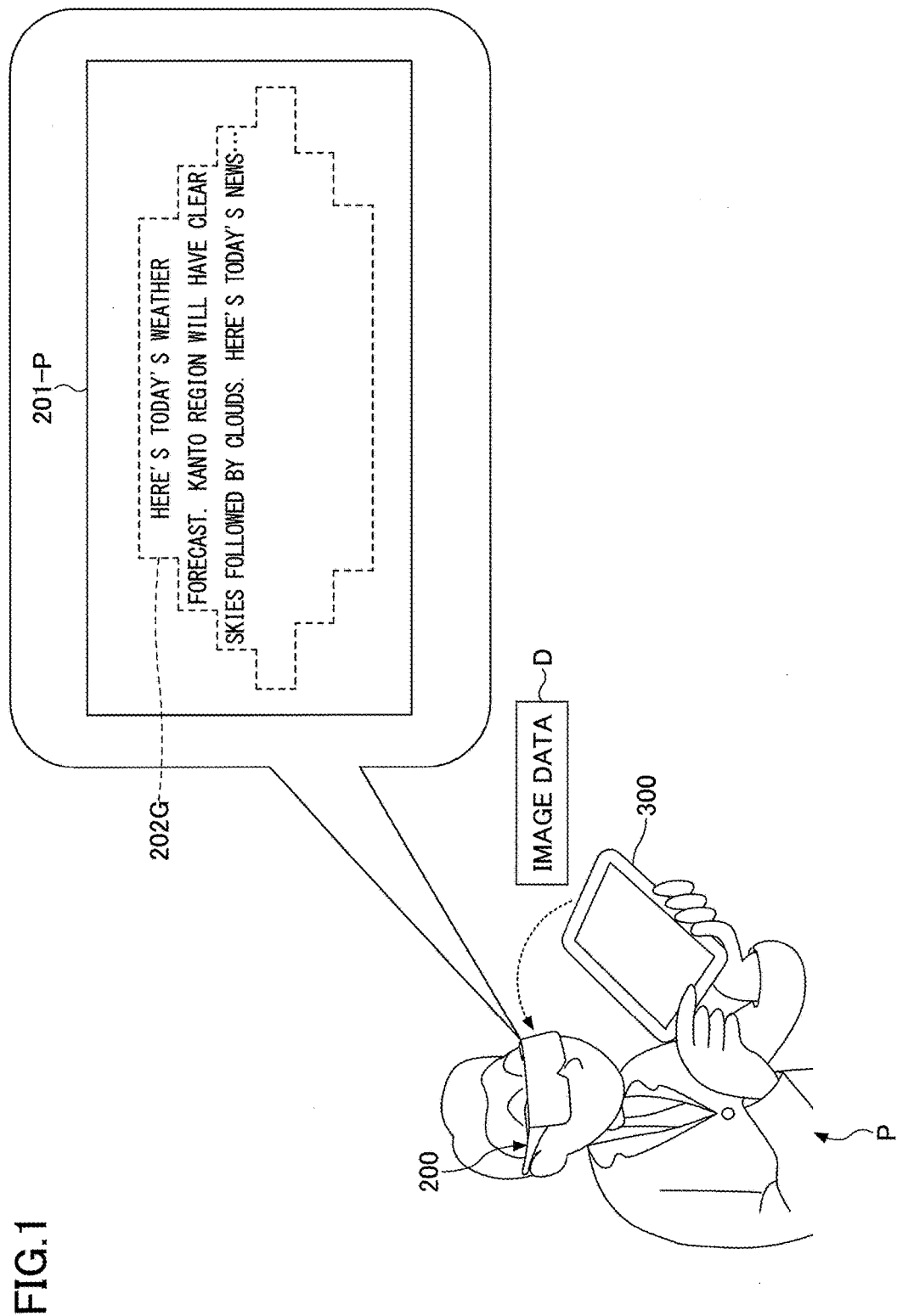
FIG. 1 is a diagram schematically illustrating projection of an image according to a first embodiment of the present invention.

In the following, a first embodiment of the present invention will be described with reference to the drawings. FIG. 1 is a diagram schematically illustrating projection of an image according to the first embodiment.

An image projection system 100 according to the present embodiment includes an image projection device 200 and a terminal device 300.

In the image projection system 100 according to the present embodiment, the terminal device 300 generates image data of an image to be projected onto a visual field of a user P, based on information indicating the visual field of the user P that is wearing the image projection device 200 and projection information, and provides the generated image data to the image projection device 200.

Note that projection information is information corresponding to the base of an image to be projected onto the retina of the user P by the image projection device 200, and may be a symbol, such as a letter, a number, or the like, or an image, for example.

The image projection device 200 according to the present embodiment is a retinal projection head-mounted display using the Maxwellian view. The Maxwellian view refers to a method that involves converging image light beams based on image data at the center of the pupil before projecting the image light beams onto the retina so as to enable a person to view the image represented by the image data without being affected by the function of the person's crystalline lens. The terminal device 300 according to the present embodiment may be a tablet computer, a smartphone, or the like, for example, and transmits image data to the image projection device 200.

The image projection device 200 irradiates image light beams that are based on the image data transmitted from the terminal device 300 onto the retina of the user P to thereby project an image onto the retina of the user P.

If the function of the retina is normal, the image directly projected onto the retina of a person is visually perceived as the image represented by the image data. However, when a person has problems in retinal function, optic nerve, or the like, the image projected on the retina of the person is visually perceived in a manner different from the image represented by the image data.

For example, when a person has a limited visual field due to visual field contraction or the like, only a part of the image projected onto the retina that is within the range of the limited visual field can be visually perceived by the person. In other words, the image projected onto the retina is visually perceived as an image missing part of the image corresponding to the lost visual field.

Taking into account the above aspect, in the present embodiment, information indicating the visual field of the retina of a user is obtained in advance by visual field testing or the like, and an image is projected to the user's visual field based on the information indicating the user's visual field.

For example, when the visual field of the user P is limited, the terminal device 300 may generate image data D for projecting projection information within the visual field of the user P based on information indicating the visual field of the user P, information indicating the visual acuity of the user P, and the projection information, and transmit the generated image data D to the image projection device 200. The image projection device 200 projects an image based on the image data D onto the retina of the user P.

In this way, in the present embodiment, the image projected onto the retina of the user P can be adjusted to be an image 201-P, for example, on which information is projected in a size appropriate for the visual acuity of the user P and within an area corresponding to the visual field of the user P. That is, according to an aspect of the present embodiment, with the above configuration, an image can be projected onto a position that can be visually perceived by a user even when the user has a limited visual field.

In the following, devices included in the image projection system 100 according to the present embodiment will be described with reference to FIG. 2 to FIG. 5.

Figure 2:
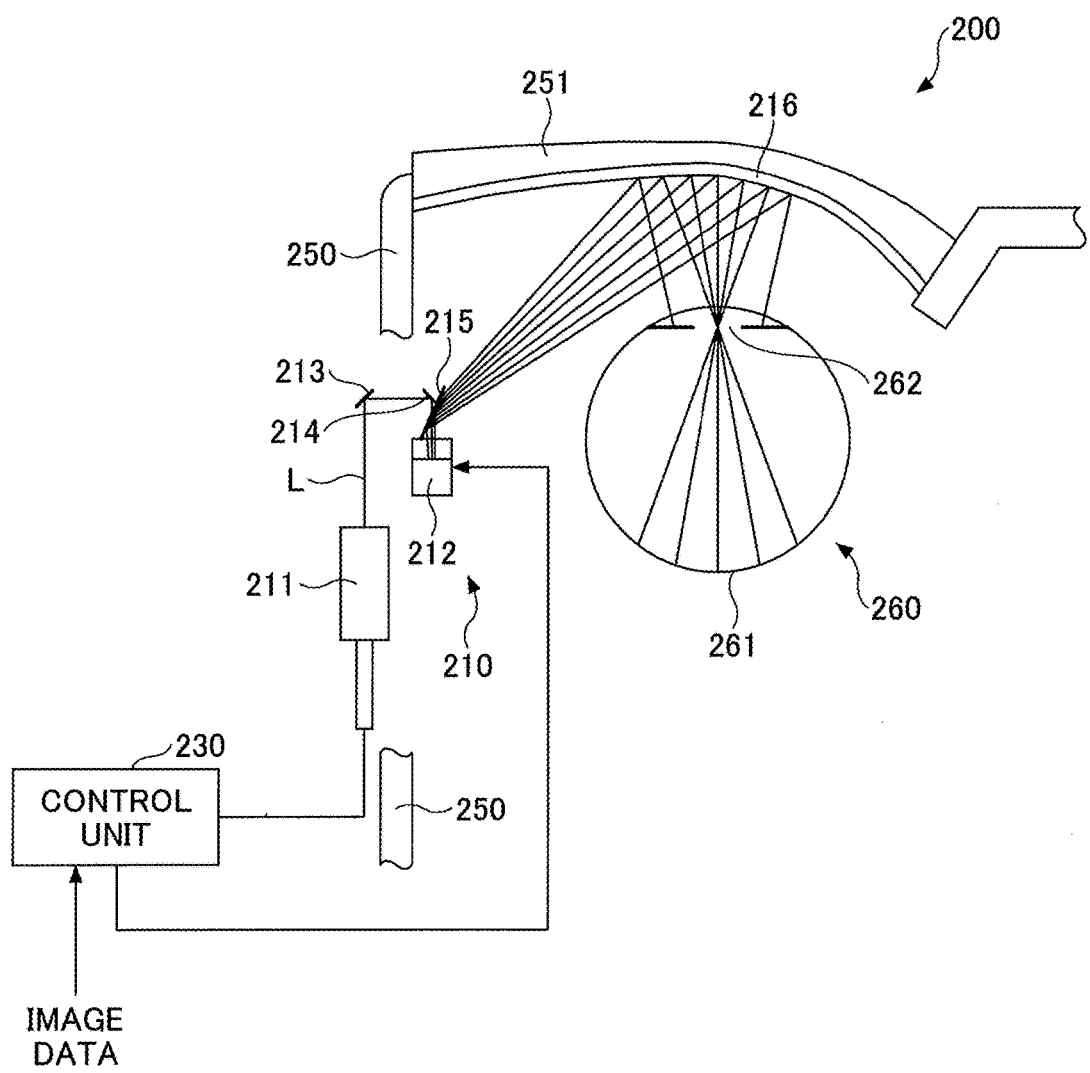
FIG. 2 is a top view of an image projection device.

FIG. 2 is a top view of a visual field testing device. The image projection device 200 according to the present embodiment includes a projection unit 210 and a control unit 230.

The projection unit 210 according to the present embodiment includes a light source 211, a scanning mirror 212, a mirror 213, a mirror 214, a mirror 215, and a projection mirror 216.

The light source 211 is disposed at a temple (arm) 250 of an eyeglass frame. The light source 211 emits a light beam L having a single wavelength or a plurality of wavelengths, for example, under the direction of the control unit 230. This light beam L is an image light beam for projecting an image onto the retina 261 of the eyeball 260 of a user. In the following description, the light beam L is referred to as an image light beam.

The light source 211 may be configured to emit red laser light (wavelength: about 610 nm to 660 nm), green laser light (wavelength: about 515 nm to 540 nm), and blue laser light (wavelength: about 440 nm to 480 nm), for example. The light source 211 according to the present embodiment may be implemented by a light source having laser diode chips of RGB (red, green, blue), a three-color synthesizing device, and a micro collimating lens integrated therein, for example.

The scanning mirror 212 is disposed at the temple 250 of the eyeglass frame. The scanning mirror 212 scans the image light beam emitted from the light source 211 in the horizontal direction and the vertical direction. The scanning mirror 212 may be a MEMS (Micro Electro Mechanical System) mirror, for example. Note that the image light beam emitted from the light source 211 may be reflected by the mirror 213 and the mirror 214 to be incident on the scanning mirror 212, for example.

The control unit 230 according to the present embodiment may be implemented by a processor, such as a CPU (Central Processing Unit), and a memory, such as a RAM (Random Access Memory) and a ROM (Read Only Memory), for example.

The processor and the memory may be mounted on the same substrate as the substrate on which the scanning mirror 212 (MEMS mirror) is mounted, for example. Further, the processor and the memory may be provided in an external device (e.g., the terminal device 300) that is connected to the image projection device 200.

The control unit 230 according to the present embodiment controls the projection unit 210. The control unit 230 causes an image light beam based on input image data to be emitted from the light source 211. Further, the control unit 230 according to the present embodiment causes the scanning mirror 212 (MEMS mirror) to vibrate and scan the image light beam emitted from the light source 211 and cause an image to be projected on the retina 261.

In the following, projection of an image by the projection unit 210 of the image projection device 200 will be described with reference to FIGS. 3 and 4.

Figure 3:
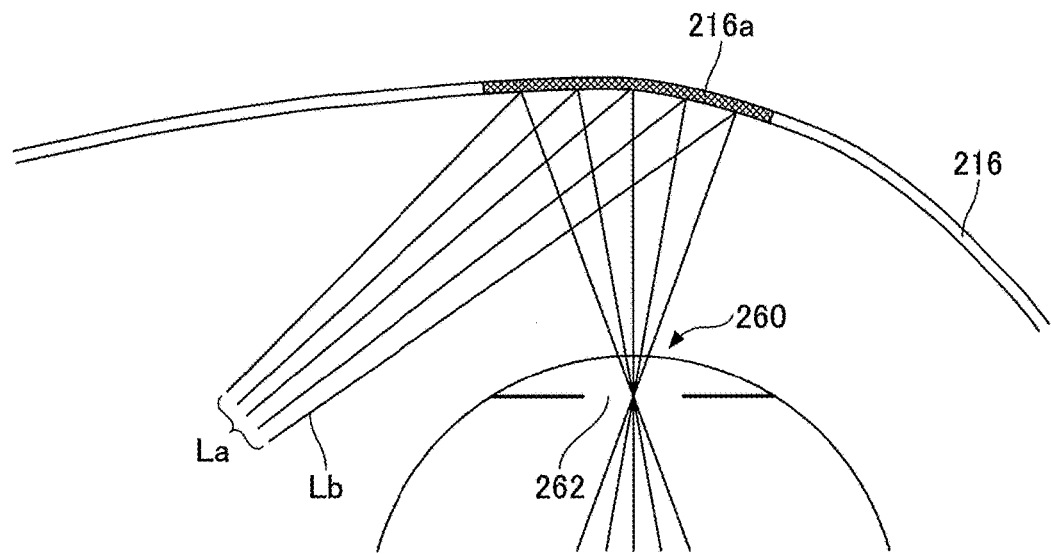
FIG. 3 is an enlarged view of the vicinity of a projection portion of the image projection device.

FIG. 3 is an enlarged view of the vicinity of a projection portion of the image projection device 200.

As shown in FIG. 2 and FIG. 3, the image light beam scanned by the scanning mirror 212 is reflected by the mirror 215 to be directed toward a lens 251 of the eyeglass frame. In the present embodiment, the projection unit 210 is disposed on a face toward the eyeball 260 side of the lens 251, and as such, the image light beam scanned by the scanning mirror 212 is incident on the projection mirror 216.

The projection mirror 216 is a half mirror including an area 216*a* on which the image light beam is incident that may have a free-form surface or a combined structure of a free-form surface and a diffractive surface. In this way, the image light beams incident on the projection mirror 216 converge in the vicinity of the pupil 262 of the eyeball 260 and are then projected onto the retina 261.

Thus, a user can recognize an image formed by the image light beams and can also visually recognize the outside world image in a see-through manner.

Figure 4:
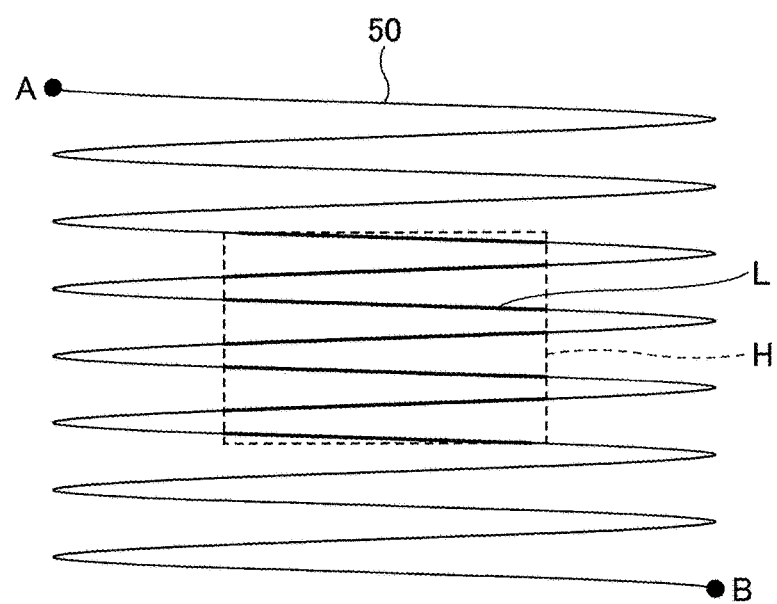
FIG. 4 is a diagram illustrating vibration of a scanning mirror.

FIG. 4 is a diagram illustrating vibration of the first mirror. Note that FIG. 4 illustrates an example case where the scanning mirror 212 moves back and forth from point A to point B.

An example method of scanning an image light beam with the scanning mirror 212 and projecting an image onto the retina 261 includes a method of rapidly scanning light from the upper left to the lower right of an image projection area to thereby display an image (e.g., raster scan).

In the present embodiment, as shown in FIG. 4, in order to scan the image light beam (light beam L), the scanning mirror 212 moves across a larger range in the horizontal direction (first direction) and the vertical direction (second direction intersecting with the first direction) as compared with an image projection area H (a range indicated by broken lines in FIG. 4) to be projected onto the retina 261. In FIG. 4, the movement of the scanning mirror 212 is indicated by reference numeral 50.

In the case where an image is projected onto the retina 261 by scanning the image light beam at a location where deflection of the scanning mirror 212 is substantially large, distortion of the image increases. Thus, in the present embodiment, the image light beam is scanned at a location where the deflection of the scanning mirror 212 is small.

Note that although FIG. 4 illustrates an example case where the image light beams are scanned across a rectangular shape, the present invention is not limited to such a case, and the image light beams may be scanned across a trapezoidal shape or some other shape, for example.

Figure 5:
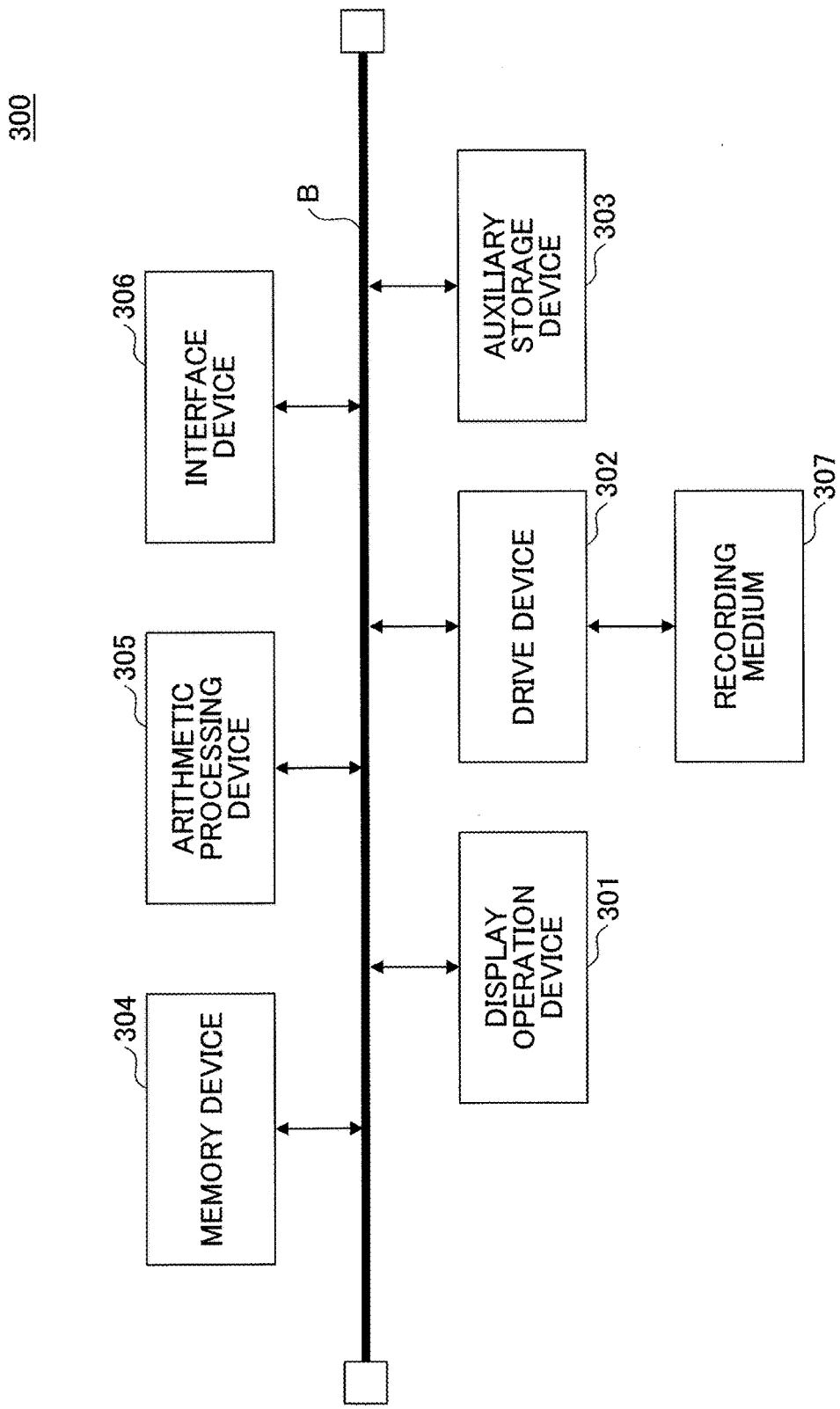
FIG. 5 is a diagram illustrating an example hardware configuration of a terminal device.

In the following, the terminal device 300 according to the present embodiment will be described. FIG. 5 is a diagram illustrating an example hardware configuration of the terminal device 300.

The terminal device 300 according to the present embodiment includes a display operation device 301, a drive device 302, an auxiliary storage device 303, a memory device 304, an arithmetic processing device 305, and an interface device 306 that are connected to each other by a bus B.

The display operation device 301 may be a touch panel or the like, and has a display function for displaying information and an input function for inputting information. The interface device 306 may include a LAN card, for example, and is used for establishing connection with a network.

An image projection program to be executed by the terminal device 300 constitutes at least a part of various programs for controlling the terminal device 300. The image projection program may be recorded in a recording medium 307 and distributed, downloaded from a network, or provided in some other suitable manner. Note that various types of recording media may be used as the recording medium 307 storing the image projection program including a recording medium for optically, electrically or magnetically recording information, such as a CD-ROM, a flexible disk, a magneto-optical disk, and the like; and a semiconductor memory for electrically recording information such as a ROM or a flash memory, for example.

Also, when the recording medium 307 storing the image projection program is loaded in the drive device 302, the image projection program stored in the recording medium 307 may be installed in the auxiliary storage device 303 via the drive device 302. The image projection program that is downloaded from a network may be installed in the auxiliary storage device 303 via the interface device 306.

The auxiliary storage device 303 stores the installed image projection program and stores necessary files, data, and the like. The memory device 304 reads the image projection program from the auxiliary storage device 303 and stores the read image projection program when the terminal device 300 is activated. The arithmetic processing device 305 implements various processes as described below based on the image projection program stored in the memory device 304.

Note that although the terminal device 300 according to the present embodiment includes the display operation device 301, embodiments of the present invention are not limited thereto. For example, the terminal device 300 may be implemented by a desktop computer, a laptop computer, or the like. In such case, instead of including the display operation device 301, the terminal device 300 may include an input device for inputting information, such as a mouse or a keyboard, and an output device such as a display for displaying information.

Figure 6:
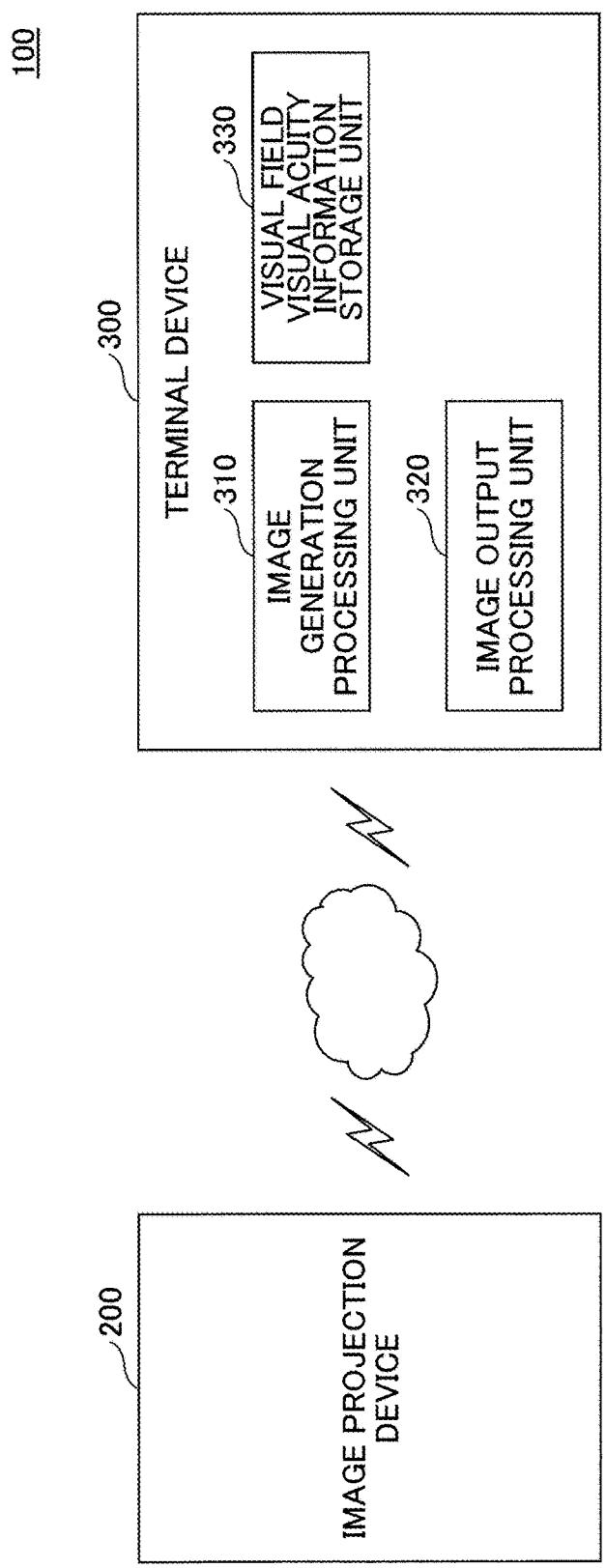
FIG. 6 is a diagram illustrating a system configuration of an image projection system according to the first embodiment.

In the following, the image projection system 100 according to the present embodiment will be described with reference to FIG. 6. FIG. 6 is a diagram illustrating an example system configuration of the image projection system according to the first embodiment.

The image projection system 100 according to the present embodiment includes the image projection device 200 and the terminal device 300. In the image projection system 100, the image projection device 200 is connected to the terminal device 300 and communicates with the terminal device 300.

Note that although the image projection device 200 and the terminal device 300 are configured to communicate wirelessly in the example illustrated in FIG. 6, the present invention is not limited thereto. That is, the image projection device 200 and the terminal device 300 can be connected by any manner as long as they are capable of communicating with each other.

The terminal device 300 according to the present embodiment includes an image generation processing unit 310, an image output processing unit 320, and a visual field visual acuity information storage unit 330.

The image generation processing unit 310 according to the present embodiment refers to the visual field information and the visual acuity information of the user P using the terminal device 300 that are stored in the visual field visual acuity information storage unit 330 and generates image data so that projection information corresponding to information to be projected can be projected onto the user's visual field. Note that the image generation processing unit 310 will be described in detail below.

The projection information may mainly consist of information required by the user or information of interest to the user.

The image output processing unit 320 outputs the image data received from the image generation processing unit 310 to an external device. Specifically, the image output processing unit 320 according to the present embodiment outputs (transmits) the image data received from the image generation processing unit 310 to the image projection device 200.

The visual field visual acuity information storage unit 330 stores information indicating the visual field of the user P and information indicating the visual acuity of the user P using the image projection device 200.

In the present embodiment, information indicating the visual field is information indicating areas of the retina of the user P, i.e., information indicating areas of the retina of the user P that can be visually perceived by the user P when an image is projected thereon. Further, the information indicating the visual acuity according to the present embodiment is information indicating the visual acuity of the retina itself. Specifically, the information indicating the visual acuity according to the present embodiment indicates the macular function of the retina as opposed to general visual acuity that can change through adjustment of the thickness of the crystalline lens by the ciliary muscle or the like, for example. Note that the visual field visual acuity information storage unit 330 will be described in detail below.

Figures 7, 8:
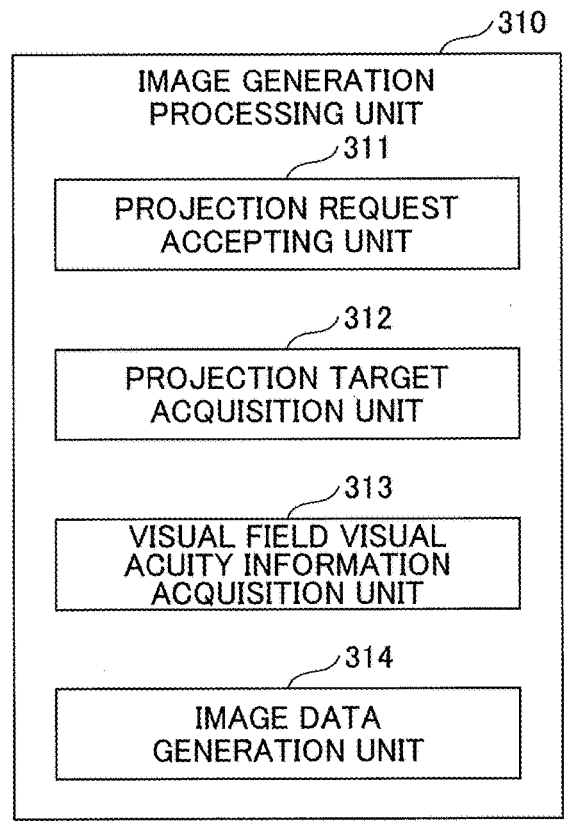
FIG. 7 is a diagram illustrating example functions of an image generation processing unit according to the first embodiment.
FIG. 8 is a diagram illustrating an example of a visual field visual acuity information storage unit according to the first embodiment.

In the following, the image generation processing unit 310 according to the present embodiment will be described with reference to FIG. 7. FIG. 7 is a diagram illustrating functions of the image generation processing unit according to the first embodiment.

The image generation processing unit 310 according to the present embodiment includes a projection request accepting unit 311, a projection target acquisition unit 312, a visual field visual acuity information acquisition unit 313, and an image data generation unit 314.

The projection request accepting unit 311 accepts a projection request for projecting input projection information at the display operation device 301 or the like.

The projection target acquisition unit 312 acquires projection information. The projection information may be content data stored in the auxiliary storage device 303 of the terminal device 300, or content data acquired by the terminal device 300 from an external server, an external storage device, or the like, for example. Also, the projection information may be text data or image data including a moving image, for example. Further, the image projection device 200 according to the present embodiment includes a built-in image capturing device, and the projection information may bean image captured by the built-in image capturing device of the image projection device 200, for example.

The visual field visual acuity information acquisition unit 313 acquires the visual field information of the user P and the visual acuity information of the user P using the image projection device 200 from the visual field visual acuity information storage unit 330. In other words, the visual field visual acuity information acquisition unit 313 is a position information acquisition unit that acquires information indicating the position where the projection information is to be projected.

The image data generation unit 314 generates image data of an image displaying the projection information based on visual field information and passes the generated image data to the image output processing unit 320.

In the following, the visual field visual acuity information storage unit 330 according to the present embodiment will be described with reference to FIG. 8. FIG. 8 is a diagram showing an example of the visual field visual acuity information storage unit according to the first embodiment.

The visual acuity information storage unit 330 according to the present embodiment manages visual field information and visual acuity information in association with a user ID in a table.

The visual field visual acuity information storage unit 330 according to the present embodiment includes "user ID", "visual field", and "visual acuity" as items of information and stores the visual field and the visual acuity of a user in association with the user ID of the user. The value of the item "user ID" is identification information for identifying the user. Note that in the present embodiment, the name of the user or the like may be used as the information for identifying the user instead of an ID of the user, for example. In the present embodiment, the value of the item "visual field" associated with a user ID is referred to as visual field information, and the value of the item "visual acuity" associated with a user ID is referred to as visual acuity information.

The value of the item "visual field" is coordinate information indicating the visual field of the user. The value of the item "visual acuity" indicates the visual acuity of the retina of the user.

Note that although the visual field information and the visual acuity information are not associated with each other in the example illustrated in FIG. 8, the visual field information and the visual acuity information may be associated with each other in the visual field visual acuity information storage unit 330. Specifically, for example, an area indicated by the visual field information and visual acuity information indicating the visual acuity for this area may be stored in association with each other in the visual field visual acuity information storage unit 330.

Also, the visual acuity information according to the present embodiment may be information indicating general visual acuity measured using the Landolt ring, for example.

In the following, the visual field information according to the present embodiment will be described with reference to FIG. 9.

Figure 9:
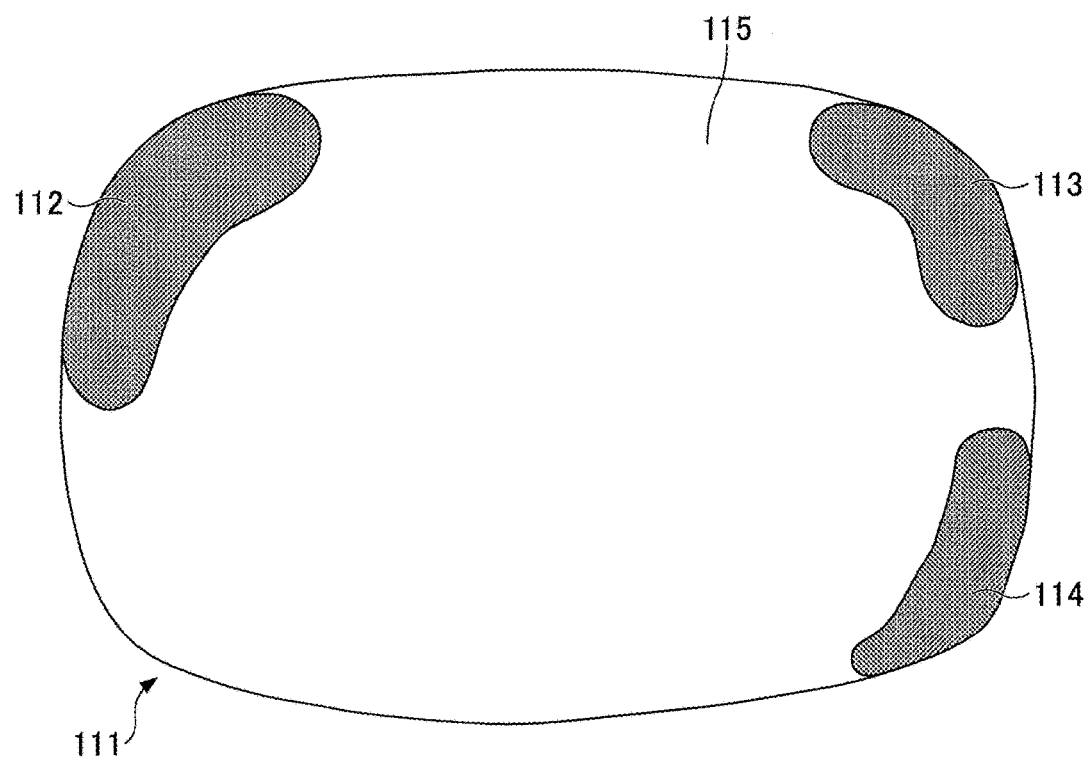
FIG. 9 is a first diagram illustrating an example visual field.

FIG. 9 is a first diagram illustrating an example visual field. As shown in FIG. 9, a visual field 111 of the user P includes defective areas 112, 113, and 114. That is, there is some abnormality in the retina of the user P at positions corresponding to the defective areas 112, 113, and 114.

When an entire image including the projection information is projected onto the retina of a user having a visual field with defective areas as described above, the defective areas 112, 113, and 114 shown in FIG. 9 will be reflected in the projected image. Thus, by projecting information required by the user P or information of interest to the user P onto an area other than the defective area, the information required by the user P or the information of interest to the user P may be visually perceived by the user P even if the user P has a visual field with a defective area.

The information to be projected onto the defective area may be an image that is continuous with the image projected onto the area other than the defective area or a single color image, for example. Alternatively, no image light beam projected onto the defective area.

Accordingly, in the present embodiment, information indicating an area 115 of the retina of a user from which the user can be visually perceive a projected image is stored in the visual field visual acuity information storage unit 330 as coordinate information indicating the visual filed of the user (as the value of the item "visual field" in FIG. 8).

In the present embodiment, the information indicating the visual field of the user may be obtained, for example, by importing an image representing a test result indicating the presence/absence of a visual field defect obtained from a general kinetic visual field test or static visual field test (e.g., visual field test using a Humphrey perimeter), and converting an area with a visual field defect and an area with no visual field defect into the coordinate information. The kinetic visual field test may be a visual field test using a Goldman perimeter, for example, and the static visual field test may be a visual field test using a Humphrey perimeter, for example.

The visual field visual acuity information storage unit 330 according to the present embodiment may be recorded on a portable recording medium, and the terminal device 300 may read the visual field visual acuity information storage unit 330 from such a recording medium, for example. Also, the visual field visual acuity information storage unit 330 may be downloaded from an external server via a network, for example. Note that in the present embodiment, the manner in which the terminal device 300 acquires the visual field visual acuity information storage unit 330 is not particularly limited as long as the terminal device 300 can refer to the visual field visual acuity information storage unit 330. As such, the visual field visual acuity information storage unit 330 may also be stored in an external device that is capable of communicating with the terminal device 300, for example.

Figure 10:
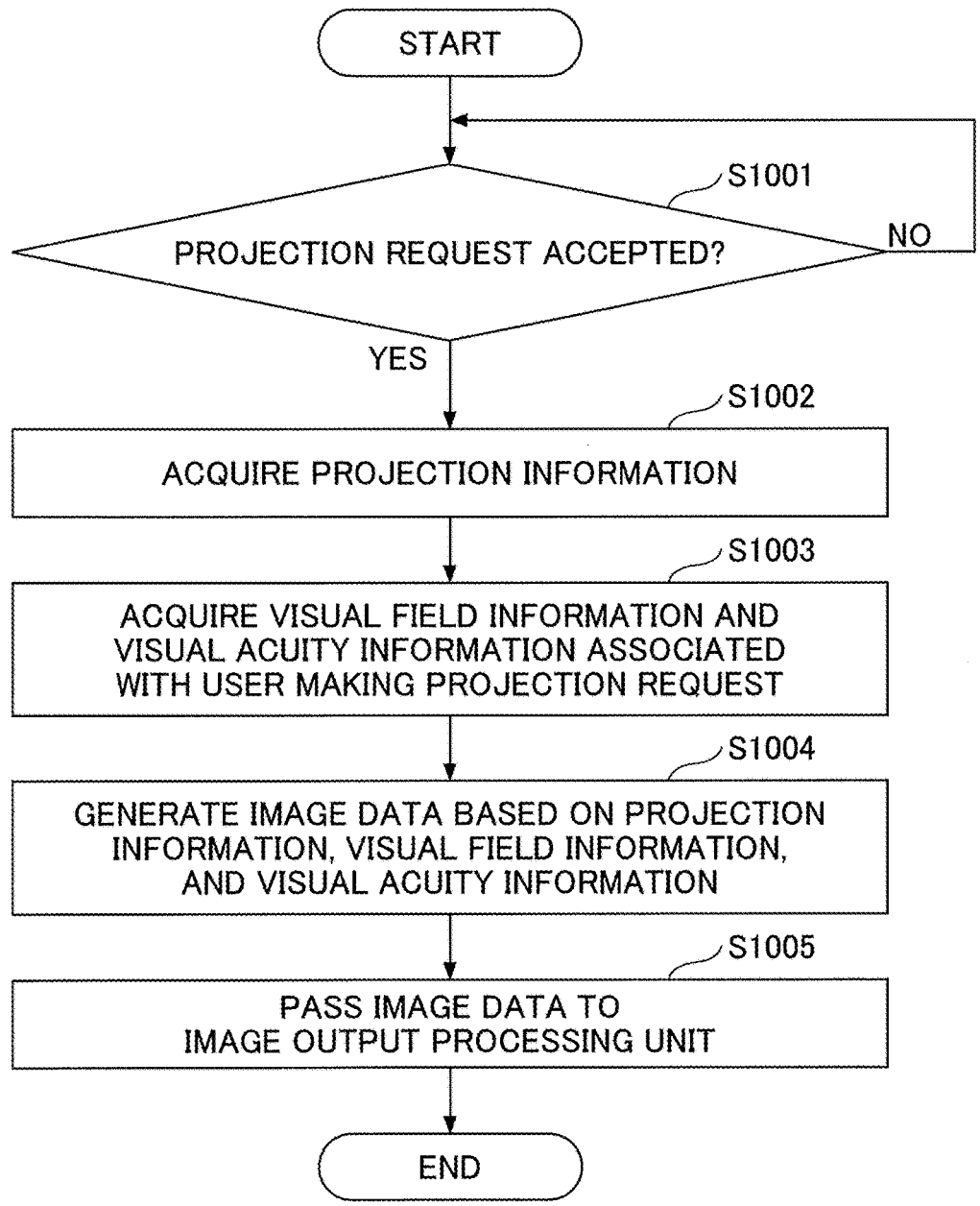
FIG. 10 is a flowchart illustrating example process operations of the image generation processing unit according to the first embodiment.

In the following, processing of the image generation processing unit 310 according to the present embodiment will be described with reference to FIG. 10. FIG. 10 is a flowchart illustrating the process operations of the image generation processing unit according to the first embodiment.

The projection request accepting unit 311 of image generation processing unit 310 according to the present embodiment determines whether a selection of projection information and a projection request has been accepted (step S1001). In step S1001, if a projection request is not accepted, the image generation processing unit 310 waits until a projection request is accepted.

When it is determined that a projection request has been accepted in step S1001, the projection target acquisition unit 312 of the image generation processing unit 310 acquires the selected projection information (step S1002).

Then, the visual field visual acuity information acquisition unit 313 of the image generation processing unit 310 acquires the visual field information and the visual acuity information of the user that has made the projection request from the visual field visual acuity information storage unit 330 (step S1003).

Then, the image data generation unit 314 of the image generation processing unit 310 generates image data to be passed to the image output processing unit 320 based on the projection information, the visual field information, and the visual acuity information (step S1004).

Then, the image data generation unit 314 passes the generated image data to the image output processing unit 320 (step S1005) and ends the process.

In the following, image data generated by the image generation processing unit 310 according to the present embodiment will be described with reference to FIG. 11.

Figure 11:
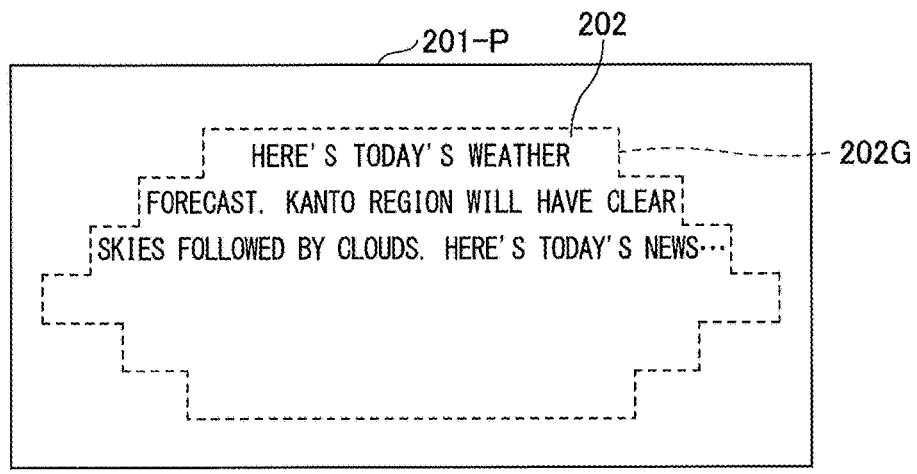
FIG. 11 is a first diagram illustrating an example of image data generated by the image generation processing unit.

FIG. 11 is a first diagram showing an example of image data generated by the image generation processing unit. FIG. 11 illustrates an example case where the image generation processing unit 310 generates image data by referring to the visual field information and the visual acuity information of the user P having the visual field as shown in FIG. 8.

The image generation processing unit 310 generates image data including projection information within the area 115 representing the visual field of the user P.

The image 201-P shown in FIG. 11 is an image having projection information 202 included within the area 115 indicated by the visual field information stored in the visual field visual acuity information storage unit 330. Note that the size of characters representing the projection information 202 is set to an appropriate size according to the visual acuity information stored in the visual field visual acuity information storage unit 330.

The image generation processing unit 310 according to the present embodiment generates image data representing the image 201-P and causes the image projection device 200 to project the image 201-P onto the retina of the user P. According to an aspect of the present embodiment, by generating the image 201-P in this manner, the projection information 202 specified by the user P in a projection request can be projected within the visual field of the user P in a size appropriate for the visual acuity of the user P.

Note that although the image data generation unit 314 according to the present embodiment generates image data of the image 201-P that includes information to be projected only onto the visual field of the user, the present invention is not limited thereto.

For example, the image generation processing unit 310 may generate image data of an image indicating the projection information itself and transmit the image data together with the visual field information to the image projection device 200.

The control unit 230 of the image projection device 200 may adjust the projection position of the image by controlling the vibration of the scanning mirror 212 based on the visual field information and project the image indicating the projection information itself within the visual field of the user.

Specifically, the image generation processing unit 310 may generate image data of an image 202G indicating the projection information 202 itself and cause the image output processing unit 320 to output the image data of the image 202G together with the visual field information to the image projection device 200.

In this case, the image projection device 200 may adjust the projection position of the image by controlling the vibration of the scanning mirror 212 based on the visual field information, and project the image data of the image 202G onto the area indicated by the visual field information.

Figure 12:
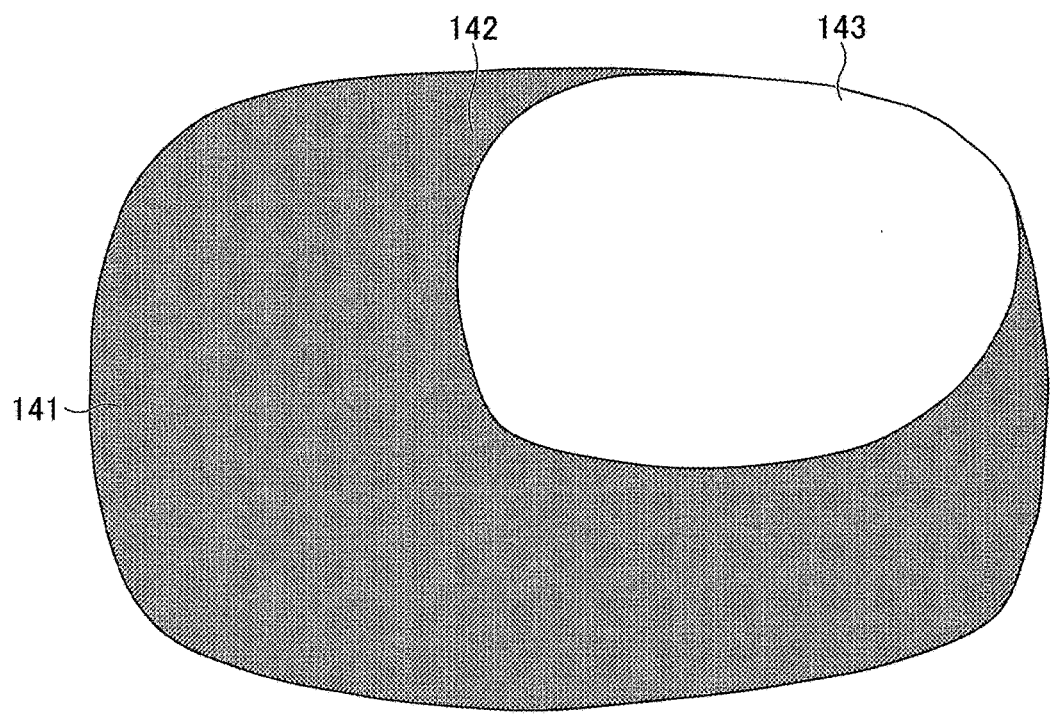
FIG. 12 is a second diagram illustrating an example visual field.

In the following, other examples will be described with reference to FIGS. 12 to 14. FIG. 12 is a second diagram showing an example visual field.

FIG. 12 shows a visual field 141 of user Q. As can be appreciated from FIG. 12, the visual field 141 includes a defective area 142. That is, there is some abnormality in the retina of the user Q at the position corresponding to the defective area 142. As such, a portion of a projected image projected onto a position on the retina corresponding to the defective area 142 (shaded portion) will be visually perceived by the user Q as a missing image portion. In other words, a portion of the image projected onto a position on the retina of the user Q corresponding to an area 143 other than the defective area 142 can be visually perceived by the user Q.

Figure 13:
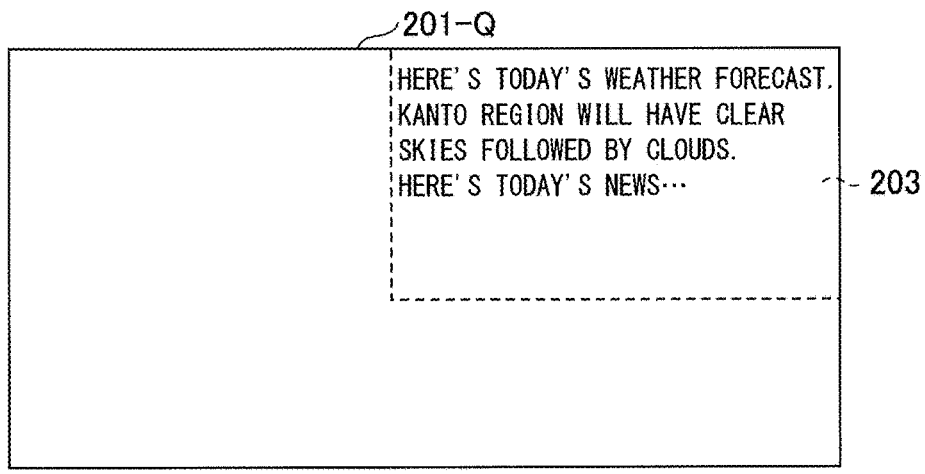
FIG. 13 is a second diagram illustrating an example of image data generated by the image generation processing unit.

FIG. 13 is a second diagram showing an example of image data generated by the image generation processing unit. FIG. 13 illustrates an example case where the image generation processing unit 310 has generated image data by referring to the visual field information and the visual acuity information of the user Q having the visual field as shown in FIG. 12.

The image generation processing unit 310 generates image data of an image 201-Q that includes projection information 203 within the area 143 indicating the visual field of the user Q.

The image 201-Q shown in FIG. 13 is an image having the projection information 203 included within the area 143 indicated by the visual field information of the user Q.

The image generation processing unit 310 according to the present embodiment generates image data representing the image 201-Q and causes the image projection device 200 to project the image 201-Q onto the retina of the user Q. According to an aspect of the present embodiment, by generating the image 201-Q in the above-described manner, the projection information 203 that has been specified by the user Q in a projection request can be projected within the visual field of the user Q.

Figure 14:
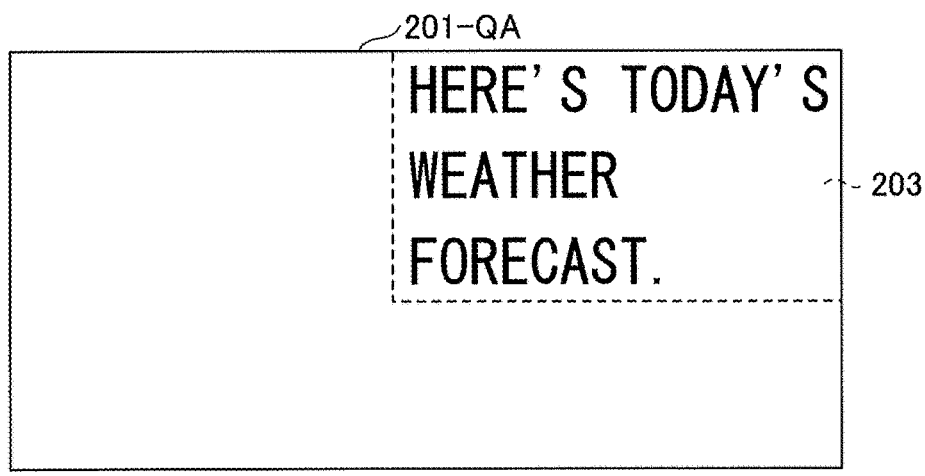
FIG. 14 is a third diagram illustrating an example of image data generated by the image generation processing unit.

FIG. 14 is a third diagram showing an example of image data generated by the image generation processing unit. FIG. 14 shows an image 201-QA that has been generated by the image generation processing unit 310 in a case where the visual acuity of the user Q is worse than the example case shown in FIG. 13.

In the image 201-QA, the characters representing the projection information 203 is in a larger size than the size of the characters representing the projection information 203 in the image 201-Q.

As described above, according to an aspect of the present embodiment, the size of letters, images, symbols, and the like be projected on the retina of the user may be changed according to the visual acuity of the user.

Figure 15:
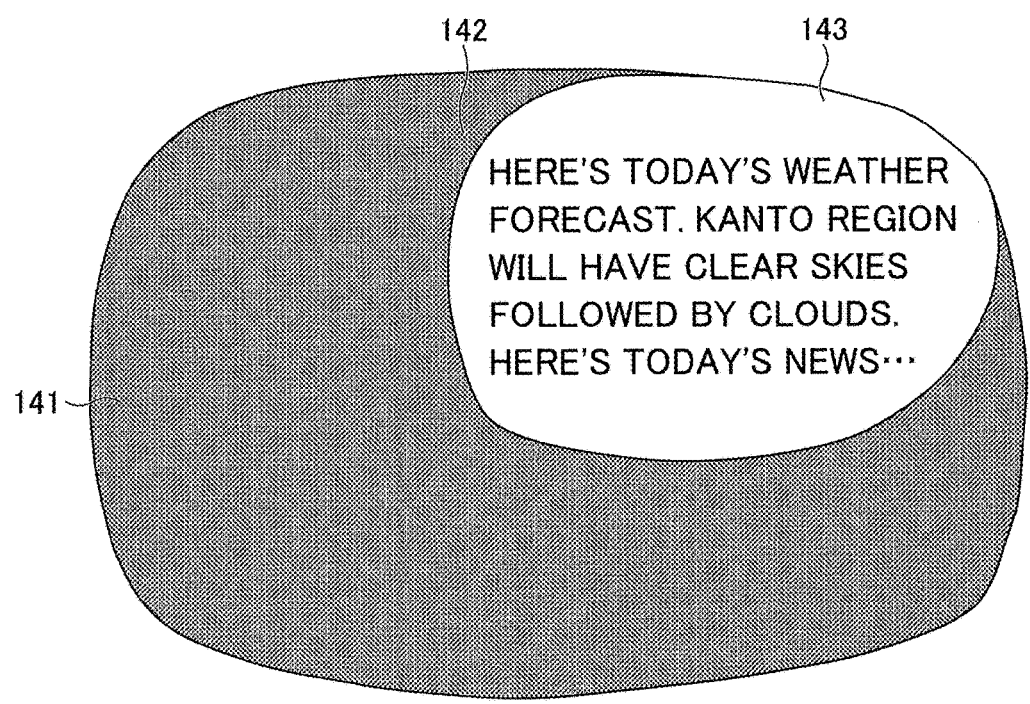
FIG. 15 is a first diagram illustrating an example of how projection information according to the first embodiment is visually perceived.

In the following, how the projection information is visually perceived will be described with reference to FIGS. 15 and 16. FIG. 15 is a first diagram showing an example of how the projection information according to the first embodiment is visually perceived.

FIG. 15 shows how the projection information is visually perceived in the case where the image 201-Q is projected onto the retina of the user Q having the visual field as shown in FIG. 12.

In this case, the image 201-Q is projected onto a position on the retina of the user Q corresponding to the area 143 that is not impaired, and as such, the user Q will be able to visually perceive the projection information 203.

Figure 16:
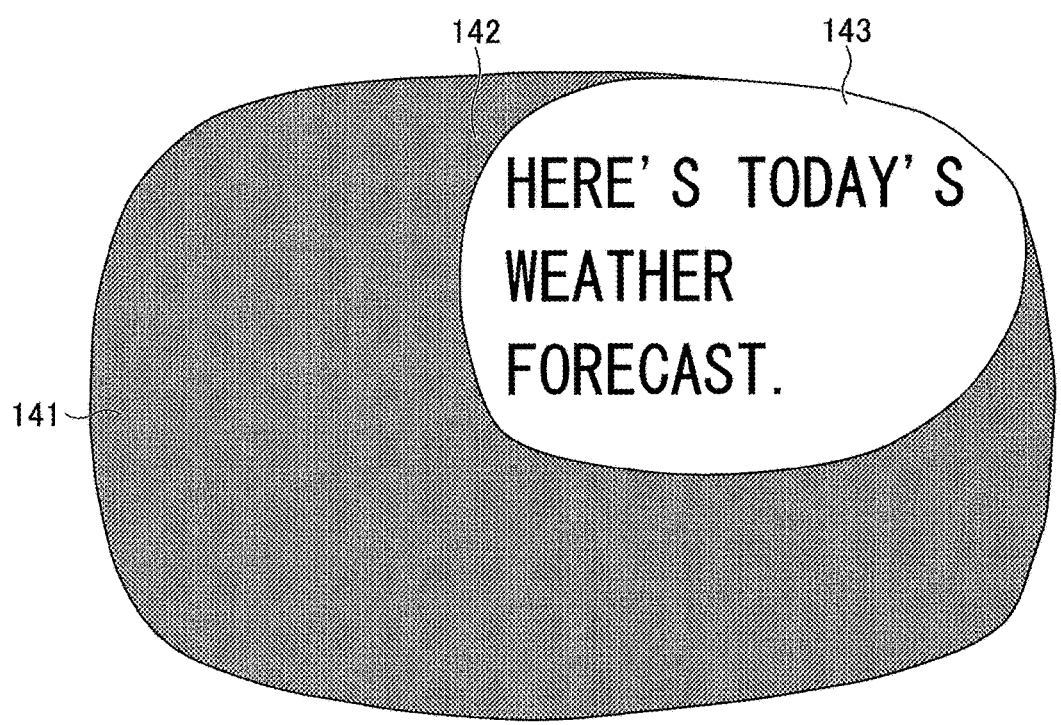
FIG. 16 is a second diagram illustrating an example of how projection information according to the first embodiment is visually perceived.

FIG. 16 is a second diagram showing an example of how the projection information according to the first embodiment is visually perceived. FIG. 16 shows how the projection information is visually perceived in the case where the image 201-QA is projected onto the retina of the user Q having the visual field as shown in FIG. 12. In the image 201-QA, the characters representing the projection information 203 is enlarged according to the visual acuity information of the user Q.

As described above, according to an aspect of the present embodiment, even when there is a defect in the visual field of a user, for example, the projection information 203 can be projected onto an area of the visual field that can be visually perceived by the user according to the visual acuity of the user.

As described above, according to an aspect of the present embodiment, by using test results of a visual field test, information required by a user or information of interest to the user can be projected within the visual field of the user that is using the image projection device 200.

Thus, according to an aspect of the present embodiment, projection information may be projected onto the retina of a user while avoiding loss of the projection information due to visual field loss.

For example, according to an aspect of the present embodiment, when a person having a limited visual field searches for a term in an electronic dictionary or the like, only an image of a portion displaying the meaning of the term or the like may be extracted from the image displaying the search result of the searched term, and the extracted image may be displayed within the visual field of the user so that even a person having a limited visual field may be able to use a normal electronic dictionary.

Also, clinical results have revealed that even a person having a limited visual field can "read" if, in the case of Japanese, at least five characters can be placed in the visual field of the person. Note that the term "reading" as used herein means following characters with the eyes and understanding the meaning thereof (see Osaka, N. & Oda, K. (1991). Effective visual field size necessary for vertical reading during Japanese text processing. Bulletin of the Psychonomic Society, 29(4), 345-347.).

Thus, according to an aspect of the present embodiment, for example, even a person having a visual field with a large defective area and difficulty reading may be able to read text by having at least five characters projected within the visual field of the person.

Note that image data generated by the image generation processing unit 310 according to the present embodiment may also include moving image data. For example, in the case of projecting the content of an electronic book onto the visual field of the user, moving image data may be projected so that text data moves across the visual field of the user.

Also, the control unit 230 of the image projection device 200 may adjust the projection position of an image by controlling the vibration of the scanning mirror 212 based on the visual field information of a user to project the image indicating the projection information itself within the visual field of the user.

Second Embodiment

In the following, a second embodiment of the present invention will be described. The second embodiment differs from the first embodiment in that the visual field information is the test result of a visual field test performed using the image projection device 200. As such, in the following description of the second embodiment, features that differ from those of the first embodiment will be described, and features having substantially the same functional configuration as the first embodiment will be given the same reference numerals and their descriptions will be omitted.

Figure 17:
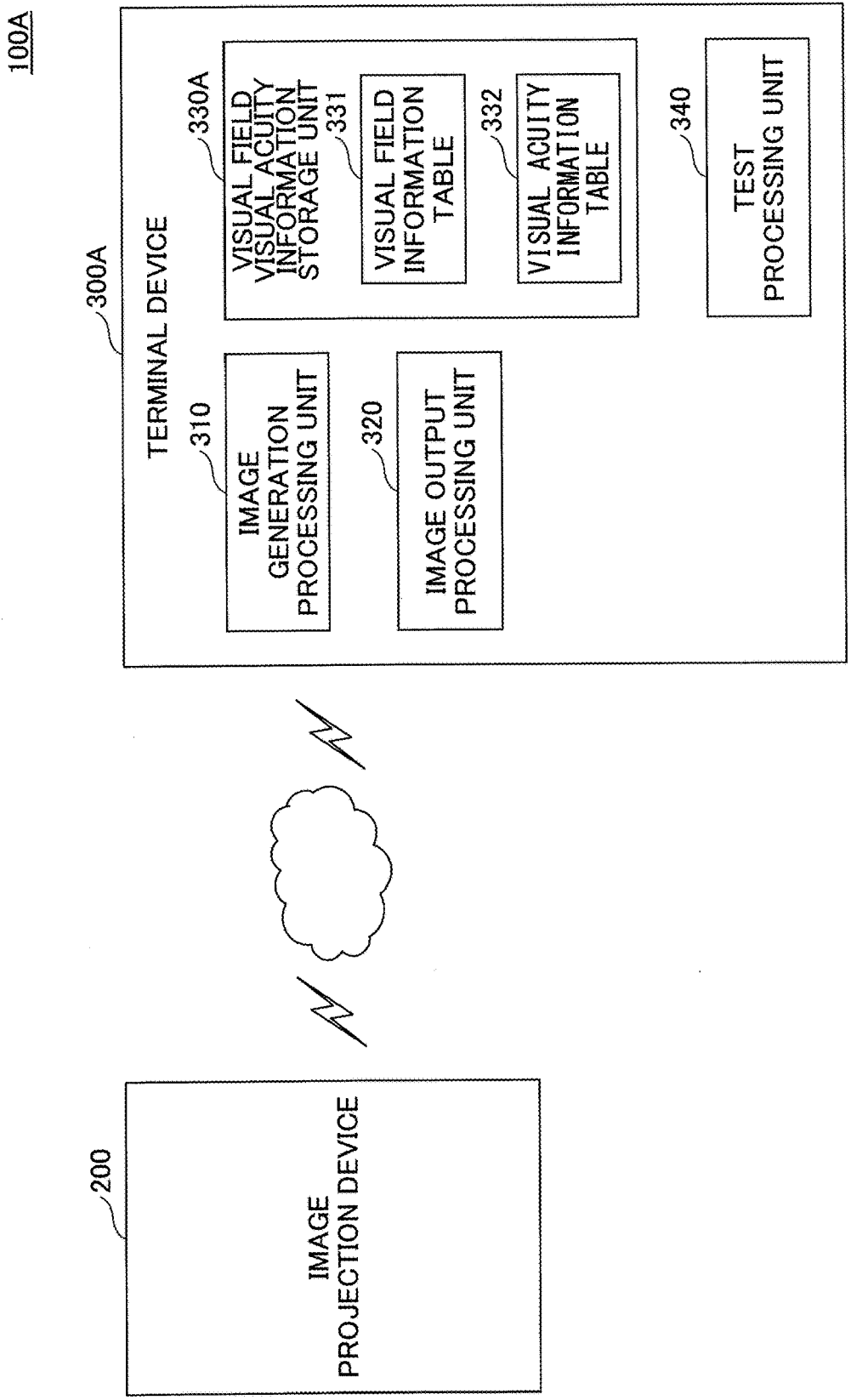
FIG. 17 is a diagram illustrating an example system configuration of an image projection system according to a second embodiment of the present invention.

FIG. 17 is a diagram illustrating an example system configuration of the image projection system according to the second embodiment.

The image projection system 100A according to the present embodiment includes an image projection device 200 and a terminal device 300A.

The terminal device 300A according to the present embodiment includes an image generation processing unit 310, an image output processing unit 320, a visual field visual acuity information storage unit 330A, and a test processing unit 340.

The test processing unit 340 according to the present embodiment holds the test image data corresponding to a visual field test image G and passes the test image data to the image output processing unit 320. Also, the test processing unit 340 according to the present embodiment displays the visual field test image G on the display operation device 301 of the terminal device 300A, receives a test result input by the user, and outputs the test result to the visual field visual acuity information storage unit 330A. Note that the test processing unit 340 will be described in detail below.

The visual field visual acuity information storage unit 330A according to the present embodiment includes a visual field information table 331 and a visual acuity information table 332. The visual field information table 331 stores the test result of the visual field test that has been conducted on the user that has worn the image projection device 200. The visual acuity information table 332 stores the test result of the visual acuity test that has been conducted on the user that has worn the image projection device 200. Note that the visual field information table 331 and the visual acuity information table 332 will be described in detail below.

Figure 18:
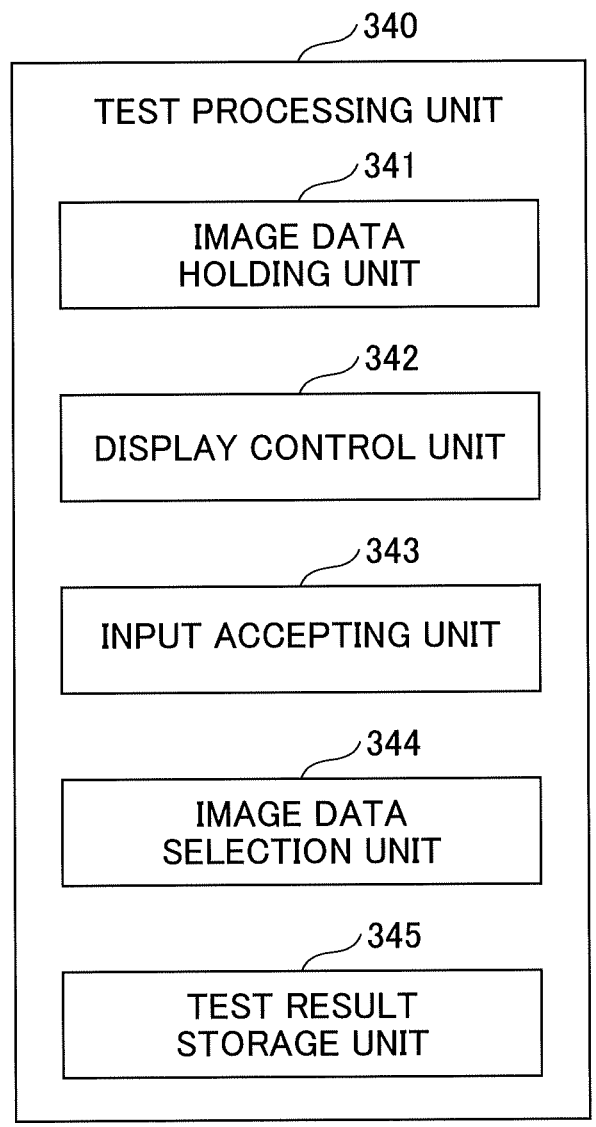
FIG. 18 is a diagram illustrating a test processing unit according to the second embodiment.

In the following, the test processing unit 340 according to the present embodiment will be described with reference to FIG. 18. FIG. 18 is a diagram showing an example functional configuration of the test processing unit according to the second embodiment. Note that the functional elements shown in FIG. 18 may each be implemented by the arithmetic processing device 305 of the terminal device 300A reading out and executing a visual field test program stored in the memory device 304, for example.

The test processing unit 340 according to the present embodiment includes an image data holding unit 341, a display control unit 342, an input accepting unit 343, an image data selection unit 344, and a test result storage unit 345.

The image data holding unit 341 holds visual filed test image data corresponding to the visual field test image G and visual acuity test image data corresponding to a visual acuity test image T. Upon accepting a test start request, the image data holding unit 341 according to the present embodiment passes relevant test image data corresponding to the test to be executed to the image output processing unit 320 and the display control unit 342.

Note that although the image data holding unit 341 is configured to hold the test image data in the image projection system 100A according to the present embodiment, the present invention is not limited thereto. For example, the test image data may also be held by the control unit 230 of the image projection device 200.

Upon receiving the test image data, the display control unit 342 causes the display operation device 301 of the terminal device 300A to display a test result input screen including the test image. More specifically, the display control unit 342 may display a test result input screen including the visual field test image G or a test result input screen including the visual acuity test image T. Also, the display control unit 342 according to the present embodiment may display a selection screen for selecting the visual field test or the visual acuity test in response to accepting a test start request, for example.

The input accepting unit 343 accepts inputs according to various operations performed on the display operation device 301. Specifically, the input accepting unit 343 may accept a test start request and an input to the test result input screen, for example.

The image data selection unit 344 selects test image data corresponding to the type of test specified in the test start request accepted by the input accepting unit 343 from among the test image data held by the image data holding unit 341 and delivers the selected test image data to the display control unit 342.

The test result storage unit 345 stores a test result accepted by the input accepting unit 343 in the visual field visual acuity information storage unit 330A in association with a corresponding user ID and information indicating the date and time the input of the test result was accepted.

In the following, the visual field test image G according to the present embodiment will be described with reference to FIGS. 19 and 20. FIG. 19 is a diagram showing a first example of the visual field test image according to the second embodiment, and FIG. 20 is a diagram showing a second example of the visual field test image according to the second embodiment.

The visual field test image G shown in FIG. 19 is vertically and horizontally divided into a plurality of regions. In other words, the visual field test image G is made up of a group of rectangular regions.

Each region of the visual field test image G has a number inscribed therein as an identifier for identifying the region. Note, however, that the identifier for identifying the region is not limited to a number. For example, a hiragana character, a kanji character, a letter of the alphabet, or a character/letter of some other language may be used as the identifier of the region.

Also, in the visual field test image G, a fixation point M is formed at a center portion. In the example of FIG. 19, the mark "+" is used as a mark indicating the fixation point M. However, the shape of the mark indicating the fixation point is not limited this example. That is, the shape of the mark indicating the fixation point may be any shape as long as it can indicate to the user P the point to which the user P should fix his/her gaze.

Among the various types of visual impairments, in some types of visual impairments, a person may be able to distinguish images but not characters. According to an aspect of the present embodiment, a character may be used as the identifier of each region of the test image so that the ability to recognize each character indicated in each region can be determined, for example.

Note that although the above-described effect can be achieved by using a character as the identifier of each region in the present embodiment, the identifier does not necessarily have to be a character. For example, an image may be displayed in each region as the identifier of the region.

For example, in the visual field test image shown in FIG. 19, an image of an apple may be displayed in the region with the identifier "1", and an image of a car may be displayed in the region with the identifier "2". Also, for example, an image of a star-shaped mark may be displayed in the region with the identifier "1", and an image of a heart-shaped mark may be displayed in the area with the identifier "2", for example.

By using an image rather than a character as the identifier of each region as described above, for example, the visual field test image may be used even with respect to a user that does not have the ability to recognize characters to determine regions that are visible to the user and regions that are not visible to the user.

Note that although the visual field test image G shown in FIG. 19 includes 100 regions, the number of regions included in the visual field test image G is not limited thereto. The number of regions in the visual field test image G may be determined according to the size of the area onto which the visual field test image G is to be projected. Also, the number of regions in the visual field test image G may be adjusted so that regions that are visible to a user and regions that are not visible to the user can be determined.

When the number of regions included in the visual field test image G is too large, the visual field test may be burdensome to the user, and if the number of regions is too small, regions that are visible to the user and regions that are not visible to the user may not be properly determined. As such, in the present embodiment, the number of regions in the visual field test image G is preferably set up so that regions visible to the user and regions not visible to the user can be properly determined without unduly increasing the burden on the user. For example, the number of regions may be determined in advance based on results of repeatedly performing visual field tests using the image projection system 100A according to the present embodiment.

Note that although the regions included in the visual field test image G according to the present embodiment are rectangular regions, the present invention is not limited thereto. For example, the shape of the regions included in the visual field test image G may be circular, elliptical, or square.

FIG. 20 shows a visual field test image G1 that has identifiers in different sizes inscribed in its regions; i.e., the greater the distance of a region from the fixation point M at the center, the larger the size of the identifier inscribed in the region.

In a visual field test, when the user P fixes his/her gaze at the fixation point at the center of the visual field test image G1, the identifiers in the regions near the fixation point can be easily perceived by the user P, and the identifiers in the regions farther away from the fixation point become harder to perceive for the user P.

Thus, in the visual field test image G1, an identifier located farther away from the fixation point M as the center is indicated in a larger size so that visibility of the identifiers at the periphery of the visual field test image G1 can be improved. Note that the visual field test image G1 may also be used to measure the visual acuity distribution of the retina itself, for example.

Figure 21:
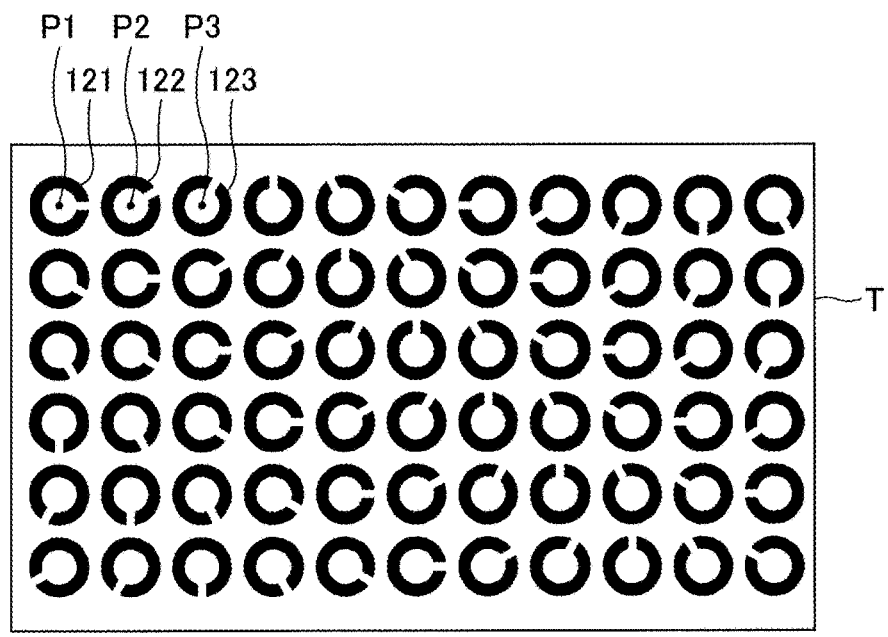
FIG. 21 is a first diagram illustrating an example of a visual acuity test image according to the second embodiment.

In the following, the visual acuity test image will be described with reference to FIGS. 21 to 28. FIG. 21 is a first diagram showing an example of the visual acuity test image according to the second embodiment.

In the visual acuity test image T shown in FIG. 21, Landolt rings are arranged into 6 rows and 11 columns. According to an aspect of the present embodiment, coordinates indicating the center of each Landolt ring included in the visual acuity test image T may be associated with the visual acuity test image T.

For example, assuming the visual acuity test image T was displayed on a test result input screen for visual acuity testing, and a user was unable to discern the gaps in the Landolt rings 121 to 123 in the visual acuity test image T, in the present embodiment, the coordinates of the respective center points P1, P2, P3 of the Landolt rings 121, 122, and 123 may be output as information identifying the Landolt rings for which the user could not discern the gaps.

Figure 22:
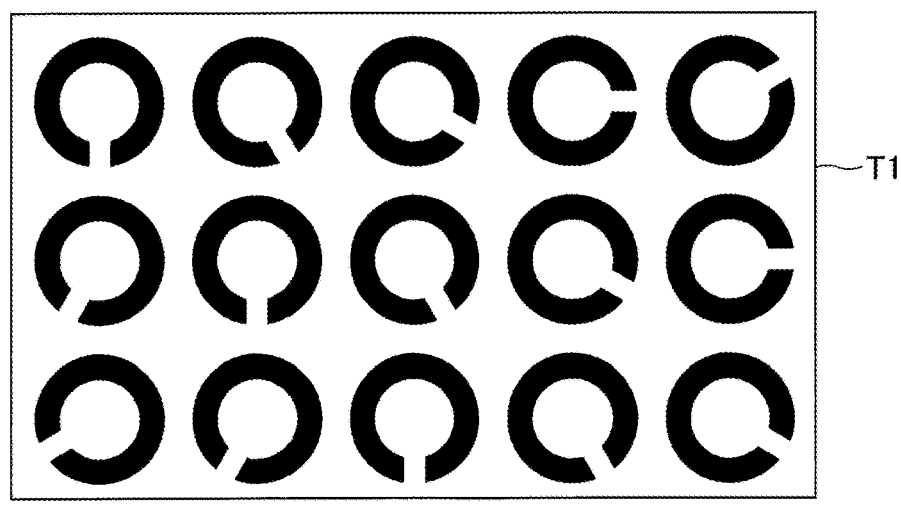
FIG. 22 is a second diagram illustrating an example of the visual acuity test image according to the second embodiment.

FIG. 22 is a second diagram showing an example of the visual acuity test image according to the second embodiment. In the visual acuity test image T1 shown in FIG. 22, Landolt rings are arranged into 3 rows and 5 columns. As can be appreciated, the Landolt rings in the visual acuity test image T1 are larger than the Landolt rings in the visual acuity test image T shown in FIG. 21.

In the present embodiment, visual acuity test images having Landolt rings in various sizes for various levels of visual acuity are provided in addition to the example visual acuity test images shown in FIGS. 21 and 22.

In the present embodiment, the size of the Landolt rings to be projected onto the retina of the user may be selected according to the visual acuity of the user, and a visual acuity test image displaying Landolt rings in the selected size may be projected onto the retina of the user. Note that the size of the Landolt rings to be projected onto the retina of the user may be selected by the user or test administrator, for example.

In the present embodiment, by changing the size of the Landolt rings of the visual acuity test image T in small increments or continuously, the visual acuity, expressed in decimal notation, may be measured up to two decimal places.

Figure 23:
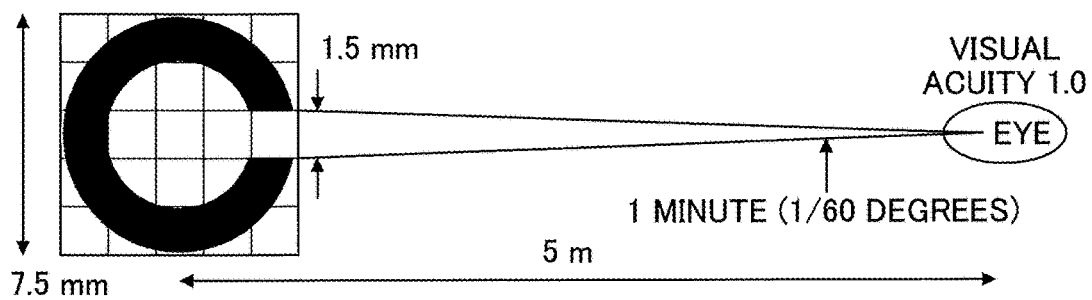
FIG. 23 is a diagram illustrating a Landolt ring.

In the following, the Landolt ring will be described with reference to FIG. 23. FIG. 23 is a diagram showing the Landolt ring.

The Landolt ring is a black circular ring, and the ratio of the diameter of the circular ring to the stroke width of the circular arc to the width of the ring opening (the gap width) is set to 5:1:1.

In the present embodiment, for example, when a gap of about 1.45 mm can be discerned from a distance of 5 m, the visual acuity is determined to be 1.0. More specifically, a person with the ability to determine the position of the gap of a Landolt ring with a diameter of 7.5 mm, a stroke width of 1.5 mm, and a gap width of 1.5 mm when viewing the Landolt ring from a distance of 5 m may be deemed to have a visual acuity of "1.0".

Thus, in the present embodiment, for example, in the case of measuring whether a person has a visual acuity of 1.0 or more, the image projection device 200 may be used to project onto the retina of the person, a visual acuity test image T including a Landolt ring in a size corresponding to the size of a Landolt ring with a diameter of 7.5 mm, a stroke width of 1.5 mm, and a gap width of 1.5 mm viewed from a distance of 5 m.

Figure 24:
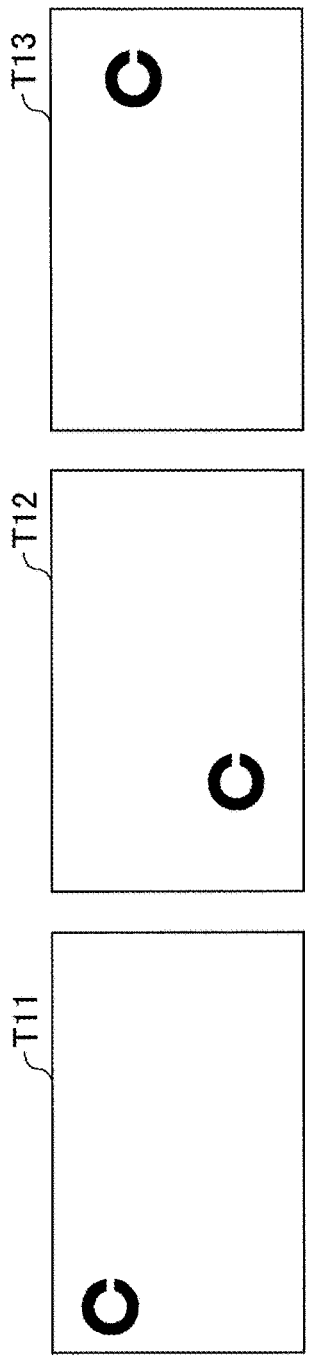
FIG. 24 is a third diagram illustrating an example of the visual acuity test image according to the second embodiment.

FIG. 24 is a third diagram showing an example of the visual acuity test image according to the second embodiment.

In the example of FIG. 24, visual acuity test images with Landolt rings arranged at different positions are shown. In FIG. 24, a visual acuity test image T11 has one Landolt ring arranged at the upper left side, and a visual acuity test image T12 has one Landolt ring arranged at the lower left side. Also, a visual acuity test image T13 shown in FIG. 24 has one Landolt ring arranged at the upper right side.

In the present embodiment, by sequentially projecting visual acuity test images having Landolt rings arranged at different positions as shown in FIG. 24 on the retina of a user, the presence/absence of defects in the visual field of the user may be tested in addition to testing the visual acuity of the user.

Note that although one visual acuity test image is arranged to have one Landolt ring arranged therein in the example of FIG. 24, the present invention is not limited thereto. That is, a plurality of Landolt rings may be arranged in one visual acuity test image.

Also, although visual acuity test images having Landolt rings arranged at different positions are sequentially projected onto the retina of the user in the example of FIG. 24, the present invention is not limited thereto. For example, a visual acuity test image may be projected onto the retina of the user as a moving image in which the position of the Landolt ring moves.

By using visual acuity test images as described above, in the present embodiment, the visual field of a user may be associated with the visual acuity of the user. In other words, in the present embodiment, the distribution of visual acuity in the retina of the user may be determined.

Figure 25:
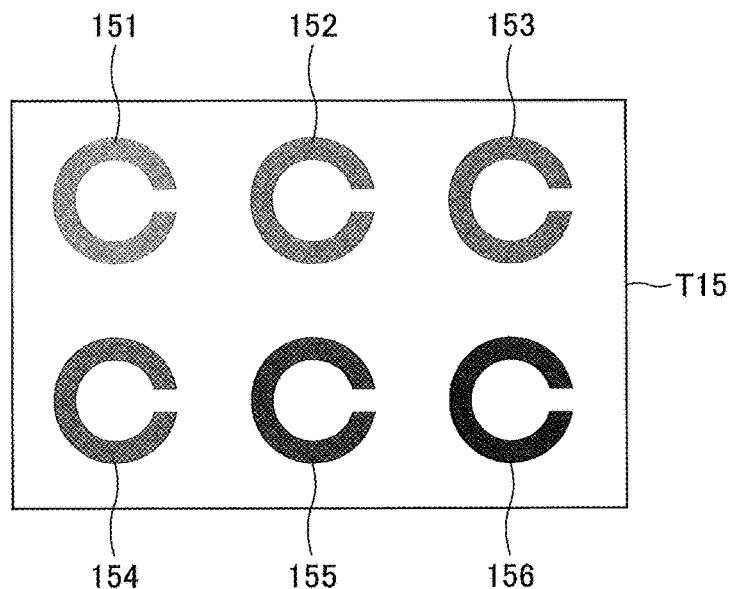
FIG. 25 is a fourth diagram illustrating an example of the visual acuity test image according to the second embodiment.

FIG. 25 is a fourth diagram showing an example of the visual acuity test image according to the second embodiment. The visual acuity test image T15 shown in FIG. 25 has a plurality of Landolt ring images 151 to 156 in different luminance levels arranged therein.

In the visual acuity test image T15, the luminance level gradually decreases from the Landolt ring image 151 toward the Landolt ring image 156.

According to an aspect of the present embodiment, by changing the luminance level of Landolt ring images, the luminance required for the user to discern an image may be determined.

Note that in the visual acuity test image according to the present embodiment, the Landolt ring may be a black image, or may be an image of a color other than black, such as blue, red, or green, for example. According to an aspect of the present embodiment, by changing the color of the Landolt ring images, the presence/absence of abnormalities in color vision may be tested in addition to testing the visual acuity.

Figure 26:
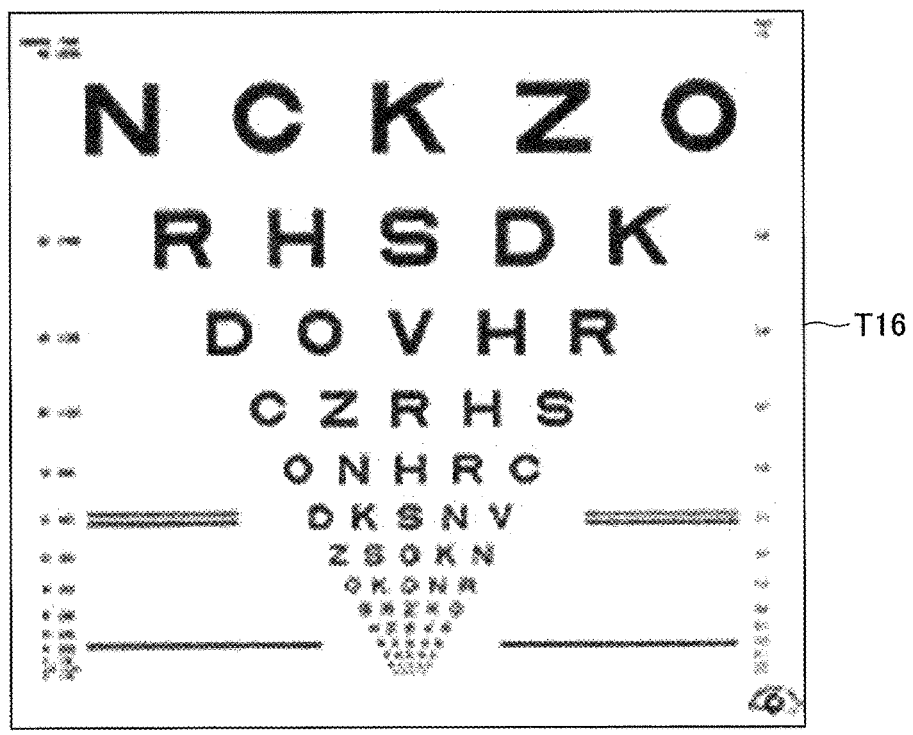
FIG. 26 is a fifth diagram illustrating an example of the visual acuity test image according to the second embodiment.

FIG. 26 is a fifth diagram showing an example of the visual acuity test image according to the second embodiment. According to an aspect of the present embodiment, a visual acuity test may be conducted using images other than Landolt ring images.

The visual acuity test image T16 shown in FIG. 26 includes an ETDRS (Early Treatment of Diabetic Retinopathy Study) chart.

In the ETDRS chart, five visual targets are arranged in one line, and the visual target size differences between the lines are in 0.1 log MAR units. Also, characters corresponding to the visual targets are Sloan letters (10 characters of C, D, H, K, N, O, R, S, V, Z) in the Sloan font. In the ETDRS chart, the space between the visual targets is equal to the size of one visual target, and letter-by-letter scoring is performed rather than line-by-line scoring.

As described above, according to an aspect of the present embodiment, the visual acuity test may be conducted using a visual target other than the Landolt ring. In addition to the ETDRS chart, a visual target other than the Landolt ring may include a tumbling E chart, for example.

Figure 27:
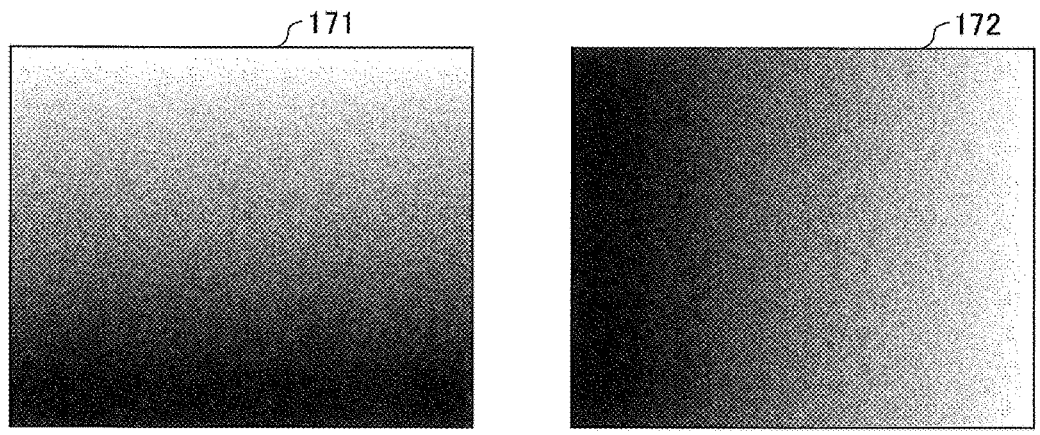
FIG. 27 is a diagram illustrating an example of an image used for contrast sensitivity testing.
Figure 28:
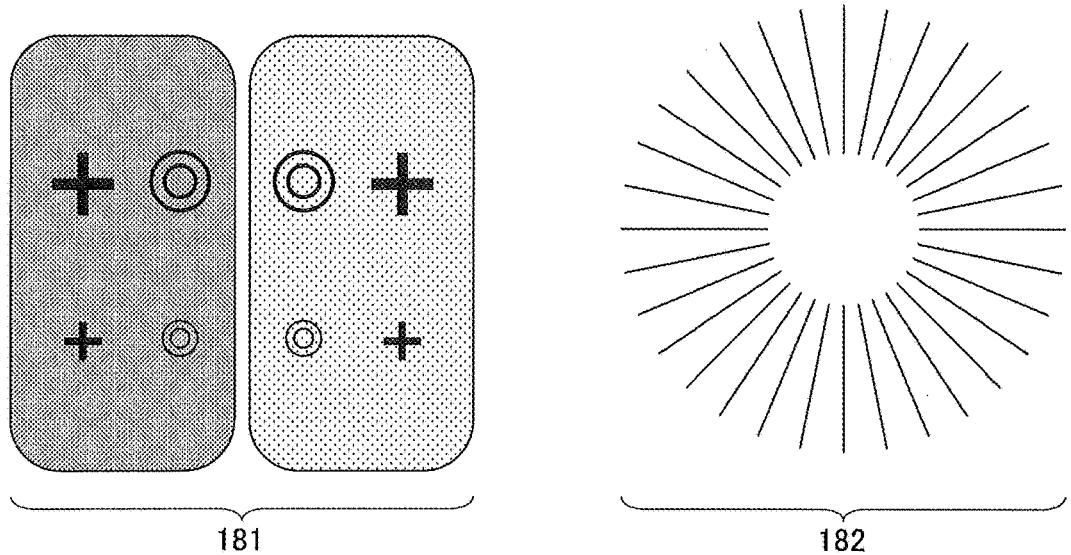
FIG. 28 is a diagram illustrating an example of an image used for astigmatism testing.

FIG. 27 is a diagram showing example images used for contrast sensitivity testing, and FIG. 28 is a diagram showing example images used for astigmatism testing.

The visual acuity test image T according to the present embodiment may include an image for contrast sensitivity testing as shown in FIG. 27, for example.

The images 171 and 172 shown in FIG. 27 are used for projecting color gradations onto the entire visual field. According to an aspect of the present embodiment, the contrast sensitivity of a user can be measured by projecting a color gradation image onto the visual field of the user and inputting the color that can be perceived by the user as a test result.

Note that according to an aspect of the present embodiment, a plurality of images for projecting the same color onto the entire visual field may be prepared instead of a color gradation image, and the plurality of images may be sequentially projected to implement a color gradation.

Also, the visual acuity test image T according to the present embodiment may include image 181 and image 182 for astigmatism testing as shown in FIG. 28, for example. By including these images in the visual acuity test image T, a user may also be tested for astigmatism.

Figure 29:
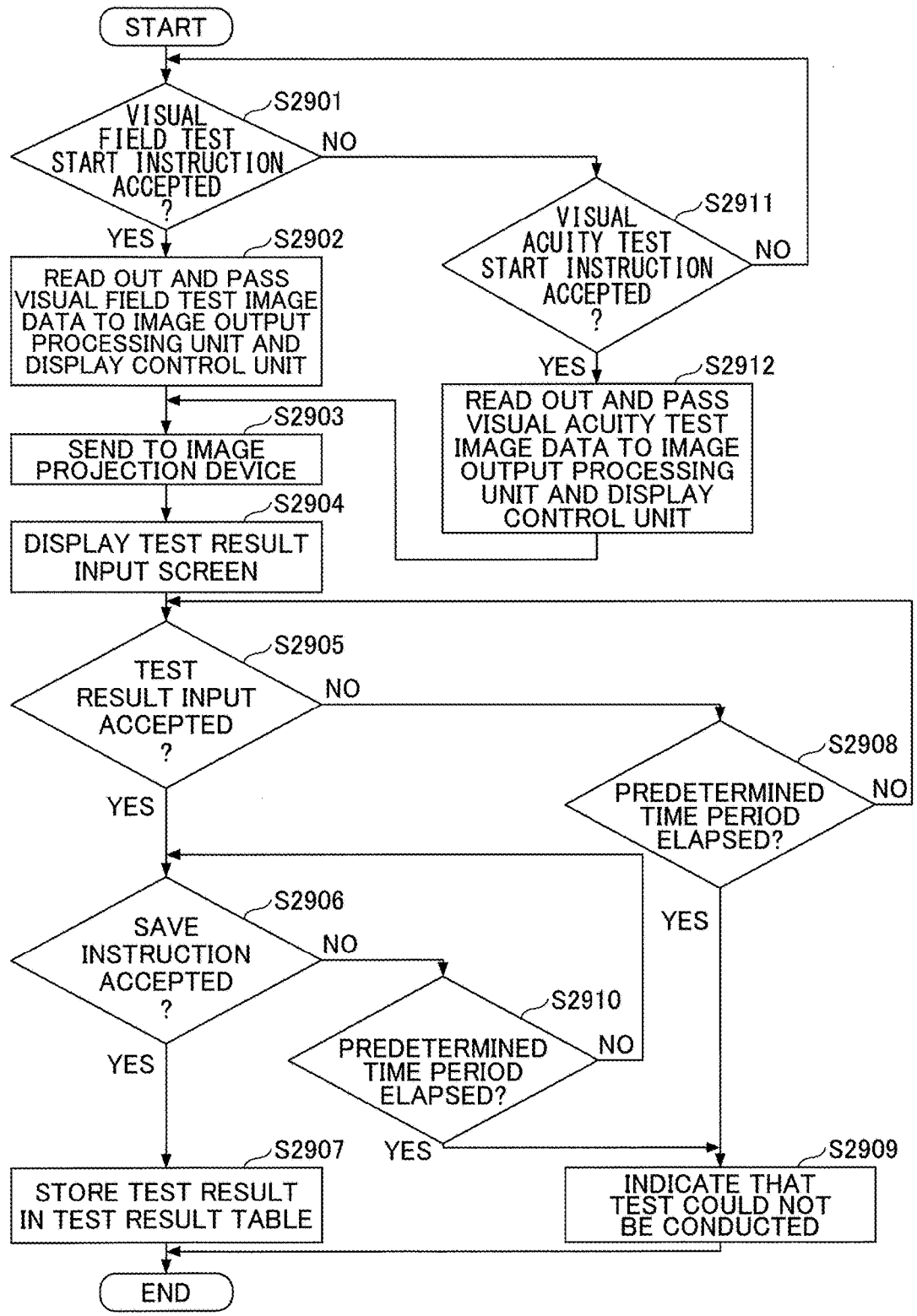
FIG. 29 is a flowchart illustrating example process operations implemented by the test processing unit according to the second embodiment.

In the following, process operations of the test processing unit 340 of the terminal device 300A according to the present embodiment will be described with reference to FIG. 29. FIG. 29 is a flowchart showing process operations of the test processing unit according to the second embodiment.

In the terminal device 300A according to the present embodiment, the test processing unit 340 determines whether the input accepting unit 343 has accepted a visual field test start request (step S2901). In step S2901, if it is determined that a visual field test start request has not been accepted, the test processing unit 340 proceeds to step S2911 as described below.

Upon accepting a visual field test start request in step S2901, the image data selection unit 344 of the test processing unit 340 selectively reads the visual field test image data from among the image data held by the image data holding unit 341, and passes the visual field test image data to the image output processing unit 320 and the display control unit 342 (step S2902).

The image output processing unit 320 transmits the visual field test image data to the image projection device 200 (step S2903). In the image projection device 200, when the visual field test image data is input to the control unit 230, the projection unit 210 scans the retina of the user with image light beams corresponding to the visual field test image data so that the user can visually perceive the visual field test image G.

The display control unit 342 causes the display operation device 301 of the terminal device 300A to display a test result input screen including the visual field test image G based on the visual field test image data (step S2904). Note that the test result input screen will be described in detail below.

Then, the test processing unit 340 determines whether the input accepting unit 343 has accepted a test result input for the visual field test via the test result input screen (step S2905). In step S2905, if it is determined that a test result input has not been accepted, the input accepting unit 343 proceeds to step S2908 as described below.

Upon accepting a test result input in step S2905, the input accepting unit 343 determines whether a save instruction to save the test result has been accepted (step S2906). In step S2906, if it is determined that a save instruction has not been accepted, the input accepting unit 343 proceeds to step S2910 as described below.

Upon accepting an input of the save instruction in step S2906, the test processing unit 340 has the test result storage unit 345 store the test result in the visual field visual acuity information storage unit 330A (step S2907) and ends the process.

In the case where a test result input is not accepted in step S2905, the input accepting unit 343 determines whether a predetermined time period has elapsed (step S2908). In step S2908, if the predetermined time period has not elapsed, the input accepting unit 343 returns to step S2905.

If it is determined in step S2908 that the predetermined time period has elapsed, the test processing unit 340 causes the display control unit 342 to display on the terminal device 300A a notification that the visual field test was not properly conducted (step S2909) and ends the process.

If it is determined in step S2906 that a save instruction has not been accepted, the input accepting unit 343 determines whether a predetermined time period has elapsed (step S2910). If it is determined in step S2910 that the predetermined time period has not elapsed, the input accepting unit 343 returns to step S2906.

If it is determined in step S2910 that the predetermined time period has elapsed, the test processing unit 340 proceeds to step S2909.

Also, if it is determined in step S2901 that a visual field test start request has not been accepted, the test processing unit 340 according to the present embodiment determines whether the input accepting unit 343 has accepted a visual acuity test start request. If it is determined in step S2911 that a visual acuity test start request has not been accepted, the test processing unit 340 returns to step S2901.

Upon accepting a visual acuity test start request in step S2911, the image data selection unit 344 of the test processing unit 340 selectively reads the visual acuity test image data from among the image data held by the image data holding unit 341 and passes the visual acuity test image data to the image output processing unit 320 and the display control unit 342 (step S2912), and the process proceeds to step S2903.

Figure 30:
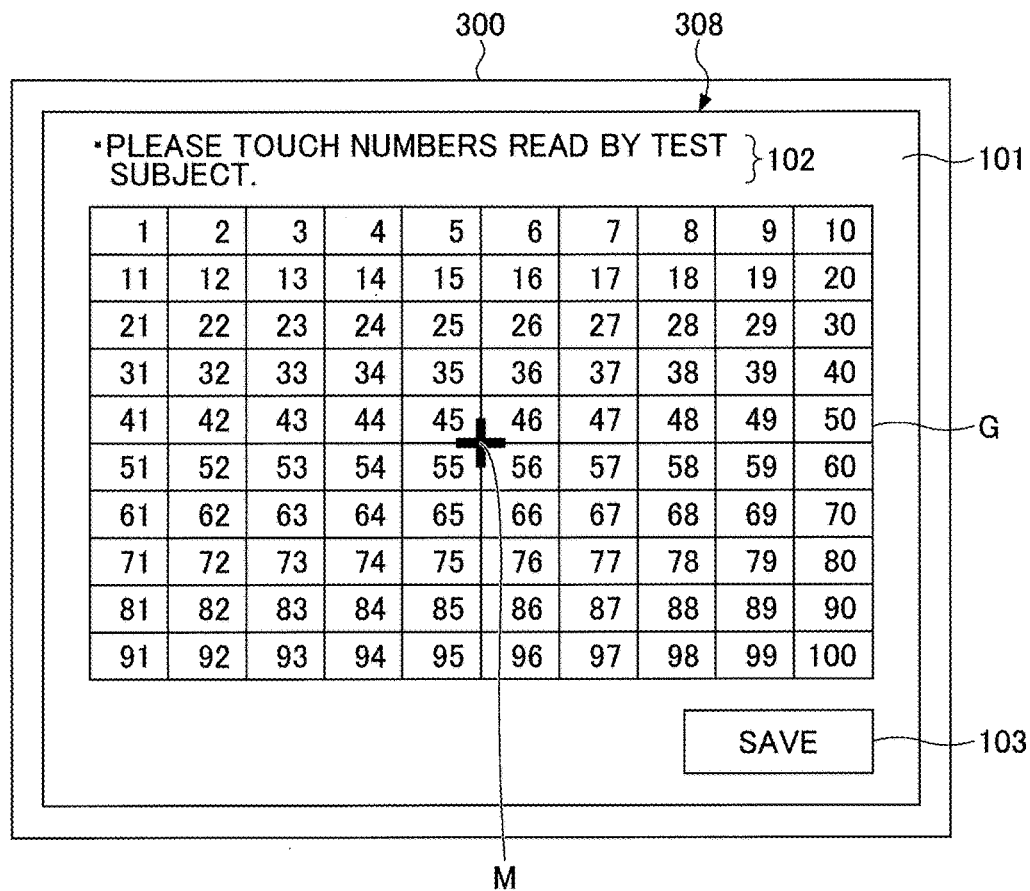
FIG. 30 is a diagram illustrating an example of a test result input screen according to the second embodiment.

In the following, the test result input screen for inputting a test result will be described with reference to FIG. 30. FIG. 30 is a diagram showing an example of a test result input screen according to the second embodiment.

The test result input screen 101 shown in FIG. 30 displays the visual field test image G. Further, the test result input screen 101 displays a message 102 for prompting selection of a readable number in the visual field test image G and a button 103 for instructing to save the test result.

Note that in the example of FIG. 30, the message 102 states "Please touch the number read by the user" to prompt selection of a number in the visual field test image G that could be visually perceived by the user. However, the present invention is not limited to such an example. For example, the message 102 may alternatively be a message prompting selection of a number in the visual field test image G that could not be visually perceived by the user.

The content of the message 102 may be preset by an administrator of the image projection system 100A, for example. Also, whether to prompt selection of a readable number or an unreadable number may be set up with respect to each user, for example.

In the following, the visual field information table 331 and the visual acuity information table 332 stored in the visual field visual acuity information storage unit 330A according to the present embodiment will be described. First, a visual field information table 331-P for the user P will be described with reference to FIGS. 31 to 36.

Figure 31:
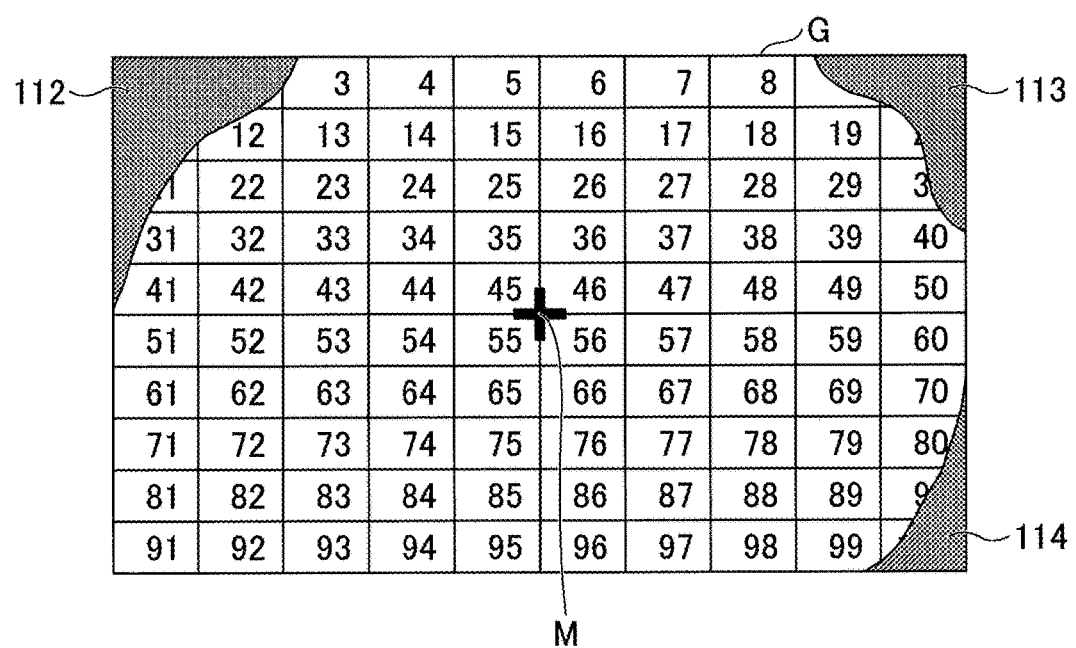
FIG. 31 is a first diagram illustrating an example of how the visual field test image according to the second embodiment is visually perceived.

FIG. 31 is a first diagram showing an example of how the visual field test image according to the second embodiment is visually perceived. FIG. 31 illustrates an example of how the visual field test image G is visually perceived by the user P having the visual field as shown in FIG. 9.

The visual field 111 of the user P includes defective areas 112, 113, and 114 (see FIG. 9).

When the visual field test image G is projected onto the retina of the user P having a visual field with defective areas as described above, the defective areas 112, 113, and 114 are also reflected in the visual field test image G.

As such, the visual field test image G is visually perceived by the user P as an image as shown in FIG. 31 with missing portions (shaded portions) corresponding to the defective areas 112, 113, and 114. Thus, the numbers inscribed in the regions located at the positions corresponding to the defective areas cannot be visually perceived by the user P.

In the example of FIG. 31, the regions with the identifiers "1", "2", "11", and "21" are included in the defective area 112, and the regions with the identifiers "9", "10", "20", and "30" are included in the defective area 113. Thus, these numbers correspond to numbers that cannot be read by the user P.

Figure 32:
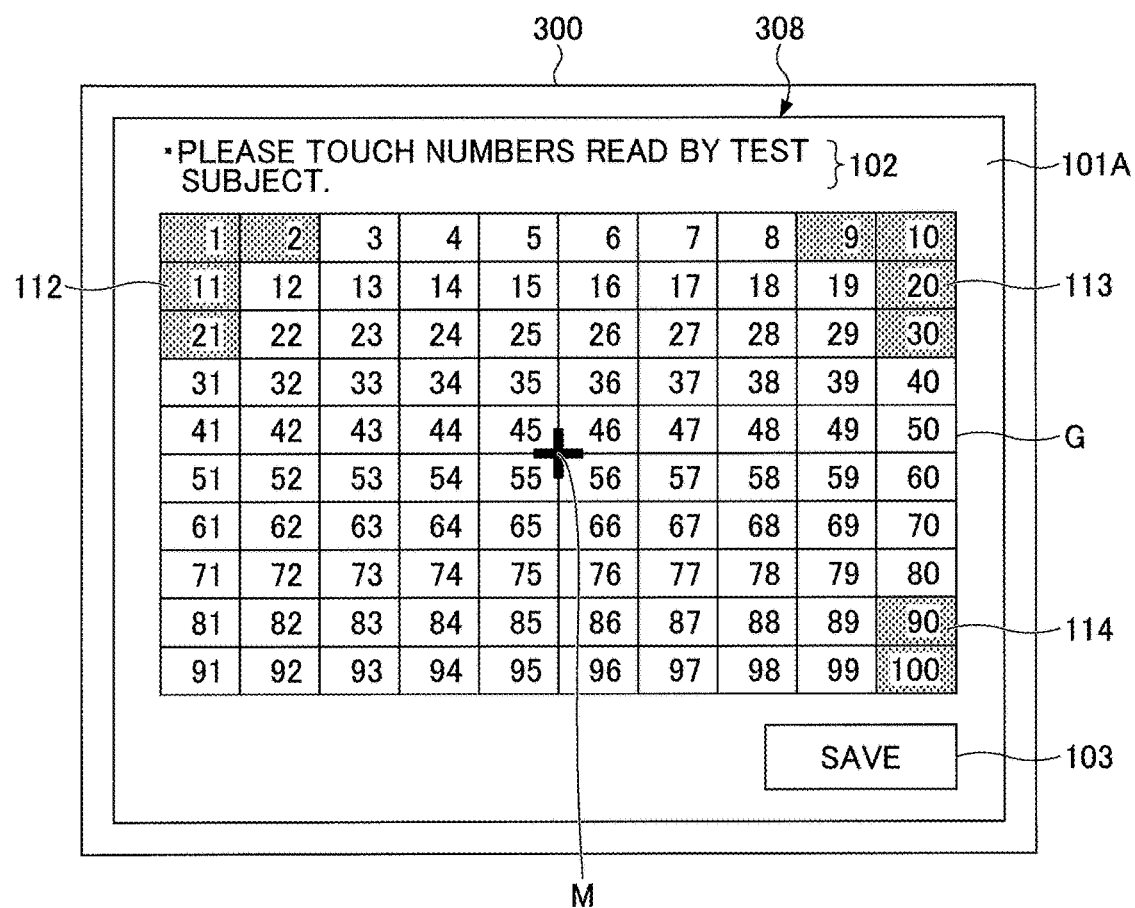
FIG. 32 is a first diagram illustrating an example test result input screen having a test result input thereto according to the second embodiment.

FIG. 32 is a first diagram showing an example of a test result input screen according to the second embodiment having a test result input thereto.

The test result input screen 101A shown in FIG. 32 represents an example case where the test result of the user P is input to the test result input screen 101.

In the test result input screen 101A, the numbers in the regions included in the defective areas 112 to 114 are not selected, and the numbers in the regions other than the regions included in the defective areas 112 to 114 are selected.

Note that in the test result input screen 101A of FIG. 32, the regions in the visual field test image G that have been selected are displayed so that they appear brighter than the regions that have not been selected. However, the present invention is not limited thereto. The test result input screen 101A is preferably configured to display the selected regions and the non-selected regions of the visual field test image G in different modes so that they can be distinguished from each other.

It can be appreciated that in the test result input screen 101A, the numbers 3-8, 12-19, 22-29, 31-89, and 91-99 were selected as numbers that were read by the user P. Thus, it can be appreciated that out of the regions of the visual field test image G displayed on the test result input screen 101A, the regions inscribed with the selected numbers read by the user P correspond to the visual field of the user P.

When inputting of the test result to the test result input screen 101A is completed and the button 103 is operated, the input test result is stored in the visual field visual acuity information storage unit 330A as the visual field information table 331.

FIG. 33 is a first diagram showing an example of the visual field information table according to the second embodiment.

The visual field information table 331 according to the present embodiment is set up for each user, and FIG. 33 shows a visual field information table 331-P for the user P.

The visual field information table 331-P according to the present embodiment includes a user ID, a test date, an input time, readable numbers, and unreadable numbers as items of information. In the visual field information table 331-P, the item "user ID" is associated with the other items of information. In the following description, information including the values of the items in the visual field information table 331-P is referred to as visual field test result information. The visual field test result information according to the present embodiment corresponds to visual field information indicating the visual field of a user.

The value of the item "test date" is information indicating the date on which the visual field test was conducted. The value of the item "input time" is information indicating the time at which the test result of the visual field test was input to the terminal device 300. That is, the value of the item "input time" is information indicating the time at which the visual field test was conducted.

The value of the item "readable numbers" indicates the numbers in the visual field test image G that could be read by the user. In other words, the value of the item "readable numbers" indicates the numbers inscribed in the selected regions that were selected as readable numbers from among the regions of the visual field test image G displayed on the test result input screen 101.

The value of the item "unreadable numbers" indicates the numbers in the visual field test image G that could not be read by the user. In other words, the value of the item "unreadable numbers" indicates the numbers inscribed in non-selected regions that were not selected as readable numbers from among the regions of the visual field test image G displayed on the test result input screen 101.

As can be appreciated, the visual field information table 331-P shown in FIG. 33 stores test results input by the user P with the user ID "001", including a test result input at 10:00 on Apr. 10, 2016 and a test result input at 18:00 on Apr. 13, 2016.

In the following, a visual field information table 331-Q for the user Q will be described with reference to FIGS. 34 to 36.

Figure 34:
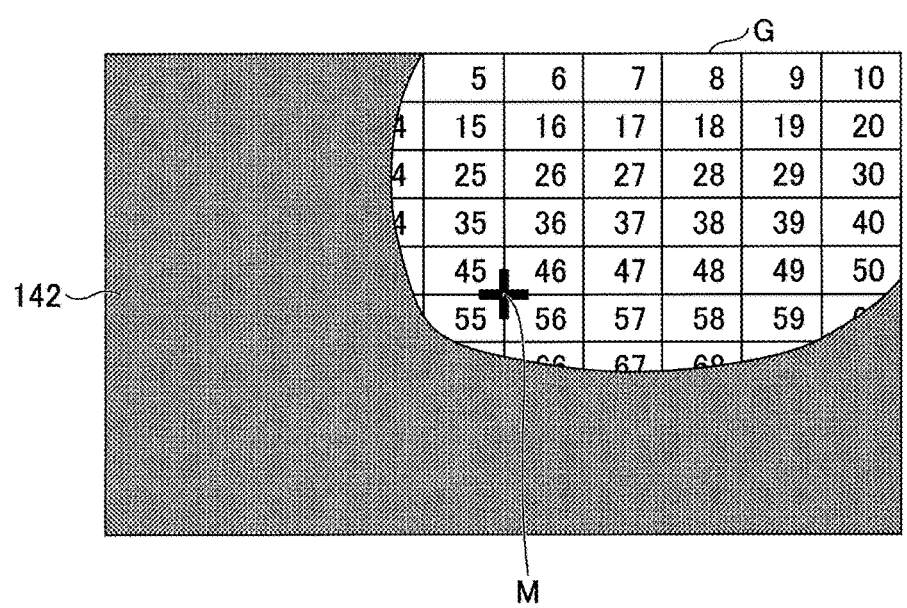
FIG. 34 is a second diagram illustrating an example of how the visual field test image according to the second embodiment is visually perceived.

FIG. 34 is a second diagram showing an example of how the visual field test image according to the second embodiment is visually perceived. FIG. 34 shows an example of how the visual field test image G is visually perceived by the user Q having the visual field as shown in FIG. 12.

The visual field 141 of the user Q includes a defective area 142 (see FIG. 12).

As such, the visual field test image G will be visually perceived by the user Q as an image as shown in FIG. 34 with a missing portion (shaded portion) corresponding to the defective area 142. Thus, in the example of FIG. 34, the numbers inscribed in the regions located at the position corresponding to the defective area 142 cannot be read by the user Q.

Figure 35:
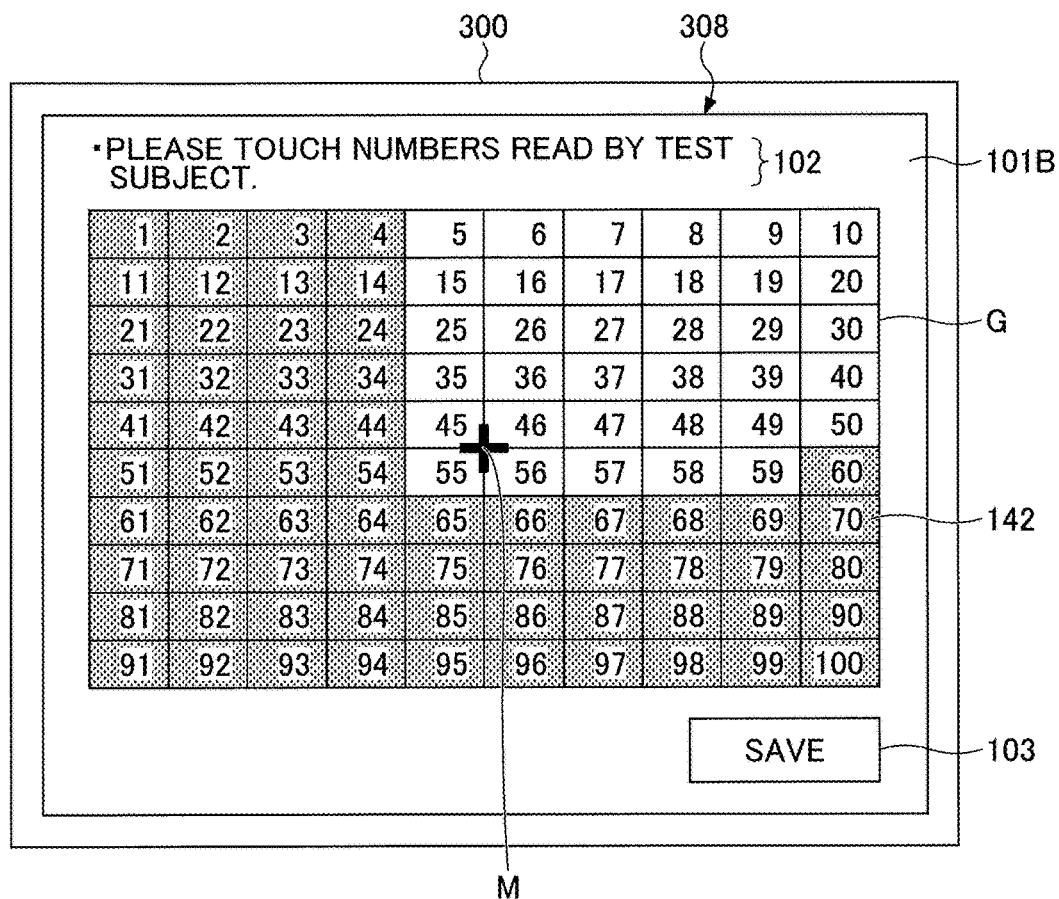
FIG. 35 is a second diagram illustrating an example test result input screen having a visual field test result input thereto according to the second embodiment.

FIG. 35 is a second diagram showing an example of a test result input screen according to the second embodiment having a visual field test result input thereto.

The test result input screen 101B shown in FIG. 35 represents an example case where a test result of the user Q has been input to the test result input screen 101.

It can be appreciated that in the test result input screen 101B, the numbers inscribed in the regions included in the defective area 142 have not been selected, and the numbers inscribed in the regions other than the regions included in the defective area 142 have been selected.

It can be appreciated that in the test result input screen 101B, the numbers 5-10, 15-20, 25-30, 35-40, 45-50, 55-59 have been selected as numbers read by the user Q. Accordingly, it can be appreciated that the regions inscribed with the selected numbers read by the user Q correspond to the visual field of the user Q.

When inputting of the test result to the test result input screen 101B is completed and the button 103 is operated, the input test result is stored in a visual field information table 331-Q of the visual field visual acuity information storage unit 330A.

FIG. 36 is a second diagram showing an example of the visual field information table according to the second embodiment.

As can be appreciated, the visual field information table 331-Q shown in FIG. 36 stores test Results of visual field tests conducted on the user Q with the user ID "002", including a test result input at 10:00 on Apr. 10, 2016, and a test result input at 18:00 on Apr. 13, 2016.

As described above, according to an aspect of the present embodiment, a visual field information table 331 may be generated by conducting a visual field test with a simple configuration on a user and storing the test result as visual field information indicating the visual field of the user. According to an aspect of the present embodiment, the visual field information table 331 stored in the terminal device 300A may be stored in a server of a medical institution or the like, for example.

Note that although the visual field test image G has been described in the present embodiment as having a size covering the visual field of a user, the present invention is not limited thereto.

For example, according to an aspect of the present embodiment, the image projection device 200 may be provided with a mechanism for detecting the direction in which the pupil of a user has moved. By providing such a mechanism in the image projection device 200, the irradiation direction of image light beams from the light source 211 may be changed to be in the direction in which the pupil of the user has moved, for example.

In this way, the user can visually perceive the same visual field test image G both before and after moving the pupil. Thus, the user does not have to face a fixed direction, and can receive a visual field test in any posture. Also, in this way, the user may be able to visually perceive the visual field test image G at all times during the visual field test irrespective of the posture of the user, for example, and the testing accuracy may be improved.

Also, in the visual field information table 331 according to an aspect of the present embodiment, for example, instead of including values of the item "readable numbers" and the item "unreadable numbers", coordinate information indicating the positions of the regions represented by the identifiers may be used. Further, the visual field information table 331 may include coordinate information indicating the positions of the regions represented by the values of the item "readable numbers" and the item "unreadable numbers" as items of information.

For example, the coordinate information may be acquired from the visual field test image data, or may be acquired from a table associating the identifier of each region with coordinate information specifying the region corresponding to the identifier, for example. Such a table may be provided to the terminal device 300 in advance, for example.

Further, according to an aspect of the present embodiment, image data of the visual field test image G having certain regions selected may be included in the visual field test result information. That is, according to an aspect of the present embodiment, image data of the visual field test image G having certain regions selected as shown in FIG. 32 or FIG. 35 may be stored as one item of information in the visual field test result information.

Also, according to an aspect of the present embodiment, the brightness (luminance) of the visual field test image G may be incrementally changed, and a test result may be input each time a change is made, for example. In this case the visual field information table 331 may include an additional item "brightness of visual field test G", and the visual field test result information may include the value of the item "brightness of visual field test G".

According to an aspect of the present embodiment, by inputting a test result for each brightness level of the visual field test image G, the visual field of the user for varying levels of brightness may be determined.

In the following, the visual acuity information table 332 will be described with reference to FIGS. 37 to 40.

Figure 37:
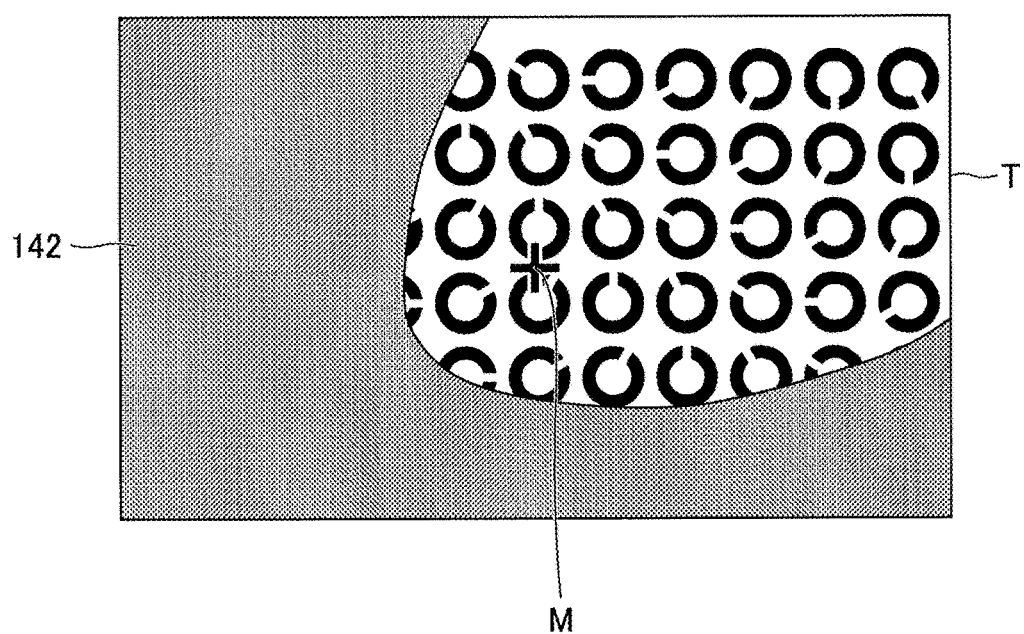
FIG. 37 is a diagram illustrating an example of how the visual acuity test image according to the second embodiment is visually perceived.

FIG. 37 is a diagram showing an example of how the visual acuity test image according to the second embodiment is visually perceived. FIG. 37 shows an example of how the visual acuity test image T will be visually perceived by the user Q having the visual field as shown in FIG. 12.

The visual field 141 of the user Q includes a defective area 142. As such, the visual acuity test image T will be visually perceived by the user Q as an image as shown in FIG. 37 with a missing portion (shaded portion) corresponding to the defective area 142. That is, the Landolt rings drawn in the area located at the position corresponding to the defective area 142 cannot be visually perceived by the user Q. Thus, in the example of FIG. 37, the gaps of the Landolt rings drawn in the area corresponding to the defective area 142 cannot be discerned by the user Q.

Figure 38:
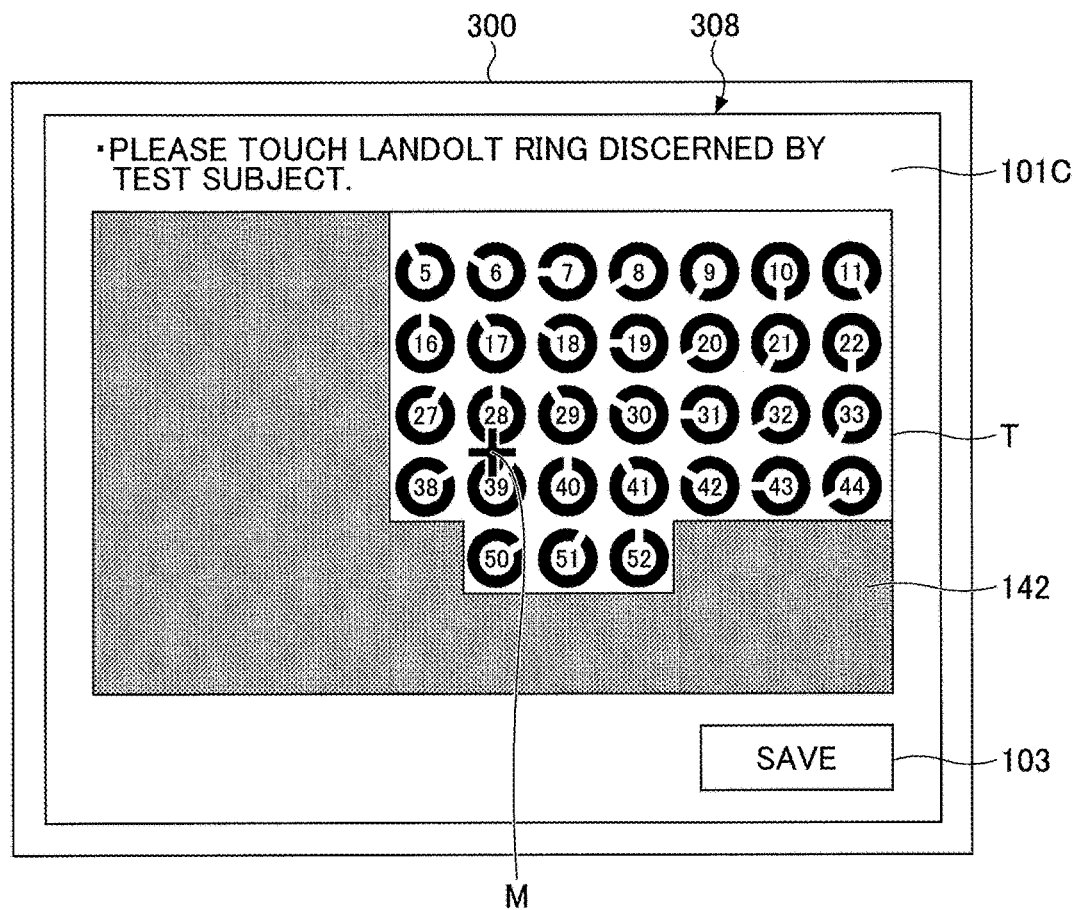
FIG. 38 is a diagram illustrating an example test result input screen having a visual acuity test result input thereto according to the second embodiment.

FIG. 38 is a diagram showing an example of a test result input screen having a visual acuity test result input thereto according to the second embodiment.

The test result input screen 101C shown in FIG. 38 represents an example case where a visual field test result of the user Q has been input to a test result input screen displaying the visual acuity test image T.

In the present embodiment, visual acuity test images T including Landolt rings of different sizes are sequentially projected onto the retina of the user Q. In the present embodiment, for example, the user Q determines the direction of the gap in each Landolt ring projected onto an area other than the defective area 142, and on the test result input screen 101C, the test administrator selects the Landolt ring for which the user was able to determine the direction of the gap.

Note that the test administrator may not be able to easily determine that there is a defective area 142 in the visual field of the user Q or the location of the defective area 142 in the visual field of the user Q. Thus, for example, in the visual acuity test image T, an identifier for identifying each Landolt ring may be provided at the center or in the vicinity of each Landolt ring.

For example, as shown in FIG. 38, each Landolt ring may be assigned a number as an identifier for identifying the Landolt ring and the number may be indicated at the center of each Landolt ring.

Also, it can be appreciated that in the test result input screen 101C, the Landolt rings in the area corresponding to the defective area 142 are not selected, and the Landolt rings in the area other than the defective area 142 are selected.

It can be appreciated that in the test result input screen 101C, the Landolt rings with the numbers 5-11, 16-22, 27-33, 38-44, and 50-52 have been selected as the Landolt rings for which the user Q was able to discern the gaps formed therein.

According to an aspect of the present embodiment, by conducting a visual acuity test in the above-described manner, the visual acuity for the visual field of the user Q may be measured. Also, according to an aspect of the present embodiment, a visual field test for determining whether a defective area exits in the visual field of the user Q may be conducted at the same time as a visual acuity test.

When inputting of the visual acuity test result to the test result input screen 101C is completed and the button 103 is operated, the input visual acuity test result is stored in a visual acuity information table 332-Q.

FIG. 39 is a first diagram showing an example of the visual acuity information table according to the second embodiment. The visual acuity information table 332 according to the present embodiment is provided for each user, and FIG. 39 shows the visual acuity information table 332-Q for the user Q.

The visual acuity information table 332-Q according to the present embodiment includes a user ID, a test date, an input time, indiscernible Landolt rings, and discernible Landolt rings as items of information. In the visual acuity information table 332-Q, the item "user ID" is associated with the other items of information. In the following description, information including the values of the items in the visual acuity information table 332-Q corresponds to visual acuity information of the user Q.

The value of the item "indiscernible Landolt rings" indicates the Landolt rings in the visual acuity test image T for which the user was not able to discern the gaps formed therein. In other words, the value of the item "indiscernible Landolt rings" includes the identifiers identifying the Landolt rings that have not been selected as the Landolt rings that could be discerned by the user from among the Landolt rings in the visual acuity test image T displayed on the input screen 101C.

The value of the item "discernible Landolt rings" indicates the Landolt rings in the visual acuity test image T for which the user was able to discern the gaps formed therein. In other words, the item "discernible Landolt rings" includes the identifiers identifying the Landolt rings selected as the Landolt ring that could be discerned by the user from among the Landolt rings in the visual acuity test image T displayed on the input screen 101C.

It can be appreciated that the visual acuity information table 332-Q shown in FIG. 39 stores a test result of a visual acuity test conducted on the user Q with the user ID "002" that has been input at 10:00 on Apr. 10, 2016.

Note that in the example of FIG. 39, the values of the items "indiscernible Landolt rings" and "discernible Landolt rings" include identifiers identifying the Landolt rings, but the present invention is not limited thereto. For example, the values of the items "indiscernible Landolt rings" and "discernible Landolt rings" may include the coordinates of the center points of the Landolt rings selected via the test result input screen 101C.

FIG. 40 is a second diagram showing an example of the visual acuity information table according to the second embodiment. The visual acuity information table 332A-Q shown in FIG. 40 shows an example of a visual acuity test result when a moving image of one moving Landolt ring is projected onto the retina of the user Q.

In the visual acuity information table 332A-Q, the value of the item "discernible area" is information indicating the coordinates of an area in the visual acuity test image T where the Landolt ring could be discerned by the user Q while the Landolt ring was being displayed.

Also, the value of the item "indiscernible area" is information indicating the coordinates of an area in the visual acuity test image T where the Landolt ring could not be discerned by the user Q while the Landolt ring was being displayed. Note that the coordinates used herein may correspond to the coordinates of the center point of the Landolt ring, for example.

It can be appreciated that in the example of FIG. 40, the user Q was able to discern the gap in the Landolt ring when the center point of the Landolt ring was included in the range from coordinates (x3, y3) to coordinates (x4, y4). Similarly, it can be appreciated that in the example of FIG. 40, the user Q was unable to discern the gap in the Landolt ring when the center point of the Landolt ring was included in the range from coordinates (x1, y1) to coordinates (x2, y2).

Note that according to an aspect of the present embodiment, the expression "discerning the gap of the Landolt ring" may include both a case where a person visually perceives the Landolt ring and also correctly determines the direction of the gap in the Landolt ring, and a case where a person visually perceives the Landolt ring but does not correctly determine the direction of the gap in the Landolt ring.

As described above, according to an aspect of the present embodiment, the Maxwellian view is used to directly project the visual field test image G, which is divided into a plurality of regions, onto a predetermined position of the retina so that each region of the visual field test image G corresponds to a certain position on the retina. Thus, by testing whether a person can see each of the regions, a visual field test can be conducted for each of the corresponding positions on the retina of the person.

Also, according to an aspect of the present embodiment, the Maxwellian view is used to directly project the visual acuity test image T, which includes one or more visual target images used for visual acuity testing, onto a predetermined position of the retina. In this way, in the present embodiment, the visual acuity of the retina itself can be measured. Further, in the present embodiment, the visual acuity distribution across the retina can be measured.

Further, note that although the image projection device 200 according to the present embodiment has a shape similar to ordinary eyeglasses, the present invention is not limited thereto. For example, the image projection device 200 may have a goggle shape covering both eyes of the user P.

Further, according to an aspect of the present embodiment, the area H (see FIG. 4) onto which an image is projected by the image projection device 200 is preferably large enough to cover the visual field of the user. A size that covers the visual field of the user may be, for example, a size that allows an image projected onto the retina to cover approximately 60° nasally and superiorly, approximately 70° inferiorly, and approximately 90°-100° temporally (laterally).

According to an aspect of the present embodiment, by setting the area onto which an image (test image) is to be projected to be in a size covering the visual field of the user (test subject), appropriate visual field testing can be conducted even with respect to a user having no abnormality in the visual field, retina, optic nerve, or the like.

Note that with respect to a user that is known to have a defect in a portion of the visual field, the area H onto which an image is to be projected may be arranged to be smaller than the above-described size of "approximately 60° nasally and superiorly, approximately 70° inferiorly, and approximately 90°-100° temporally".

Also, in a case where the user P inputs the visual field test result in the terminal device 300A, the user P may input the visual field test result after removing the image projection device 200 that was worn by the user, or the user may use the eye that is not being subjected to visual field testing to look at the screen of the terminal device 300A and input visual field test result, for example.

In this case, for example, when testing the visual field of the left eye, the image projection device 200 having the elements shown in FIG. 2 arranged on the left side of the eyeglass frame may be used, and when testing the visual field of the right eye, the image projection device 200 having the elements shown in FIG. 2 arranged on the right side of the eyeglass frame may be used. Further, in the case where it is difficult to input the test result to the terminal device 300A while wearing the image projection device 200, the user may request the test administrator to input the test result to the terminal device 300A, for example. In this case, for example, the user may communicate to the test administrator the area from which the user was able to read characters by reading out the characters that the user was able to visually perceive.

Third Embodiment

In the following, a third embodiment of the present invention will be described with reference to the drawings. The third embodiment differs from the second embodiment in that the function of the terminal device of the second embodiment is provided in a server external to the terminal device. In the following description of the third embodiment, features having substantially the same functional configuration as those of the second embodiment are given the same reference numerals as those used in the description of the second embodiment and explanations thereof are omitted.

Figure 41:
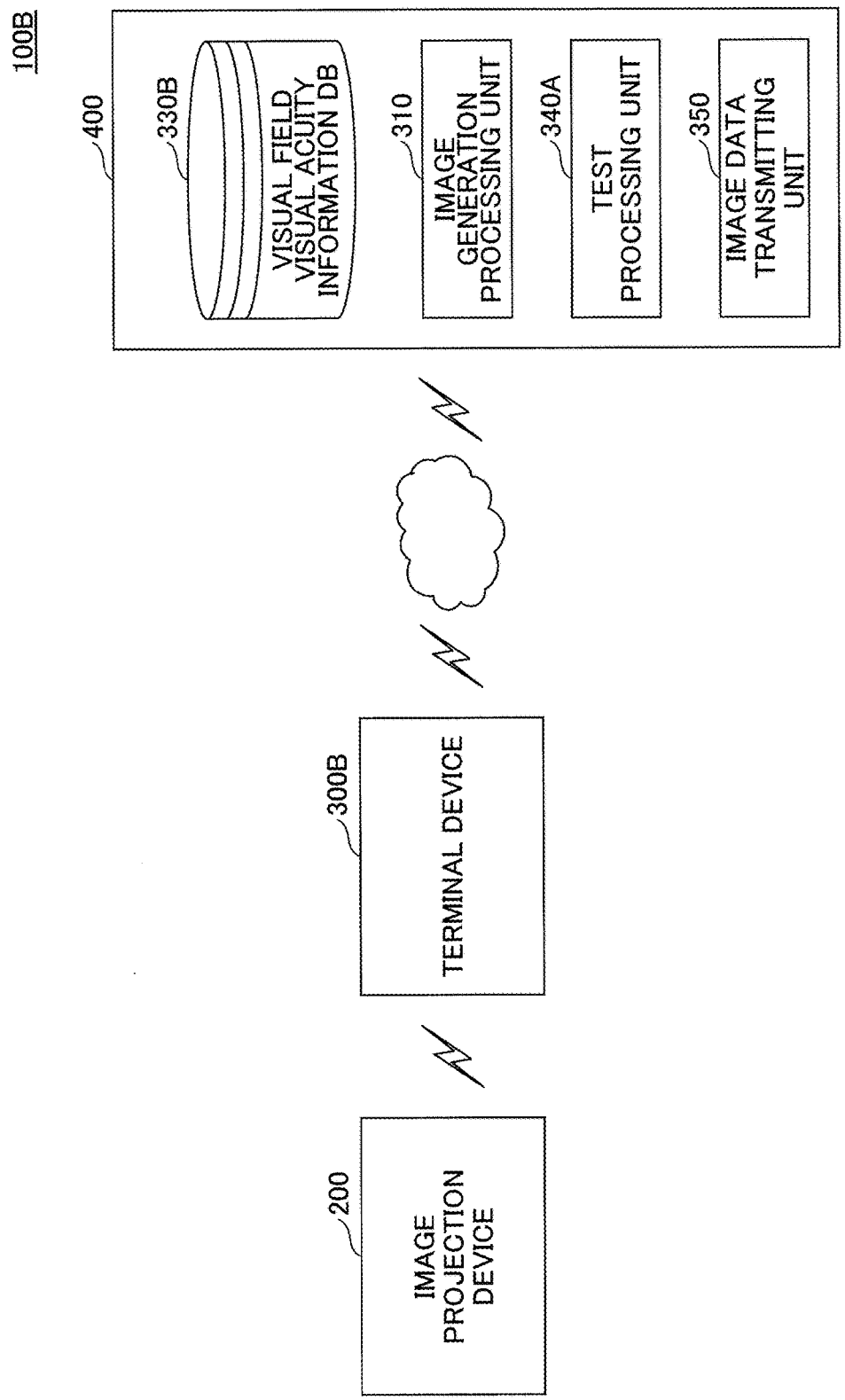
FIG. 41 is a diagram illustrating an example system configuration of an image projection system according to a third embodiment of the present invention.

FIG. 41 is a diagram showing an example system configuration of the image projection system according to the third embodiment.

The image projection system 100B according to the present embodiment includes an image projection device 200, a terminal device 300B, and a server 400. Note that although one image projection device 200 and one terminal device 300B are illustrated in FIG. 41, the number of the image projection devices 200 and the number of terminal devices 300B included in the image projection system 100B may be any number.

The terminal device 300B according to the present embodiment receives image data from the server 400 and transmits the received image data to the image projection device 200. Also, the terminal device 300B according to the present embodiment displays a screen specified by the server 400 and transmits information that has been input to the screen to the server 400.

The server 400 according to the present embodiment is connected to the terminal device 300B via a network. The server 400 includes a visual field visual acuity information database 330B, an image generation processing unit 310, a test processing unit 340A, and an image data transmitting unit 350.

In the visual field visual acuity information database 330B according to the present embodiment stores visual field information and visual acuity information input to the terminal device 300B in association with a user ID and information indicating the date/time the information was input. Specifically, for example, in the case where a plurality of terminal devices 300B exist, the visual field visual acuity information database 330B may store the visual field information table 331 and the visual acuity information table 332 input to each of the plurality of terminal devices 300B in association with a corresponding user ID.

The test processing unit 340A according to the present embodiment causes the display operation device 301 of the terminal device 300B to display a test result input screen including visual field test image data and visual acuity test image data. Further, in the test processing unit 340A according to the present embodiment, the input accepting unit 343 accepts information input to the test result input screen displayed on the terminal device 300B.

The image data transmitting unit 350 according to the present embodiment transmits the visual field test image data, the visual acuity test image data, and the image data generated by the image generation processing unit 310 to the terminal device 300B. The terminal device 300B outputs the visual field test image data, the visual acuity test image data, and the image data generated by the image generation processing unit 310 to the image projection device 200.

As described above, in the present embodiment, the test processing unit 340A and the image generation processing unit 310 are provided in the server 400, and in this way, the processing load in the terminal device 300B can be reduced.

In the present embodiment, the image generation processing unit 310 and the test processing unit 340A are provided in the server 400, but the present invention is not limited thereto.

For example, the image generation processing unit 310 and the test processing unit 340A may each be provided in separate servers 400. In this case, the visual field visual acuity information database 330B may store visual field information for each user obtained from visual field testing by the test processing unit 340A and may be configured so that the image generation processing unit 310 can refer to the stored information.

Fourth Embodiment

In the following, a fourth embodiment of the present invention will be described with reference to the drawings. The fourth embodiment is different from the second embodiment in that the server delivers an application that implements the functions of the test processing unit, the image generation processing unit, and the image output processing unit to the terminal device. In the following description of the fourth embodiment, features having substantially the same functional configuration as those of the second embodiment are given the same reference numerals as those used in the description of the second embodiment and explanations thereof will be omitted.

Figure 42:
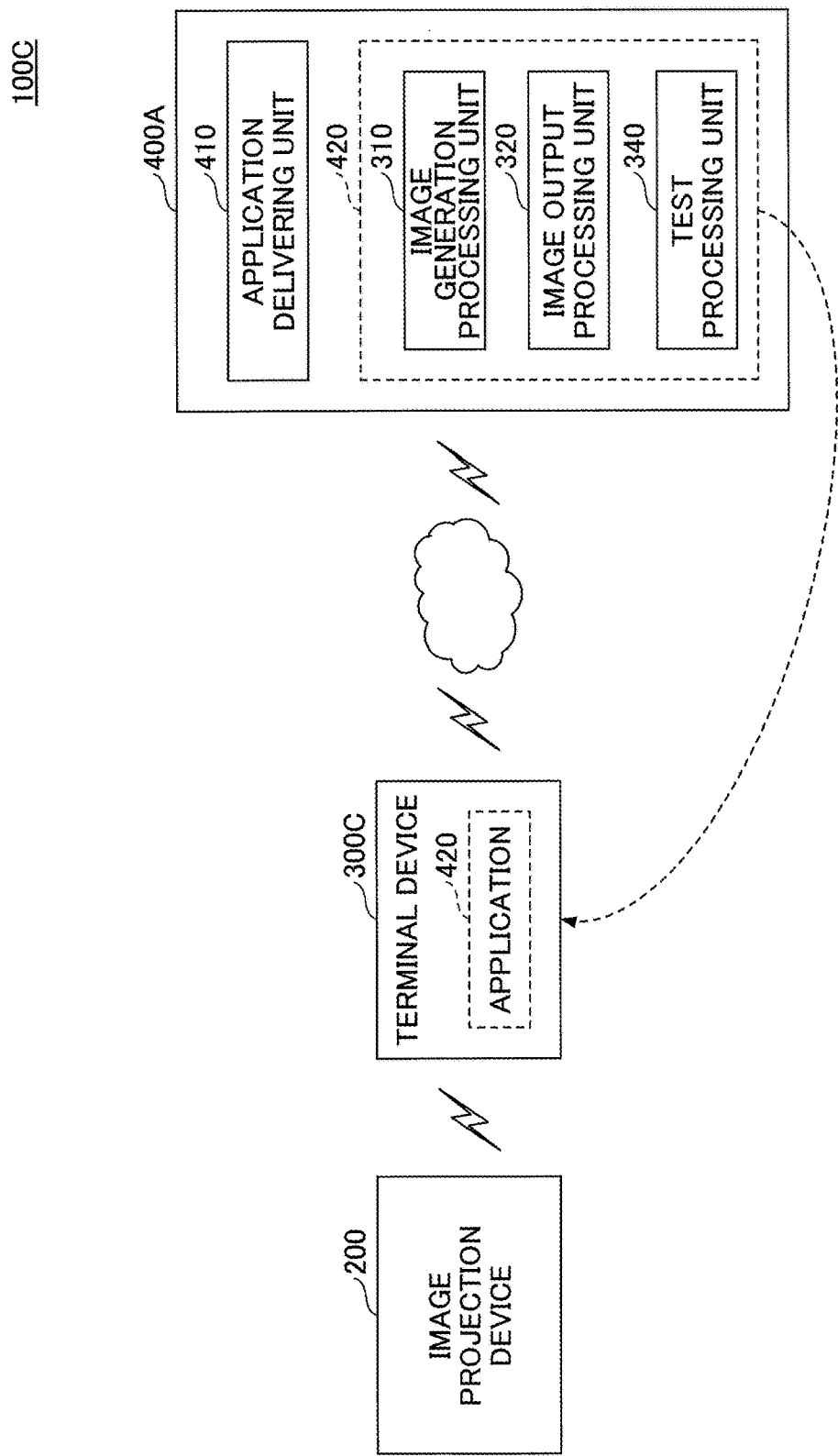
FIG. 42 is a diagram illustrating an example system configuration of an image projection system according to a fourth embodiment of the present invention.

FIG. 42 is a diagram showing an example system configuration of the image projection system according to the fourth embodiment.

The image projection system 100C according to the present embodiment includes an image projection device 200, a terminal device 300C, and a server 400A.

The server 400A according to the present embodiment includes an application delivering unit 410. The server 400A also includes an application 420 that implements the functions of the image generation processing unit 310, the image output processing unit 320, and the test processing unit 340.

In the server 400A according to the present embodiment, upon receiving a delivery request for the application 420 from the terminal device 300C, the application delivering unit 410 delivers the application 420 to the terminal device 300C that has made the delivery request.

Note that the terminal device 300C to which the application 420 has been delivered becomes the terminal device 300A including the image generation processing unit 310, the image output processing unit 320, and the test processing unit 340. Thus, in the present embodiment, the terminal device 300C that has received the application 420 from the server 400A can conduct a visual field test on its own to acquire visual field information and the visual acuity information of a user, and provide image data generated based on the acquired visual field information and visual acuity information to the image projection device 200.

Note that although the application 420 delivered by the server 400A in the present embodiment includes the functions of the image generation processing unit 310, the image output processing unit 320, and the test processing unit 340, present invention is not limited thereto. The application 420 delivered from the server 400A to the terminal device 300C may include only the functions of the image generation processing unit 310 and the image output processing unit 320, for example. In this case, the terminal device 300C may receive the application delivery from the server 400A and acquire visual field information of the user.

Fifth Embodiment

In the following, a fifth embodiment of the present invention will be described with reference to the drawings. The fifth embodiment differs from the above-described first embodiment in that the position on to which the projection information is to be projected is set up by the user. In the following description of the fifth embodiment, features having substantially the same functional configuration as those of the first embodiment are given the same reference numerals as those used in the description of the first embodiment and descriptions thereof will be omitted.

Figure 43:
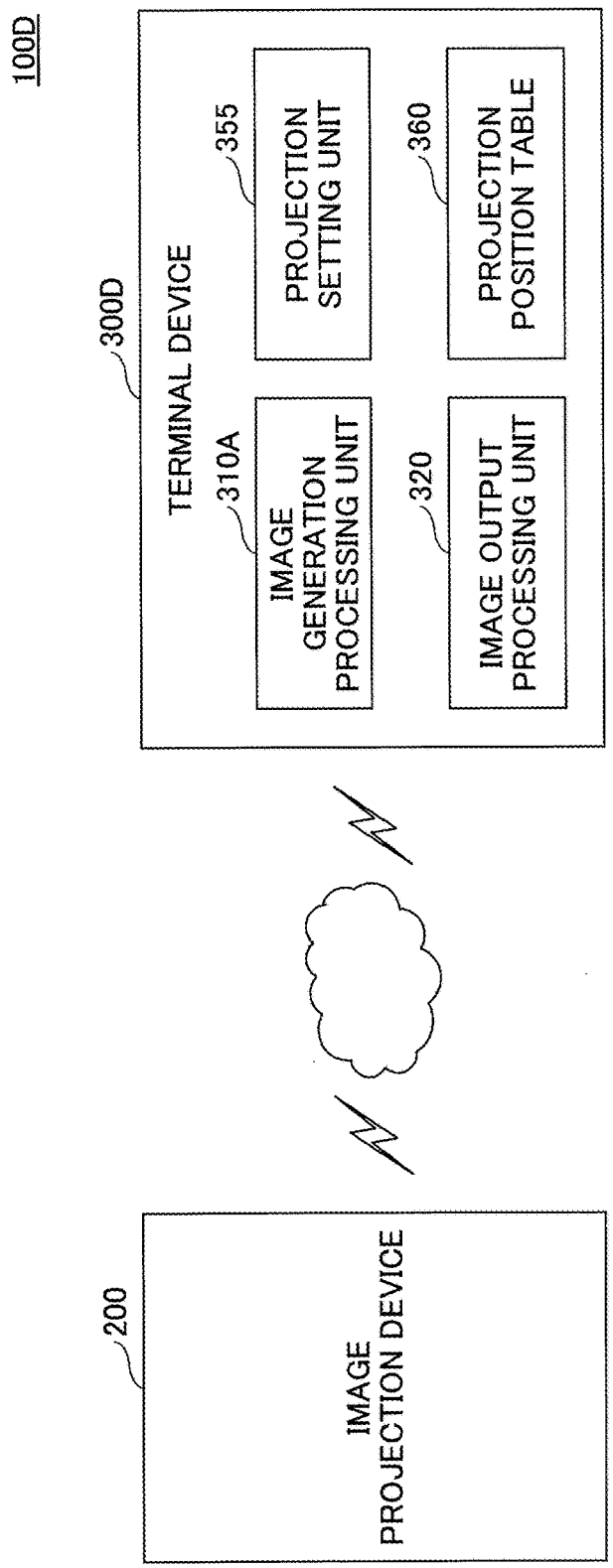
FIG. 43 is a diagram illustrating an example system configuration of an image projection system according to a fifth embodiment of the present invention.

FIG. 43 is a diagram showing an example system configuration of the image projection system according to the fifth embodiment. The image projection system 100D according to the present embodiment includes an image projection device 200 and a terminal device 300D.

The terminal device 300D according to the present embodiment includes an image generation processing unit 310A, an image output processing unit 320, a projection setting unit 355, and a projection position table 360.

The image generation processing unit 310A according to the present embodiment acquires projection position information stored in the projection position table 360 instead of acquiring visual field information. Note that the image generation processing unit 310A will be described in detail below.

The projection setting unit 355 according to the present embodiment sets up the projection location of the projection information. Specifically, the projection setting unit 355 causes the display operation device 301 of the terminal device 300D to display a setting screen for setting up the projection position of the projection information, and stores the input projection position setting in the projection position table 360.

In the projection position table 360, projection information and a projection position are associated with each other and stored for each user ID. Note that the projection position table 360 will be described in detail below.

Figures 44, 45:
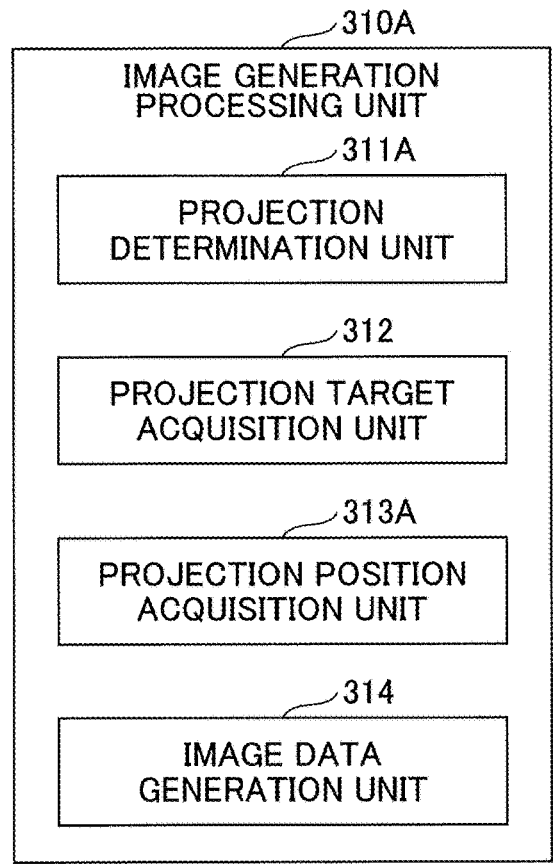
FIG. 44 is a first diagram illustrating example functions of an image generation processing unit according to the fifth embodiment.
FIG. 45 is a diagram illustrating an example of a projection position table according to the fifth embodiment.

FIG. 44 is a first diagram showing functions of the image generation processing unit according to the fifth embodiment. The image generation processing unit 310A according to the present embodiment includes a projection determination unit 311A instead of the projection request accepting unit 311 and a projection position acquisition unit 313A instead of the visual field visual acuity information acquisition unit 313.

The projection determination unit 311A determines whether to output projection information to the image projection device 200. Specifically, the projection determination unit 311A determines whether the current time corresponds to the timing at which the projection information set up in the projection position table 360 is to be projected by the image projection device 200.

The projection target acquisition unit 312 acquires projection information such as text data or image data to be projected: The projection position acquisition unit 313A acquires information indicating the projection position associated with the projection information from the projection position table 360.

In the following, the projection position table 360 according to the present embodiment will be described with reference to FIG. 45. FIG. 45 is a diagram showing an example of the projection position table according to the fifth embodiment.

The projection position table 360 according to the present embodiment includes projection information and a projection position as items of information, and these items of information are associated with each other.

The value of the item "projection information" indicates information to be projected onto the retina of a user using the image projection device 200.

The value of the item "projection position" indicates projection position information indicating the projection position of the projection information on the retina of the user. Specifically, the value of the item "projection position" may indicate coordinates of a projection area (rectangle) of the projection information including coordinates of an upper left point of the rectangle and coordinates of a lower right point of the rectangle. Note that the value of the item "projection position" may alternatively include the coordinates of the four corner points of the rectangular projection area, for example.

According to the projection position table 360 of FIG. 45, the projection information "incoming call notification" is to be projected inside a rectangle having an upper left point at coordinates (x11, y11) and a lower right point at coordinates (x21, y21).

Figure 46:
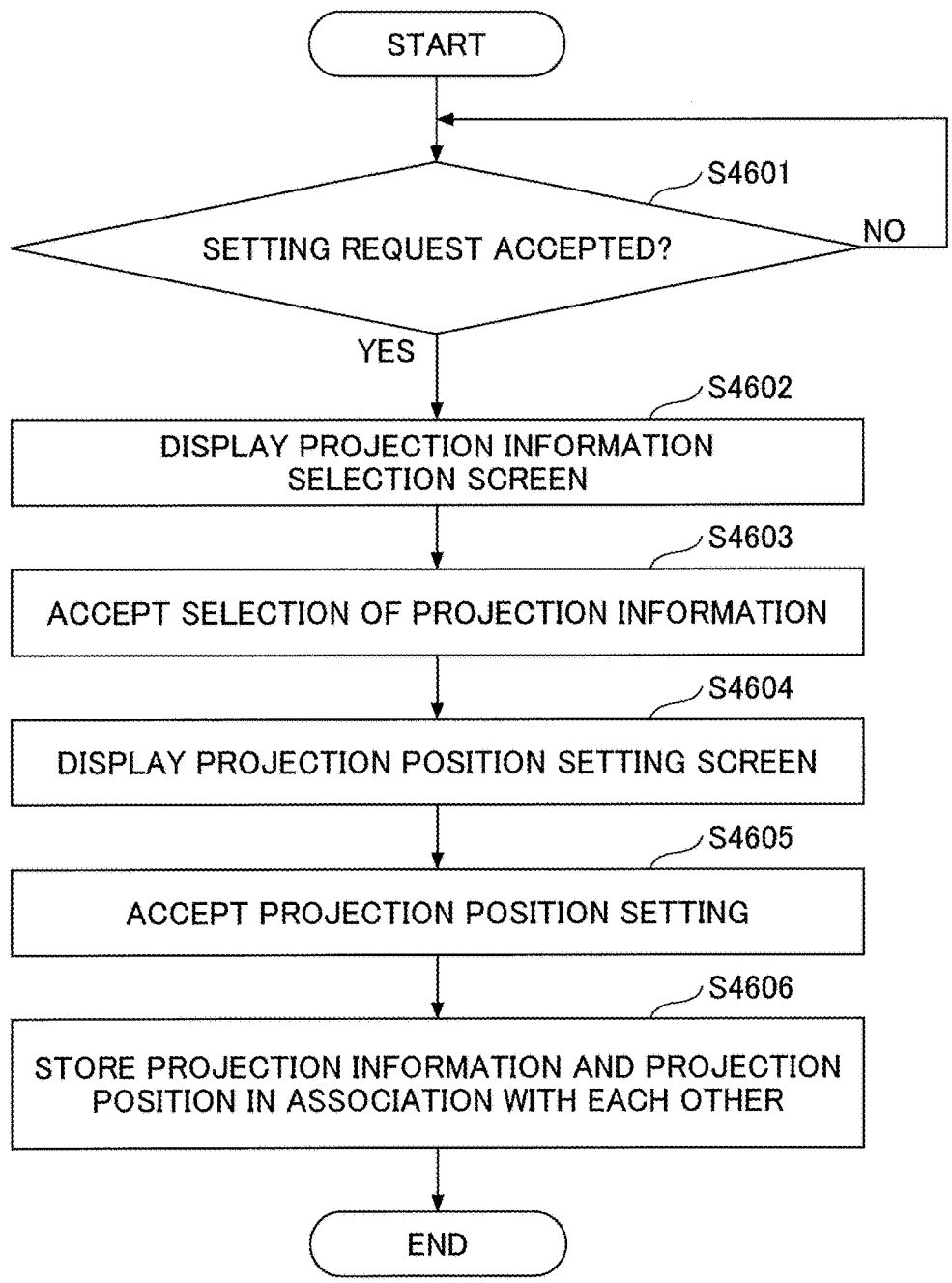
FIG. 46 is a flowchart illustrating example process operations implemented by a projection setting unit according to the fifth embodiment.

In the following, process operations of the projection setting unit 355 according to the present embodiment will be described with reference to FIG. 46. FIG. 46 is a flowchart showing process operations of the projection setting unit according to the fifth embodiment.

The projection setting unit 355 according to the present embodiment determines whether a setting request for setting up the projection position of projection information has been accepted (step S4601).

In step S4601, if it is determined that a setting request has not been accepted, the projection setting unit 355 waits until a setting request is accepted.

In step S4601, if it is determined that a setting request has been accepted, the projection setting unit 355 causes the display operation device 301 of the terminal device 300D to display a projection information selection screen (step S4602), and accepts a selection of projection information via the projection information selection screen (step S4603).

Then, the projection setting unit 355 displays a projection position setting screen for setting up the projection position of the selected projection information (step S4604), and accepts a projection position setting (step S4605).

Then, the projection setting unit 355 stores the selected projection information and position information indicating the projection position that has been set up in the projection position table 360 (step S4606), and ends the process.

Figure 47:
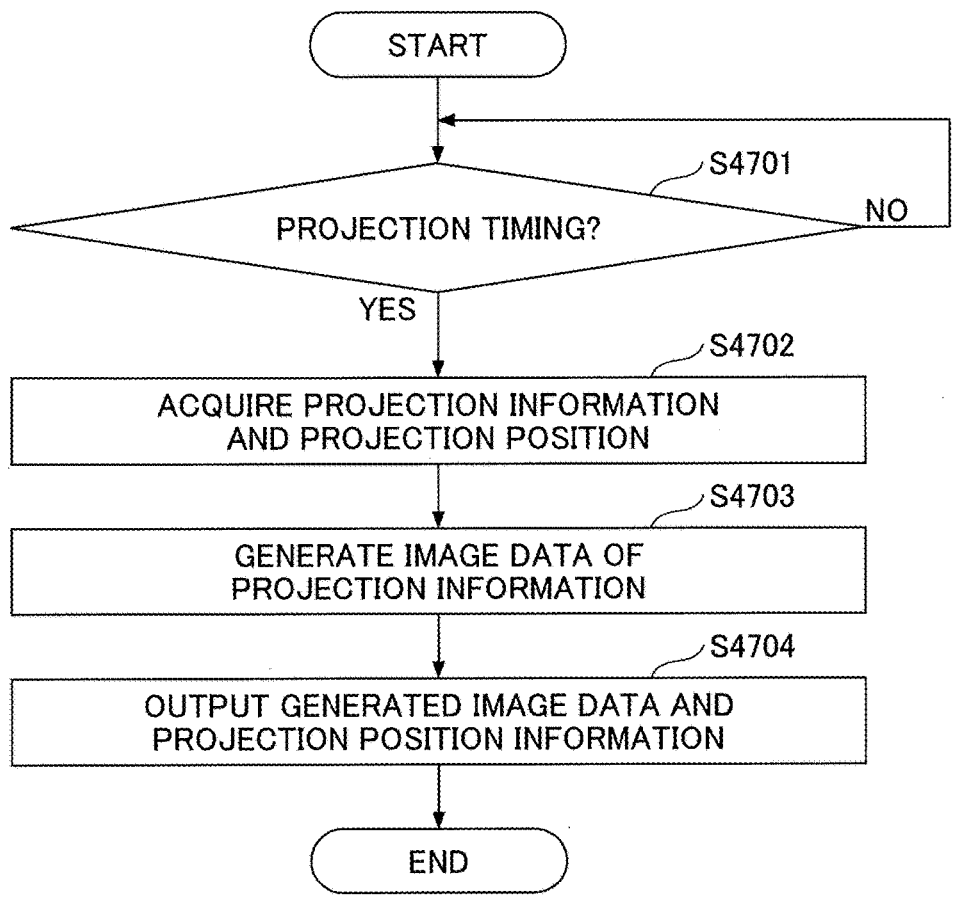
FIG. 47 is a flowchart illustrating example process operations implemented by the image generation processing unit according to the fifth embodiment.

In the following, process operations of the image generation processing unit 310A according to the present embodiment will be described with reference to FIG. 47. FIG. 47 is a flowchart showing process operations of the image generation processing unit according to the fifth embodiment. In the image generation processing unit 310A according to the present embodiment, the projection determination unit 311A determines whether the current time corresponds to the projection timing of projection information (step S4701). Specifically, for example, in the case where the projection information is an incoming call notification, the projection determination unit 311A determines that it is currently the projection timing of the projection information when the terminal device 300D receives an incoming call notification.

In step S4701, if it is not the projection timing, the projection determination unit 311A waits until the projection timing arrives.

In step S4701, if it is currently the projection timing, the image generation processing unit 310A refers to the projection position table 360 and acquires the projection position information corresponding to the projection information. Also, the projection target acquisition unit 312 of the image generation processing unit 310A acquires the projection information to be projected (step S4702).

Then, the image data generation unit 314 of the image generation processing unit 310A generates image data of the image indicating the projection information (step S4703). Then, the image data generation unit 314 outputs the generated image data to the image output processing unit 320 (step S4704) after which the process is ended. The image data output to the image output processing unit 320 is transmitted to the image projection device 200 by the image output processing unit 320.

Figure 48A:
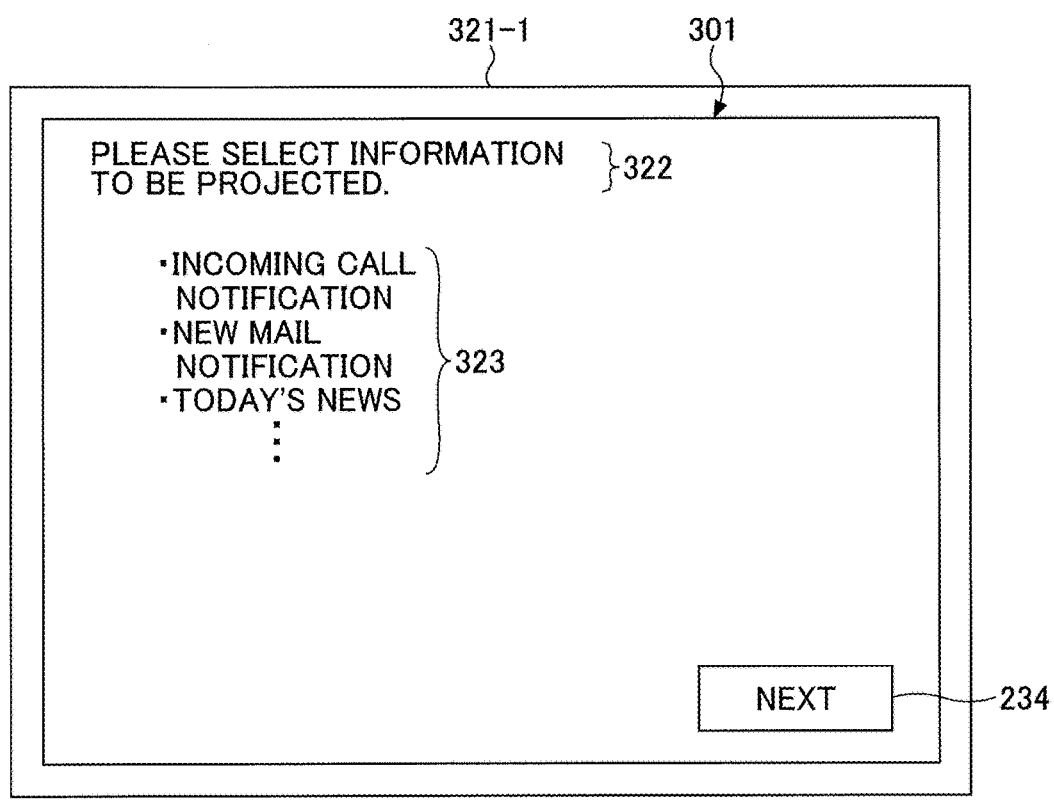
FIG. 48A is a diagram illustrating an example selection screen for prompting selection of projection information according to the fifth embodiment.

In the following, the projection position setting screen according to the present embodiment will be described with reference to FIGS. 48A and 48B. FIG. 48A is a diagram showing an example of a projection information selection screen according to the fifth embodiment, and FIG. 48B is a diagram showing an example of a projection position setting screen for the selected projection information.

The position information selection screen 321-1 shown in FIG. 48A displays a message 322 prompting selection of projection information, a projection information list 323, and a button 234 for transitioning the position information selection screen 321-1 to a projection position setting screen 321-2.

Figure 48B:
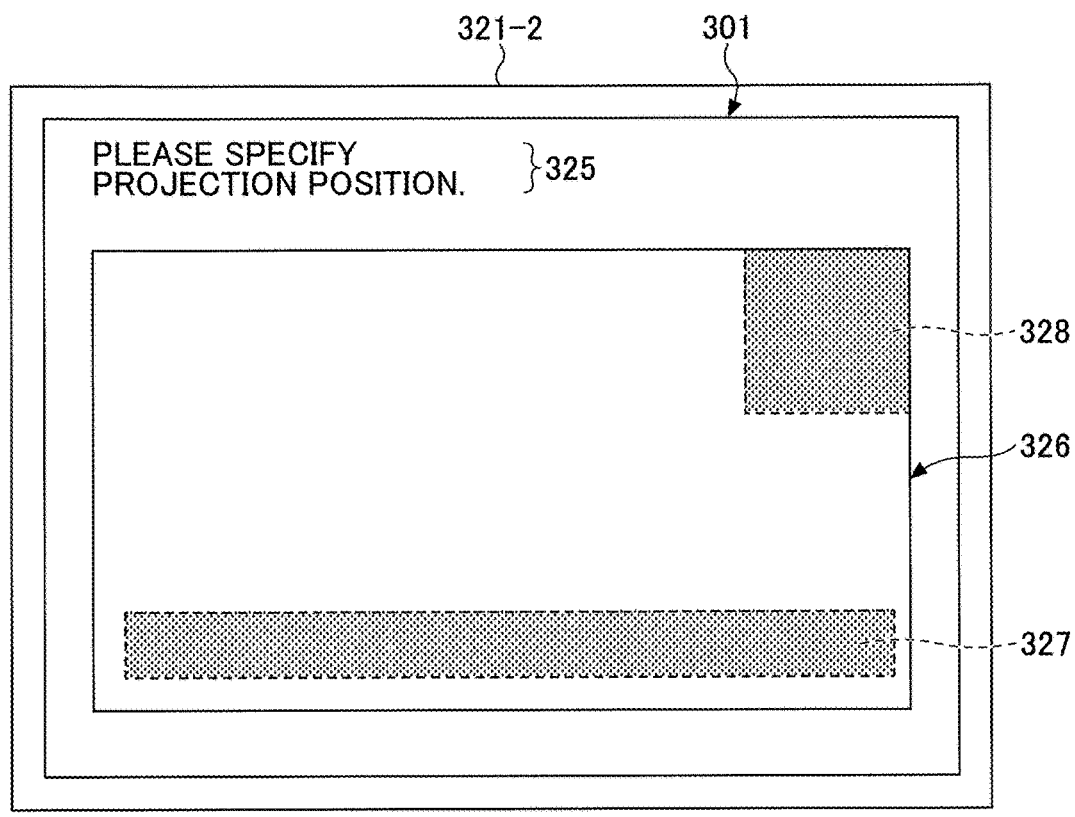
FIG. 48B is a diagram illustrating an example setting screen for setting a projection position of projection information.

When projection information is selected from the projection information list 323 and the button 324 is operated on the position information selection screen 321-1, the terminal device 300D causes the projection information selection screen 321-1 displayed on the display operation device 301 to transition to the projection position setting screen 321-2 as shown in FIG. 48B.

The projection position setting screen 321-2 displays a message 325 prompting specification of a projection position and an image 326 indicating a projection area covered by the image projection device 200.

When the projection information "incoming call notification" is selected on the position information selection screen 321-1 and an area 327 is specified on the projection position setting screen 321-2, for example, the projection setting unit 355 according to the present embodiment stores the projection information "incoming call notification" and coordinate information specifying the area 327 in association with each other in the projection position table 360.

Also, for example, when projection information "clock" is selected on the projection information selection screen 321-1 and an area 328 is specified on the projection position setting screen 321-2, the projection setting unit 355 stores the projection information "clock" and coordinate information specifying the area 328 in association with each other in the projection position table 360.

Note that the projection position may also be specified, for example, by the user touching a desired area on the image 326 on the projection position setting screen 321-2 or encircling a desired area with a finger.

Also, according to an aspect of the present embodiment, the terminal device 300D may hold visual acuity information of a user, and the image generation processing unit 310A may acquire the visual acuity information of the user in addition to projection information and projection position to thereby adjust the size of characters, numbers, and/or symbols included in the projection information to be projected according to the visual acuity information of the user.

Figure 49:
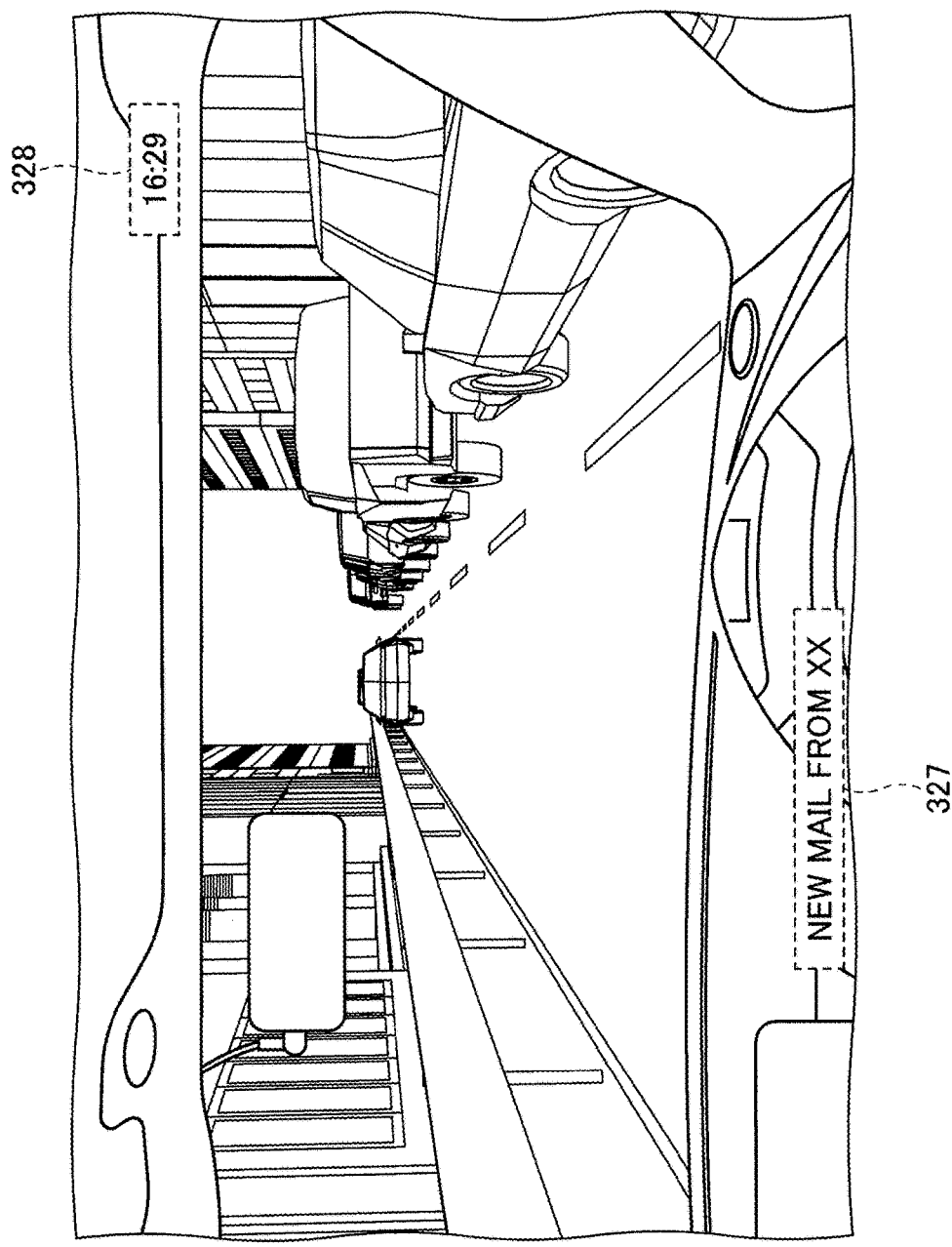
FIG. 49 is a diagram illustrating an example projection of projection information to a specified position.

FIG. 49 is a diagram showing an example image having projection information projected onto specified projection positions. FIG. 49 shows a part of the visual filed of a user.

It can be appreciated that in the example of FIG. 49, an incoming call notification is projected onto the position of an area 327 of the visual field so that the incoming call notification can be visually perceived, and a clock is projected onto the position of an area 328 of the visual field so that the clock can be visually perceived.

As described above, according to an aspect of the present embodiment, projection information can be projected onto a desired position on the retina of a user. Thus, according to an aspect of the present embodiment, the user may not have to move his/her gaze or adjust his/her focus in order to view the projected projection information.

Thus, according to an aspect of the present embodiment, for example, even when the user is in a situation that makes it difficult for the user to turn his/her gaze away from a fixation target, the user may still be able to visually perceive the projection information. For example, the image projection system 100D according to the present embodiment may be used by a driver of a moving vehicle such as an automobile, by having the driver wear the image projection device 200 and projecting traffic information onto a predetermined position of the visual field of the driver so that the driver may be able to visually perceive the traffic information without moving his/her gaze.

Also, the image projection system 100D according to the present embodiment may be used by a surgeon that is performing surgery, for example, by having the surgeon wear the image projection device 200 and projecting information that needs to be referenced during surgery, such as numerical values and the like, so that the surgeon may be able to visually perceive the required information without having to turn his/her gaze away from the operative field.

Note that the image generation processing unit 310A, the projection setting unit 355, and the projection position table 360 according to the present embodiment may be provided in an external server outside the terminal device 300. Further, the image generation processing unit 310A and the projection setting unit 355 according to the present embodiment may be delivered as an application from the external server to the terminal device 300, for example.

In the following, another example of the image generation processing unit of the terminal device 300D according to the present embodiment will be described with reference to FIG. 50.

Figure 50:
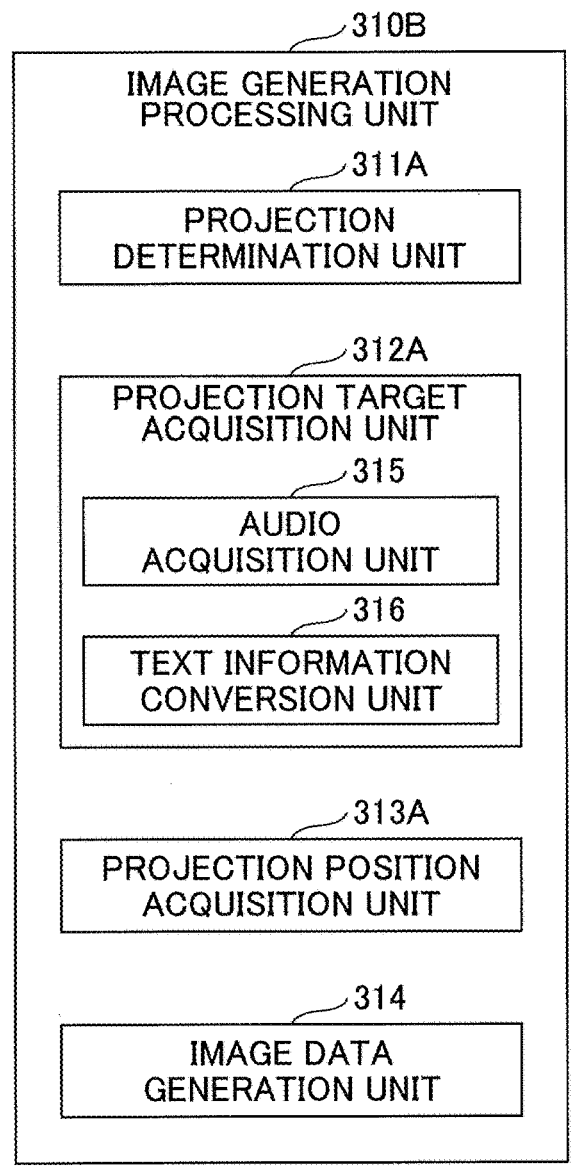
FIG. 50 is a second diagram illustrating example functions of the image generation processing unit according to the fifth embodiment.

FIG. 50 is a second diagram showing example functions of the image generation processing unit according to the fifth embodiment. The image generation processing unit 310B shown in FIG. 50 includes a projection determination unit 311A, a projection target acquisition unit 312A, a projection position acquisition unit 313A, and an image data generation unit 314. The image generation processing unit 310B converts audio from outside that has been input into character information, and used the converted character information as projection information.

The projection target acquisition unit 312A according to the present embodiment includes an audio acquisition unit 315 and a character information conversion unit 316.

The audio acquisition unit 315 acquires audio input via an audio input device such as a microphone of the terminal device 300D, for example. The character information conversion unit 316 analyzes the audio acquired by the audio acquisition unit 315 and converts the acquired audio into character information.

In the image generation processing unit 310B according to the present embodiment, when the audio acquisition unit 315 acquires audio from the outside, the character information conversion unit 316 converts the acquired audio into text information as projection information. By projecting such projection information onto a given visual field of a user, the user may be able to visually perceive the audio as text.

According to an aspect of the present embodiment, by using such a configuration, even a user having a hearing impairment and a visual impairment may be able to recognize audio information. By applying such a configuration to audio guidance at an art museum or audio guidance for a kabuki performance, for example, information that has been difficult for a user to acquire due to some impairment may be acquired by the user.

Note that the system configuration as described above may also be used by a person with no impairments. That is, because audio information can be converted into text information and the text information can be moved and projected onto a desired position of the visual field in the present system, the text information converted from the audio information can be projected onto a desired position that can be visually perceived without interfering with other views of interest.

Sixth Embodiment

In the following, a sixth embodiment of the present invention will be described with reference to the drawings. Note that the shape of the mirrors in the image projection device according to the sixth embodiment differs from that of the first embodiment. In the following description of the sixth embodiment, only features that differ from those of the first embodiment will be explained, and features having the same functional configuration as those of the first embodiment are given the same reference numerals as those used in the description of the first embodiment and explanations thereof will be omitted.

Figure 51:
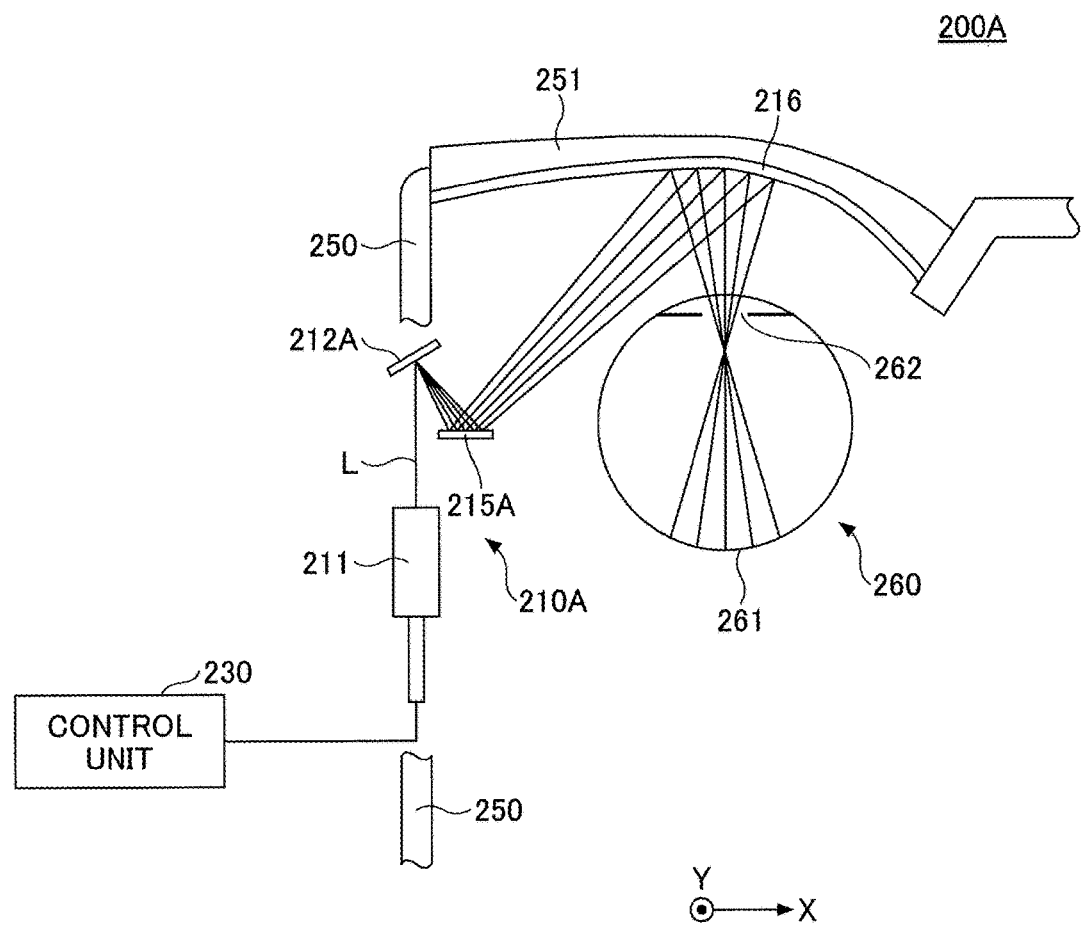
FIG. 51 is a top view of an image projection device according to a sixth embodiment of the present invention.

FIG. 51 is a top view of the image projection device according to the sixth embodiment. The image projection device 200A according to the present embodiment can be used in the above-described image projection systems according to the first to fifth embodiments.

The image projection device 200A according to the present embodiment includes a projection unit 210A and a control unit 230. The projection unit 210A according to the present embodiment includes a light source 211, a scanning mirror 212A, a reflection mirror 215A, and a projection mirror 216. Note that the projection unit 210A according to the present embodiment differs from the projection unit 210 according to the first embodiment in that it does not include the mirror 213 and the mirror 214, but includes the scanning mirror 212A instead of the scanning mirror 212, and the reflection mirror 215A instead of the reflection mirror 215.

In the image projection device 200A according to the present embodiment, it is assumed that X direction represents the traveling direction within the projection mirror 216 of light beams incident on the projection mirror 216, and Y direction represents a direction orthogonal to the X direction in the projection mirror 216.

The scanning mirror 212A may be an MEMS mirror, for example, and scans laser light (light beam) L emitted from the light source 211 in two-dimensional directions in the horizontal direction and the vertical direction. Also, the scanning mirror 212A scans the light beam L emitted from the light source 211 two-dimensionally as projection light for projecting an image onto the retina 261 of the eyeball 260 of the user.

The reflection mirror 215A reflects the light beam L scanned by the scanning mirror 212A toward the lens 251.

The projection mirror 216 having a free-form surface is provided on the surface of the lens 251 toward the eyeball 260 of the user. The projection mirror 216 projects an image onto the retina 261 by irradiating the retina 261 of the eyeball 260 with the light beam L scanned by the scanning mirror 212A and reflected by the reflection mirror 215A. That is, the user can perceive the image by the afterimage effect of the laser light projected onto the retina 261. The projection mirror 216 is designed so that the convergence position of the light beam L scanned by the scanning mirror 212A will be at the pupil 262 of the eyeball 260. The light beam L is incident on the projection mirror 216 substantially from the lateral side (i.e., from substantially the −X direction).

According to an aspect of the present embodiment, by increasing the curvature of the free-form surface of the projection mirror 216, the distance from the reflection mirror 215A to the convergence position at the pupil 262 can be shortened, and the image projection device 200A can be reduced in size.

Figure 52:
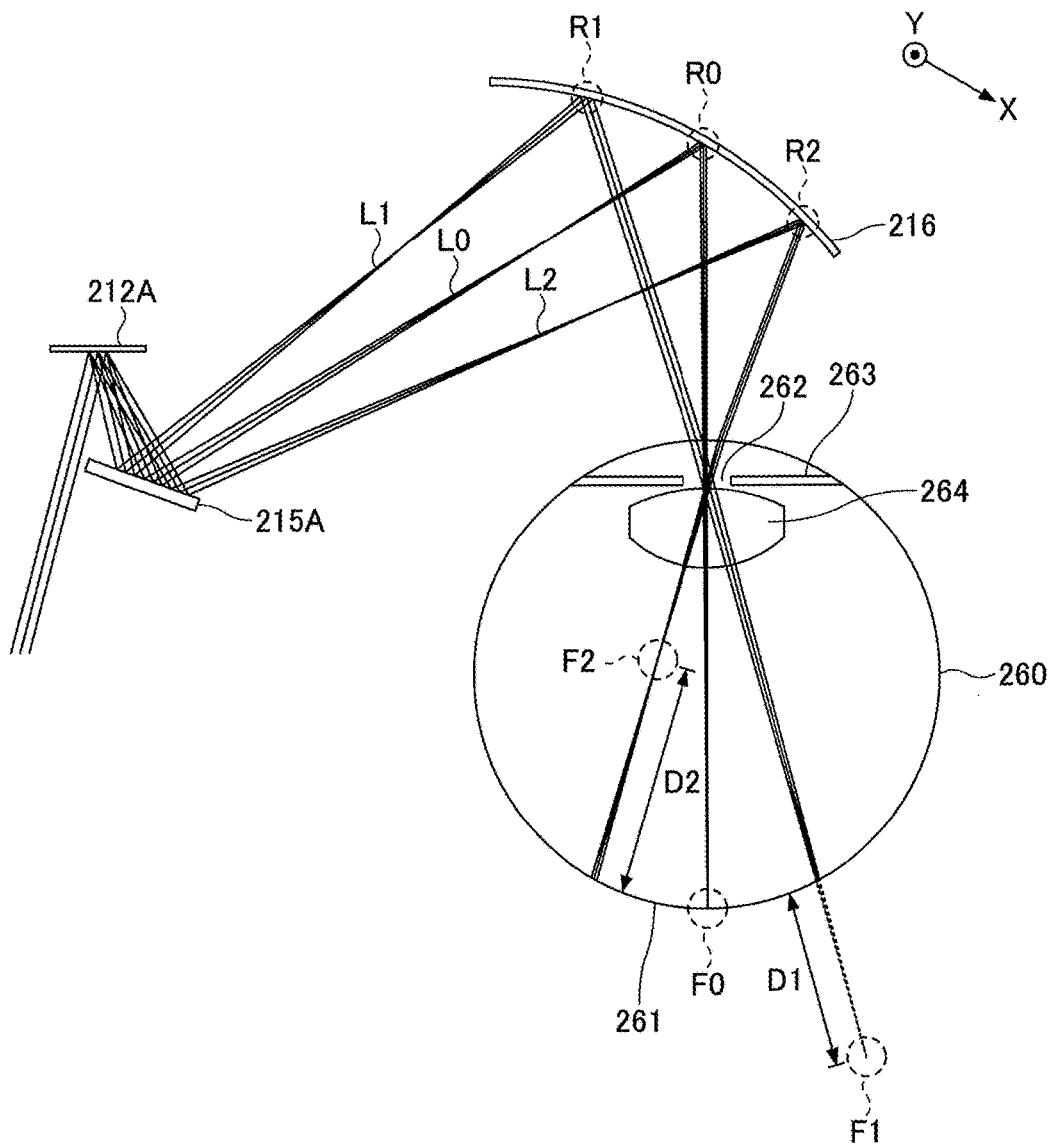
FIG. 52 is a diagram illustrating optical paths of light beams in an image projection device according to a comparative example.

FIG. 52 is a diagram showing optical paths of light beams in an image projection device according to a comparative example. In FIG. 52, light beams L0 to L2 are scanned in the horizontal direction by the scanning mirror 212A, and are projected onto the projection mirror 216 from the −X direction. The light beam L0 is a light beam corresponding to the center of an image, and the light beams L1 and L2 are light beams corresponding to the edges of the image. The light beams L0 to L2 are reflected by the projection mirror 216 at regions R0 to R2 of the projection mirror 216, respectively. The reflected light beams L0 to L2 converge at the pupil 262 located at the center of the iris 263, pass through the crystalline lens 264, and reach the retina 261. The region R0 is a region that reflects the light beam L0 corresponding to the center of the image. The region R1 is a region toward the −X direction side of the region R0 (incidence direction side of the light beams L0 to L2). The region R2 is a region toward +X direction side from the region R0. To achieve the Maxwellian view, the light beams L0 to L2 intersect with each other near the pupil 262. However, focal positions F0 to F2 of the light beams L0 to L2 deviate from the position of the retina 261.

In FIG. 52, the light beam L0 reflected by the projection mirror 216 enters the crystalline lens 264 as substantially parallel light and is focused in the vicinity of the retina 261. The light beam L1 reflected by the projection mirror 216 is incident on the crystalline lens 264 as diffused light. As such, the light beam L1 is focused at a point farther away from the retina 261. The light beam L2 reflected by the projection mirror 216 is incident on the crystalline lens 264 as convergent light. As such, the light beam L2 is focused at a point before reaching the retina 261. As described above, when the light beam L0 is focused in the vicinity of the retina 261, the focal position F1 of the light beam L1 will be at a position farther away from the projection mirror 216 than the position of the retina 261. That is, the focal position F1 is at a distance D1 away from the retina 261. The focal position F2 is located closer to the projection mirror 216 than the retina 261. That is the focal position F2 is at a distance D2 away from the retina 261.

The focal positions F0 to F2 differ from one another in the above-described manner because the projection mirror 216 is a free-form surface mirror. That is, when converging the light beams L0 to L2 incident on the projection mirror 216 from the −X direction side at the pupil 262, the focal positions F0 to F2 of the light beams L0 to L2 may vary due to the differences in the curvatures of the regions R0 to R2 of the projection mirror 216 in the X direction and/or differences in the optical paths of the light beams L0 to L2. For example, the curvature of the region R2 is greater than the curvature of the region R1. That is, the region R2 has a higher light gathering power than the region R1. As such, the focal position F2 will be on the light source side with respect to the focal position F1. Also, when the projection mirror 216 is arranged parallel to the face, the optical path of the light beam L2 will be longer than the optical path of the light beam L1. As a result, the focal position F2 will be further toward the light source side with respect to the focal position F1. As described above, in the comparative example, when the light beams L0 to L2 are converged in the vicinity of the pupil 262 for achieving a Maxwellian view, an image projected on the retina 261 may include an area with a focal position substantially deviating from the position of the retina 261. Note that the optical system in the Y direction is substantially symmetrical with respect to the X axis, and unlike the X direction, deviation of the focal position in the Y direction is not likely to occur.

Figure 53:
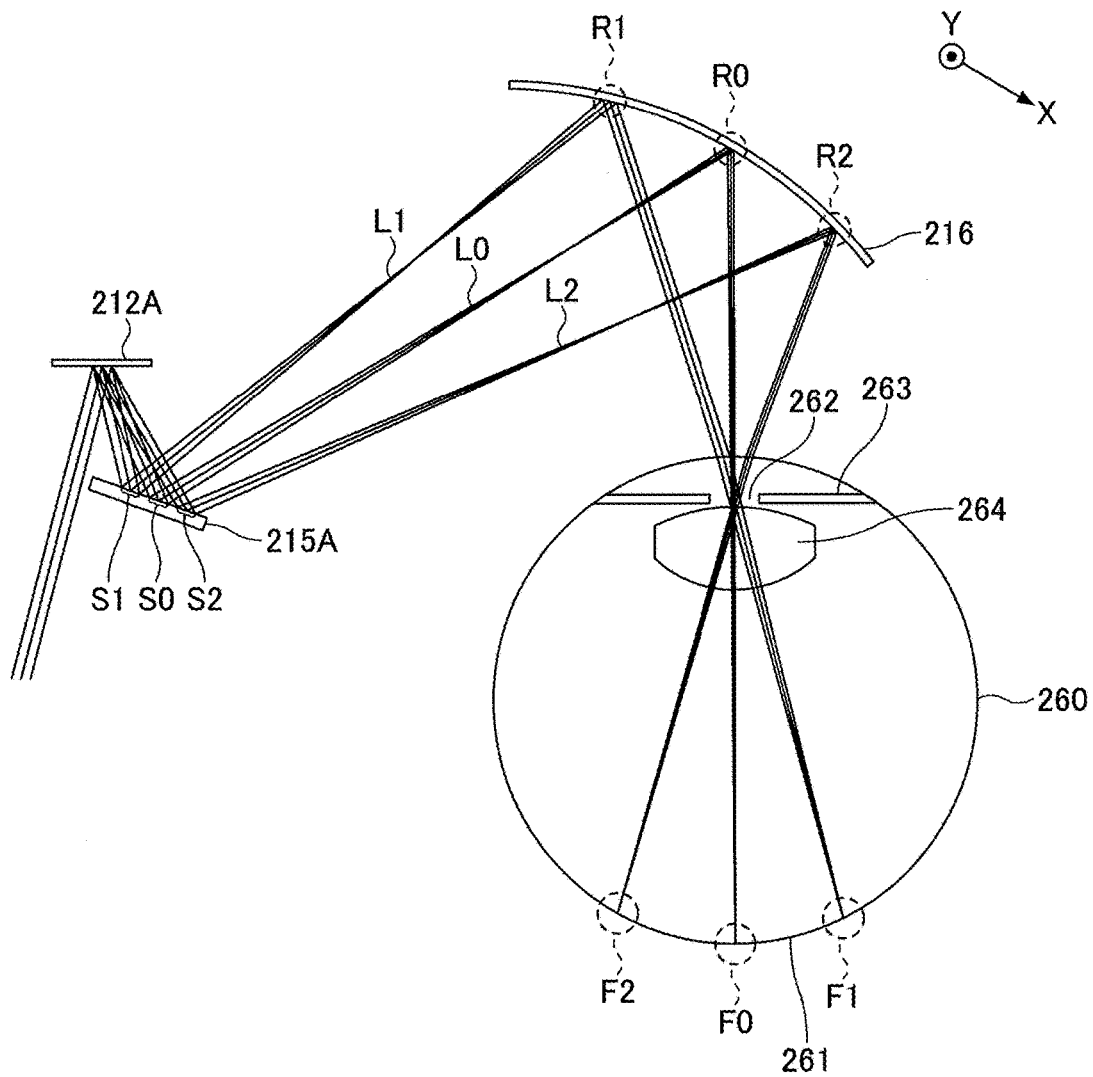
FIG. 53 is a diagram illustrating optical paths of light beams in the image projection device according to the sixth embodiment.
Figure 54:
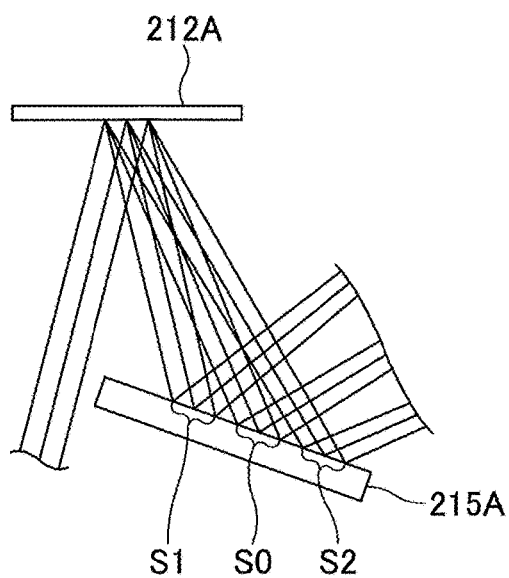
FIG. 54 is an enlarged view of the vicinity of a reflection mirror shown in FIG. 53.

In this respect, according to an aspect of the present embodiment, the reflection mirror 215A is used as an optical component. FIG. 53 is a diagram showing the optical path of the light beams in the image projection device according to the sixth embodiment, and FIG. 54 is an enlarged view of the vicinity of the reflection mirror of FIG. 53. As shown in FIGS. 53 and 54, the light beams L0 to L2 irradiated onto the regions R0 to R2 of the projection mirror 216 are reflected by the reflection mirror 215A at regions S0 to S2, respectively. The reflection mirror 215A has a free-form surface.

Note that other configuration features of the present embodiment may be the same as those of the above-described comparative example, and as such, descriptions thereof will be omitted.

Figure 55:
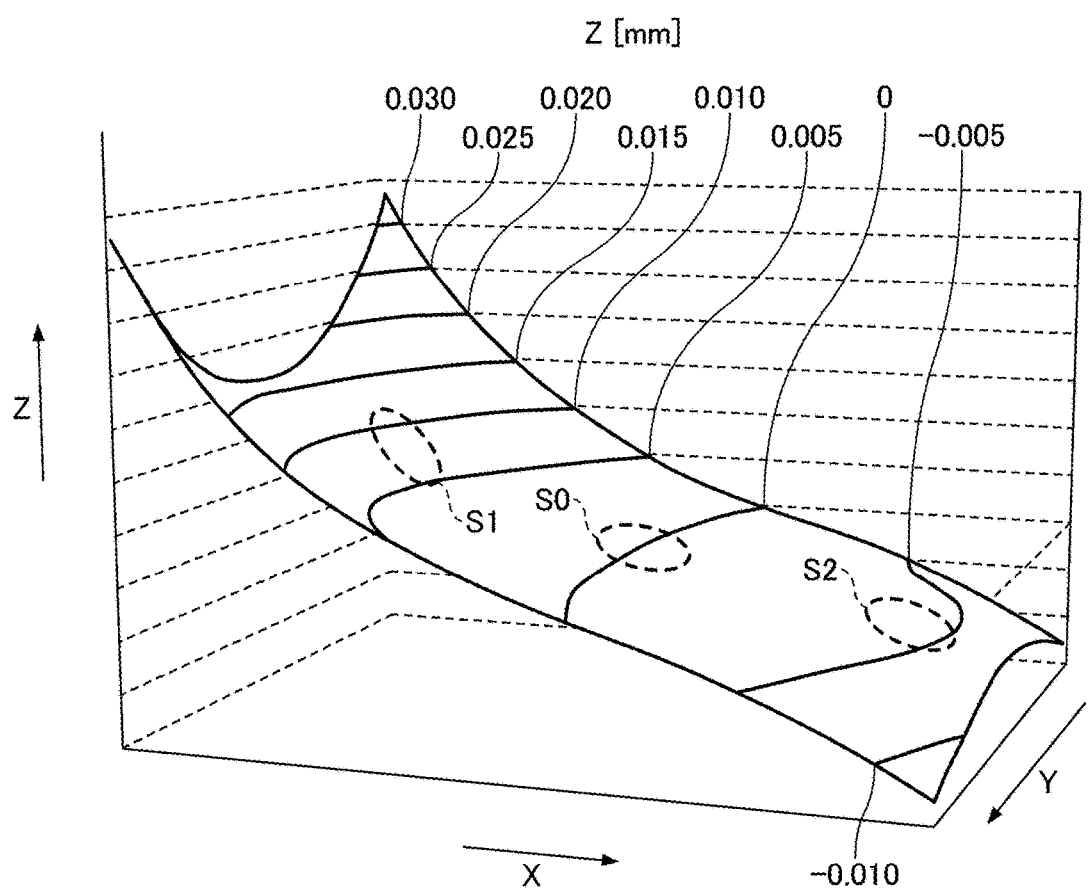
FIG. 55 is a perspective view of an unevenness of the reflection mirror surface according to the sixth embodiment.
Figure 56:
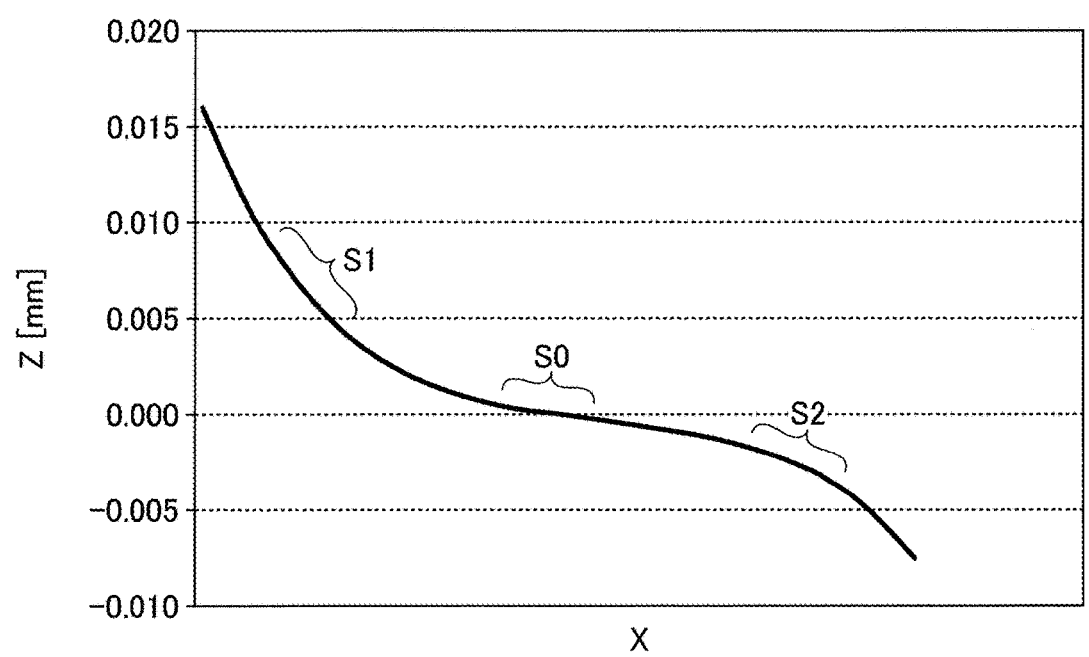
FIG. 56 is a diagram illustrating a distribution of the height Z of the reflection mirror in the X direction.

FIG. 55 is a perspective view of unevenness of the reflection mirror surface according to the sixth embodiment, and FIG. 56 is a graph showing a distribution of the height Z of the reflection mirror in the X direction. The X direction and the Y direction are directions corresponding to the X direction and the Y direction of the projection mirror 216. The height of the reflection mirror 215A is the Z direction.

In FIG. 55, the Z direction represents an enlarged view of the unevenness of the surface of the reflection mirror 215A. As shown in FIGS. 55 and 56, in the region S0, the surface of the reflection mirror 215A is substantially flat. In the region S1, the surface of the reflection mirror 215A is concave. In the region S2, the surface of the reflection mirror 215A is convex. As such, in the region S0, the light gathering power is substantially 0, the light gathering power is positive in the region S1, and the light gathering power is negative in the region S2. Thus, the focal positions F0 of the light beam L0 does not change from the comparative example. The focal position F1 of the light beam L1 moves closer toward the light source as compared with the comparative example shown in FIG. 52, and the focal position F2 of the light beam L2 moves farther away from the light source as compared with the comparative example shown in FIG. 52. In this way, the focal positions F0 to F2 may be in the vicinity of the retina 261.

In the present embodiment, Z on the surface of the reflection mirror 215A is a free-form surface represented by the following equation.

$$Z = \Sigma a_{ij} \times X^i \times Y^j$$

The origin (X=0, Y=0) corresponds to the center of the image and may correspond to the vicinity of the region S0, for example. Also, $a_{ij}$ is a coefficient. To create light gathering power differences in the X direction, at least one of the coefficients $a_{ij}$ of the terms in which i is an odd number is set to a finite value (other than 0).

The light gathering power in the Y direction of the projection mirror 216 is symmetrical with respect to the X axis. Thus, the coefficient $a_{ij}$ of the term with j being an odd number is set to 0 (zero).

In the present embodiment, for example, the coefficients $a_{30}$ and $a_{12}$ are set to finite values. As a result, a free curved surface as shown in FIGS. 55 and 56 can be obtained. In order to further adjust the free-form surface of the reflection mirror 215A, the coefficients $a_{10}$ and/or $a_0$ may also be set to a finite value. Further, a higher-order coefficient may be set to a finite value.

By setting up the curved surface of the reflection mirror 215A into a free-form surface corresponding to the free-form surface of the projection mirror 216 including a combination of a concave surface, a convex surface, and a flat surface as described above, the image projection device 200A may have an optical system that is compact in size and less susceptible to distortions.

Although the present invention has been described above with respect to illustrative embodiments, the present invention is not limited to the above embodiments, and numerous variations and modifications may be made without departing from the scope of the present invention.

The present application is based on and claims the benefit of priority of Japanese Patent Application No. 2016-115046 filed on Jun. 9, 2016 and Japanese Patent Application No.

2017-111151 filed on Jun. 5, 2017, the entire contents of which are herein incorporated by reference.

DESCRIPTION OF THE REFERENCE NUMERALS 100, 100A, 100B image projection system
200 image projection device
300, 300A, 300B, 300C, 300D terminal device
310, 310A image generation processing unit
311 projection request accepting unit
311A projection determination unit
312 projection target acquisition unit
313 visual field visual acuity information acquisition unit
313A projection position acquisition unit
314 image data generation unit
320 image output processing unit
330, 330A visual field visual acuity information storage unit
330B visual field visual acuity information database
331 visual field information table
332 visual acuity information table
340 test processing unit
341 image data holding unit
342 display control unit
343 test result storage unit
355 projection setting Unit
360 projection position table
400 server
410 application delivering unit

The invention claimed is:

1. An image projection system comprising:
an image projection device; and
a terminal device communicating with the image projection device;
wherein the terminal device includes
a first hardware memory that stores a first program, and
a first processor that executes the first program to perform a first process including
holding projection information to be projected by the image projection device,
causing a display device of the terminal device to display a setting screen for prompting a user to specify a position on a retina of the user at which the projection information is to be projected, and associating position information indicating the position specified by the user at the setting screen with the projection information,
acquiring the position information from a storage device that stores the position information,
generating image data of an image that projects the projection information at the position indicated by the position information, and
outputting the image data to the image projection device; and
Wherein the image projection device includes
a light source that emits a light beam,
a scanning mirror,
a second hardware memory that stores a second program, and
a second processor that executes the second program to perform a second process including
inputting the image data from the terminal device,
generating an image light beam based on the input image data and controlling emission of the image light beam from the light source, and
causing the scanning mirror to scan the image light beam and thereby projecting the image light beam onto the retina of an eyeball of the user as the image represented by the image data.

2. An image projection system comprising:
an image projection device; and
a terminal device communicating with the image projection device;
wherein the terminal device includes
a storage device that stores position information indicating a position on a retina of a user at which projection information is to be projected by the image projection device, the position information indicating a position of an identifier of a region of a test image that has been visually perceived by the user from the test image that has been projected onto the retina of the user, the test image being divided into a plurality of regions including a plurality of identifiers associated with position information of the plurality of regions,
a first hardware memory that stores a first program, and
a first processor that executes the first program to perform a first process including
holding the projection information,
acquiring the position information from the storage device,
generating image data of an image that projects the projection information at the position indicated by the position information, and
outputting the image data to the image projection device; and
wherein the image projection device includes
a light source that emits a light beam,
a scanning mirror,
a second hardware memory that stores a second program, and
a second processor that executes the second program to perform a second process including
inputting the image data from the terminal device,
generating an image light beam based on the input image data and controlling emission of the image light beam from the light source, and
causing the scanning mirror to scan the image light beam and thereby projecting the image light beam onto the retina of an eyeball of the user as the image represented by the image data.

3. The image projection system according to claim 1 or 2, wherein
the first process further includes
generating image data of an image indicating the projection information, and
outputting the image data of the image indicating the projection information and the position information to the image projection device; and
the second process further includes
projecting the image light beam based on the image data at the position on the retina of the user indicated by the position information as the image indicating the projection information.

4. The image projection system according to claim 3, wherein
the storage device stores information indicating a visual acuity of the user; and
the first process further includes determining a size of a character, a number, or a symbol included in the image to be projected based on the information indicating the visual acuity of the user.

5. The image projection system according to claim 4, wherein
the terminal device further includes a display device; and
the first process further includes
holding test image data representing a test image,
generating the test image based on the test image data and control controlling the display device to display the test image,
holding visual acuity test image data representing a visual acuity test image including a visual target image for visual acuity testing,
outputting the visual acuity test image data to the image projection device, and
storing, in the storage device, information specifying the visual target image that has been selected from the visual acuity test image displayed by the display device as the information indicating the visual acuity of the user.

6. The image projection system according to claim 2, wherein
the terminal device further includes a display device; and
the first process further includes
holding test image data representing a test image,
generating the test image based on the test image data and controlling the display device to display the test image;
outputting the test image data to the image projection device, and
storing, in the storage device, a selected identifier selected from among the plurality of identifiers of the plurality of regions of the test image displayed by the display device as the position information.

7. The image projection system according to claim 1, wherein the first process further includes
causing the display device to display a selection screen for prompting selection of the projection information; and
storing the projection information selected at the selection screen in association with the position information in the storage device.

8. The image projection system according to claim 1 or 2, wherein
the terminal device further includes an audio input device configured to acquire audio that has been input; and
the first process further includes
acquiring the projection information;
acquiring audio that has been input to the audio input device,
converting the acquired audio into text information, and
projecting the text information onto the position based on the position information.

9. An image projection device comprising:
a light source that emits a light beam;
a scanning mirror;
a hardware memory that stores a program; and
a processor that executes the program to perform a process including
input inputting image data including projection information from a terminal device,
generating an image light beam based on the input image data and controlling emission of the image light beam from the light source, and
causing the scanning mirror to scan the image light beam and thereby projecting the image light beam as an image representing the projection information onto a predetermined position on a retina of an eyeball of a user,
wherein the predetermined position is determined based on position information input from the terminal device, the position information indicating a position on the retina of the user at which the projection information is to be projected, the position being specified by the user at a setting screen displayed by a display device of the terminal device for prompting the user to specify the position.

10. An image projection device comprising:
a light source that emits a light beam;
a scanning mirror;
a hardware memory that stores a program; and
a processor that executes the program to perform a process including
inputting image data including projection information from a terminal device,
generating an image light beam based on the input image data and controlling emission of the image light beam from the light source, and
causing the scanning mirror to scan the image light beam and thereby projecting the image light beam as an image representing the projection information onto a predetermined position on a retina of an eyeball of a user,
wherein the predetermined position is determined based on position information input from the terminal device, the position information indicating a position of an identifier of a region of a test image that has been visually perceived by the user from the test image that has been projected onto the retina of the user, the test image being divided into a plurality of regions including a plurality of identifiers associated with position information of the plurality of regions.

11. An image projection method implemented by an image projection system including an image projection device and a terminal device communicating with the image projection device, the image projection method comprising steps of:
the terminal device holding projection information to be projected by the image projection device;
the terminal device causing a display device to display a setting screen for prompting a user to specify a position on a retina of the user at which the projection information is to be projected, and associating position information indicating the position specified by the user at the setting screen with the projection information;
the terminal device acquiring the position information from a storage device that stores the position information;
the terminal device generating image data of an image that projects the projection information at the position indicated by the position information;
the terminal device outputting the image data to the image projection device;
the image projection device inputting the image data from the terminal device;
the image projection device generating an image light beam based on the input image data and controlling emission of the image light beam from a light source configured to emit a light beam;
the image projection device scanning the image light beam with a scanning mirror; and
the image projection device projecting the image light beam onto the retina of an eyeball of the user as the image represented by the image data.

12. An image projection method implemented by an image projection system including an image projection device and a terminal device communicating with the image projection device, the image projection method comprising steps of:

the terminal device holding projection information to be projected by the image projection device;

the terminal device acquiring from a storage device, position information indicating a position on a retina of a user at which the projection is to be projected, the position information stored in the storage device indicating a position of an identifier of a region of a test image that has been visually perceived by the user from the test image that has been projected onto the retina of the user, the test image being divided into a plurality of regions including a plurality of identifiers associated with position information of the plurality of regions;

the terminal device generating image data of an image that projects the projection information at the position indicated by the position information;

the terminal device outputting the image data to the image projection device;

the image projection device inputting the image data from the terminal device;

the image projection device generating an image light beam based on the input image data and controlling emission of the image light beam from a light source configured to emit a light beam;

the image projection device scanning the image light beam with a scanning mirror; and the image projection device projecting the image light beam onto the retina of an eyeball of the user as the image represented by the image data.

* * * * *